(12) United States Patent
Dorai et al.

(10) Patent No.: US 10,724,105 B2
(45) Date of Patent: Jul. 28, 2020

(54) DETECTION OF HUMAN UMBILICAL CORD TISSUE-DERIVED CELLS

(71) Applicant: DEPUY SYNTHES PRODUCTS, INC., Raynham, MA (US)

(72) Inventors: Haimanti Dorai, Exton, NJ (US); Reyna L. Favis, Phillipsburg, NJ (US); Xiang Yao, San Diego, CA (US); Yu Sun, Belle Mead, NJ (US); Anthony J. Kihm, Princeton, NJ (US); Stefanie Rassnick, Fort Washington, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 445 days.

(21) Appl. No.: 15/476,460

(22) Filed: Mar. 31, 2017

(65) Prior Publication Data

US 2017/0335409 A1 Nov. 23, 2017

Related U.S. Application Data

(62) Division of application No. 13/722,849, filed on Dec. 20, 2012, now Pat. No. 9,611,513.

(60) Provisional application No. 61/579,710, filed on Dec. 23, 2011.

(51) Int. Cl.
*C12Q 1/6888* (2018.01)
*G01N 33/68* (2006.01)
*G01N 33/569* (2006.01)

(52) U.S. Cl.
CPC ..... *C12Q 1/6888* (2013.01); *G01N 33/56972* (2013.01); *G01N 33/68* (2013.01); *G01N 2333/70589* (2013.01)

(58) Field of Classification Search
None
See application file for complete search history.

(56) References Cited

U.S. PATENT DOCUMENTS

| | | |
|---|---|---|
| 3,970,518 A | 7/1976 | Giaever |
| 4,018,886 A | 4/1977 | Giaever |
| 4,230,685 A | 10/1980 | Senyei et al. |
| 4,267,234 A | 5/1981 | Rembaum |
| 4,352,883 A | 10/1982 | Lim |
| 4,452,773 A | 6/1984 | Molday |
| 4,554,088 A | 11/1985 | Whitehead et al. |
| 4,659,678 A | 4/1987 | Forrest et al. |
| 4,795,698 A | 1/1989 | Owen et al. |
| 4,882,162 A | 11/1989 | Ikada et al. |
| 4,963,489 A | 10/1990 | Naughton et al. |
| 5,004,681 A | 4/1991 | Boyse et al. |
| 5,192,553 A | 3/1993 | Boyse et al. |
| 5,286,632 A | 2/1994 | Jones |
| 5,320,962 A | 6/1994 | Stiles et al. |
| 5,342,761 A | 8/1994 | MacLeod |
| 5,437,994 A | 8/1995 | Emerson et al. |
| 5,443,950 A | 8/1995 | Naughton et al. |
| 5,486,359 A | 1/1996 | Caplan et al. |
| 5,580,777 A | 12/1996 | Bernard et al. |
| 5,589,376 A | 12/1996 | Anderson et al. |
| 5,597,531 A | 1/1997 | Liberti et al. |
| 5,629,147 A | 5/1997 | Asgari et al. |
| 5,670,483 A | 9/1997 | Zhang et al. |
| 5,677,181 A | 10/1997 | Parish |
| 5,684,032 A | 11/1997 | Elliott et al. |
| 5,698,271 A | 12/1997 | Liberti et al. |
| 5,736,516 A | 4/1998 | Louis |
| 5,811,094 A | 9/1998 | Caplan et al. |
| 5,827,735 A | 10/1998 | Young et al. |
| 5,834,308 A | 11/1998 | Peck et al. |
| 5,840,580 A | 11/1998 | Terstappen et al. |
| 5,842,477 A | 12/1998 | Naughton et al. |
| 5,843,780 A | 12/1998 | Thomson |
| 5,869,079 A | 2/1999 | Wong et al. |
| 5,902,598 A | 5/1999 | Chen et al. |
| 5,902,741 A | 5/1999 | Purchio et al. |
| 5,906,934 A | 5/1999 | Grande et al. |
| 5,919,702 A | 7/1999 | Purchio et al. |

(Continued)

FOREIGN PATENT DOCUMENTS

| JP | 2003-235549 | 8/2003 |
|---|---|---|
| JP | 2004-254682 | 9/2004 |

(Continued)

OTHER PUBLICATIONS

In the U.S. Patent and Trademark Office, Non-Final Office Action in re: U.S. Appl. No. 10/877,012, dated Sep. 24, 2007, 18 pages.
In the U.S. Patent and Trademark Office, Final Office Action in re: U.S. Appl. No. 10/877,012, dated Mar. 15, 2007, 13 pages.
In the U.S. Patent and Trademark Office, Non-Final Office Action in re: U.S. Appl. No. 10/877,012, dated Jul. 18, 2006, 26 pages.
In the U.S. Patent and Trademark Office, Non-Final Office Action in re: U.S. Appl. No. 11/315,897, dated Jun. 13, 2008, 12 pages.
In the U.S. Patent and Trademark Office, Non-Final Office Action in re: U.S. Appl. No. 10/877,446, dated Feb. 28, 2008, 19 pages.

(Continued)

*Primary Examiner* — Blaine Lankford

(57) ABSTRACT

The invention relates to methods for detecting allogeneic therapeutic cells (such as human umbilical cord tissue-derived cells (hUTC)) in blood. The methods includes the steps of identifying one or more one or more markers positive for allogeneic therapeutic cells (e.g. hUTC) and one or more markers positive for human peripheral blood mononuclear cells (PBMC); providing a blood sample from a patient that has been treated with allogeneic therapeutic cells (e.g. hUTC), analyzing the sample using an assay method to detect one or more markers positive for PBMC and one or more markers positive for allogeneic therapeutic cells (e.g. hUTC); and distinguishing between the PBMC and one or more markers positive for allogeneic therapeutic cells (e.g. hUTC). In one embodiment, the cells are hUTC and the markers positive of hUTC include CD10 and/or CD13 and the one or more markers positive for PBMC includes CD45.

24 Claims, 9 Drawing Sheets

(56) References Cited

U.S. PATENT DOCUMENTS

| | | |
|---|---|---|
| 5,942,225 A | 8/1999 | Bruder et al. |
| 5,955,343 A | 9/1999 | Holmes et al. |
| 5,962,325 A | 10/1999 | Naughton et al. |
| 5,994,094 A | 11/1999 | Hötten et al. |
| 6,001,647 A | 12/1999 | Peck et al. |
| 6,022,743 A | 2/2000 | Naughton et al. |
| 6,059,968 A | 5/2000 | Wolf |
| 6,140,039 A | 10/2000 | Naughton et al. |
| 6,171,610 B1 | 1/2001 | Vacanti et al. |
| 6,194,454 B1 | 2/2001 | Dow |
| 6,200,606 B1 | 3/2001 | Peterson et al. |
| 6,200,806 B1 | 3/2001 | Thomson |
| 6,214,369 B1 | 4/2001 | Grande et al. |
| 6,251,090 B1 | 6/2001 | Avery et al. |
| 6,291,240 B1 | 9/2001 | Mansbridge et al. |
| 6,323,188 B1 | 11/2001 | Weissman |
| 6,326,201 B1 | 12/2001 | Fung et al. |
| 6,331,313 B1 | 12/2001 | Wong et al. |
| 6,333,029 B1 | 12/2001 | Vyakarnam et al. |
| 6,355,239 B1 | 3/2002 | Bruder et al. |
| 6,355,699 B1 | 3/2002 | Vyakarnam et al. |
| 6,358,737 B1 | 3/2002 | Bonewald et al. |
| 6,365,362 B1 | 4/2002 | Terstappen et al. |
| 6,372,494 B1 | 4/2002 | Naughton et al. |
| 6,375,972 B1 | 4/2002 | Guo et al. |
| 6,387,367 B1 | 5/2002 | Davis-Sproul et al. |
| 6,391,297 B1 | 5/2002 | Halvorsen |
| 6,429,013 B1 | 8/2002 | Halvorsen et al. |
| 6,436,704 B1 | 8/2002 | Roberts et al. |
| 6,497,875 B1 | 12/2002 | Sorrell et al. |
| 6,528,245 B2 | 3/2003 | Sanchez-Ramos et al. |
| 6,534,084 B1 | 3/2003 | Vyakarnam et al. |
| 6,555,374 B1 | 4/2003 | Gimble et al. |
| 6,599,323 B2 | 7/2003 | Melican et al. |
| 6,610,535 B1 | 8/2003 | Lu et al. |
| 6,638,765 B1 | 10/2003 | Rosenberg |
| 6,673,606 B1 | 1/2004 | Tennekoon et al. |
| 6,680,198 B1 | 1/2004 | Snyder et al. |
| 6,686,198 B1 | 2/2004 | Melton et al. |
| 6,703,017 B1 | 3/2004 | Peck et al. |
| 6,916,655 B2 | 7/2005 | Yasumoto et al. |
| 7,413,734 B2 | 8/2008 | Mistry et al. |
| 7,510,873 B2 | 3/2009 | Mistry et al. |
| 7,524,489 B2 | 4/2009 | Messina et al. |
| 7,560,276 B2 | 7/2009 | Harmon et al. |
| 7,863,012 B2 | 1/2011 | Rao et al. |
| 7,875,272 B2 | 1/2011 | Messina et al. |
| 7,875,273 B2 | 1/2011 | Messina et al. |
| 8,277,796 B2 | 10/2012 | Messina et al. |
| 8,283,160 B2 | 10/2012 | Frey et al. |
| 8,318,483 B2 | 11/2012 | Mistry et al. |
| 9,611,513 B2 | 4/2017 | Dorai et al. |
| 2001/0024824 A1 | 9/2001 | Moss et al. |
| 2001/0031256 A1 | 10/2001 | Edge |
| 2001/0046489 A1 | 11/2001 | Habener et al. |
| 2002/0022676 A1 | 2/2002 | He et al. |
| 2002/0028510 A1 | 3/2002 | Sanberg et al. |
| 2002/0062151 A1 | 5/2002 | Altman et al. |
| 2002/0064519 A1 | 5/2002 | Bruder et al. |
| 2002/0081725 A1 | 6/2002 | Tsang et al. |
| 2002/0098584 A1 | 7/2002 | Palmer et al. |
| 2002/0119565 A1 | 8/2002 | Clarke et al. |
| 2002/0123141 A1 | 9/2002 | Hariri |
| 2002/0150986 A1 | 10/2002 | Lau |
| 2002/0151056 A1 | 10/2002 | Sasai et al. |
| 2002/0160471 A1 | 10/2002 | Kisiday et al. |
| 2002/0160510 A1 | 10/2002 | Hariri |
| 2002/0164307 A1 | 11/2002 | Habener et al. |
| 2002/0164791 A1 | 11/2002 | Van Der Kooy et al. |
| 2002/0168763 A1 | 11/2002 | Yan et al. |
| 2002/0182728 A1 | 12/2002 | Ramiya et al. |
| 2002/0187550 A1 | 12/2002 | Dinsmore et al. |
| 2002/0192816 A1 | 12/2002 | Roberts et al. |
| 2003/0003574 A1 | 1/2003 | Toma et al. |
| 2003/0007954 A1 | 1/2003 | Naughton et al. |
| 2003/0022369 A1 | 1/2003 | Fillmore et al. |
| 2003/0031657 A1 | 2/2003 | Habener et al. |
| 2003/0032178 A1 | 2/2003 | Williams et al. |
| 2003/0032179 A1 | 2/2003 | Hariri |
| 2003/0032183 A1 | 2/2003 | Sheridan |
| 2003/0049837 A1 | 3/2003 | Weiss et al. |
| 2003/0059939 A1 | 3/2003 | Page et al. |
| 2003/0082155 A1 | 5/2003 | Habener et al. |
| 2003/0082160 A1 | 5/2003 | Yu et al. |
| 2003/0096409 A1 | 5/2003 | Yasumoto et al. |
| 2003/0104997 A1 | 6/2003 | Black et al. |
| 2003/0109036 A1 | 6/2003 | Wu |
| 2003/0113910 A1 | 6/2003 | Levanduski |
| 2003/0118566 A1 | 6/2003 | Neuman et al. |
| 2003/0124721 A1 | 7/2003 | Cheatham et al. |
| 2003/0138948 A1 | 7/2003 | Fisk et al. |
| 2003/0138951 A1 | 7/2003 | Yin |
| 2003/0148513 A1 | 8/2003 | Sugaya et al. |
| 2003/0161818 A1 | 8/2003 | Weiss et al. |
| 2003/0162290 A1 | 8/2003 | Inoue et al. |
| 2003/0170215 A1 | 9/2003 | Tsang et al. |
| 2003/0175963 A1 | 9/2003 | Rosenberg |
| 2003/0180269 A1 | 9/2003 | Hariri |
| 2003/0186439 A1 | 10/2003 | Nakauchi et al. |
| 2003/0199447 A1 | 10/2003 | Goldman et al. |
| 2003/0203483 A1 | 10/2003 | Seshi |
| 2003/0203484 A1 | 10/2003 | Black et al. |
| 2003/0207450 A1 | 11/2003 | Young et al. |
| 2003/0211087 A1 | 11/2003 | Goldman |
| 2003/0211603 A1 | 11/2003 | Earp et al. |
| 2003/0211605 A1 | 11/2003 | Lee et al. |
| 2003/0212024 A1 | 11/2003 | Keating et al. |
| 2003/0219894 A1 | 11/2003 | Seino et al. |
| 2003/0228295 A1 | 12/2003 | Svendsen |
| 2003/0235563 A1 | 12/2003 | Strom et al. |
| 2003/0235909 A1 | 12/2003 | Hariri et al. |
| 2004/0005704 A1 | 1/2004 | Csete et al. |
| 2004/0009593 A1 | 1/2004 | Keirstead et al. |
| 2004/0014206 A1 | 1/2004 | Robl et al. |
| 2004/0014210 A1 | 1/2004 | Jessell et al. |
| 2004/0014211 A1 | 1/2004 | Ogle et al. |
| 2004/0014662 A1 | 1/2004 | Lindquist et al. |
| 2004/0028660 A1 | 2/2004 | Hariri et al. |
| 2004/0029269 A1 | 2/2004 | Goldman et al. |
| 2004/0033597 A1 | 2/2004 | Toma et al. |
| 2004/0037818 A1 | 2/2004 | Brand et al. |
| 2004/0048372 A1 | 3/2004 | Hariri |
| 2004/0058412 A1 | 3/2004 | Ho et al. |
| 2004/0063202 A1 | 4/2004 | Petersen et al. |
| 2004/0072344 A1 | 4/2004 | Inoue et al. |
| 2004/0136967 A1 | 7/2004 | Weiss et al. |
| 2004/0224409 A1 | 11/2004 | Pradier et al. |
| 2005/0019865 A1 | 1/2005 | Kihm et al. |
| 2005/0032209 A1 | 2/2005 | Messina et al. |
| 2005/0037491 A1 | 2/2005 | Mistry et al. |
| 2005/0054098 A1 | 3/2005 | Mistry et al. |
| 2005/0058629 A1 | 3/2005 | Harmon et al. |
| 2005/0058630 A1 | 3/2005 | Harris et al. |
| 2005/0058631 A1 | 3/2005 | Kihm et al. |
| 2005/0074435 A1 | 4/2005 | Casper et al. |
| 2005/0089513 A1 | 4/2005 | Sakuragawa et al. |
| 2005/0148074 A1 | 7/2005 | Davies et al. |
| 2005/0249731 A1 | 11/2005 | Aslan et al. |
| 2006/0153816 A1 | 7/2006 | Brown et al. |
| 2006/0153817 A1 | 7/2006 | Kihm et al. |
| 2006/0153818 A1 | 7/2006 | Dhanaraj et al. |
| 2006/0154366 A1 | 7/2006 | Brown et al. |
| 2006/0154367 A1 | 7/2006 | Kihm et al. |
| 2006/0188983 A1 | 8/2006 | Harris et al. |
| 2006/0223177 A1 | 10/2006 | Harris et al. |
| 2006/0233765 A1 | 10/2006 | Messina et al. |
| 2006/0233766 A1 | 10/2006 | Messina et al. |
| 2006/0234376 A1 | 10/2006 | Mistry et al. |
| 2007/0009494 A1 | 1/2007 | Mistry et al. |
| 2007/0014771 A1 | 1/2007 | Mistry et al. |
| 2007/0036767 A1 | 2/2007 | Mistry et al. |
| 2007/0105133 A1 | 5/2007 | Clarke et al. |
| 2007/0178533 A1 | 8/2007 | Poccia et al. |
| 2007/0275362 A1 | 11/2007 | Edinger et al. |

(56) References Cited

U.S. PATENT DOCUMENTS

| | | |
|---|---|---|
| 2010/0158877 A1 | 6/2010 | Colter et al. |
| 2010/0210013 A1 | 8/2010 | Mistry et al. |
| 2010/0215714 A1 | 8/2010 | Messina et al. |
| 2010/0203622 A1 | 10/2010 | Popma |
| 2010/0260843 A1 | 10/2010 | Messina et al. |
| 2011/0104718 A1 | 5/2011 | Rao et al. |
| 2012/0315251 A1 | 12/2012 | Harris et al. |
| 2013/0022585 A1 | 1/2013 | Messina et al. |

FOREIGN PATENT DOCUMENTS

| | | |
|---|---|---|
| WO | WO 90/11354 | 10/1990 |
| WO | WO 92/03917 | 3/1992 |
| WO | WO 93/04169 | 3/1993 |
| WO | WO 94/25584 | 11/1994 |
| WO | WO 95/17911 | 7/1995 |
| WO | WO 95/23216 | 8/1995 |
| WO | WO 96/01316 | 1/1996 |
| WO | WO 96/05309 | 2/1996 |
| WO | WO 98/17791 | 4/1998 |
| WO | WO 98/51317 | 11/1998 |
| WO | WO 99/03973 | 1/1999 |
| WO | WO 00/09666 | 2/2000 |
| WO | WO 00/73421 | 12/2000 |
| WO | WO 01/11011 | 2/2001 |
| WO | WO 01/19379 | 3/2001 |
| WO | WO 01/34775 | 5/2001 |
| WO | WO 02/046373 | 6/2002 |
| WO | WO 02/059278 | 8/2002 |
| WO | WO 02/062969 | 8/2002 |
| WO | WO 02/063962 | 8/2002 |
| WO | WO 02/064748 | 8/2002 |
| WO | WO 02/064755 | 8/2002 |
| WO | WO 02/086107 | 10/2002 |
| WO | WO 03/023020 | 3/2003 |
| WO | WO 03/025149 | 3/2003 |
| WO | WO 03/029443 | 4/2003 |
| WO | WO 03/029445 | 4/2003 |
| WO | WO 03/039489 | 5/2003 |
| WO | WO 03/042405 | 5/2003 |
| WO | WO 03/048336 | 6/2003 |
| WO | WO 03/055992 | 7/2003 |
| WO | WO 03/064601 | 8/2003 |
| WO | WO 03/066832 | 8/2003 |
| WO | WO 03/068937 | 8/2003 |
| WO | WO 03/070922 | 8/2003 |
| WO | WO 03/072728 | 9/2003 |
| WO | WO 03/080822 | 10/2003 |
| WO | WO 03/087333 | 10/2003 |
| WO | WO 03/087392 | 10/2003 |
| WO | WO 03/089619 | 10/2003 |
| WO | WO 03/100038 | 12/2003 |
| WO | WO 03/102134 | 12/2003 |
| WO | WO 03/102151 | 12/2003 |
| WO | WO 03/104442 | 12/2003 |
| WO | WO 04/011012 | 2/2004 |
| WO | WO 04/011621 | 2/2004 |
| WO | WO 04/016747 | 2/2004 |
| WO | WO 04/0104549 A2 | 2/2004 |
| WO | WO 04/023100 | 3/2004 |
| WO | WO 04/072273 | 8/2004 |
| WO | WO 04/111207 | 12/2004 |
| WO | WO 05/001076 | 1/2005 |
| WO | WO 05/001077 A2 | 1/2005 |
| WO | WO 05/001078 | 1/2005 |
| WO | WO 05/001079 | 1/2005 |
| WO | WO 05/001080 A2 | 1/2005 |
| WO | WO 05/003334 A2 | 1/2005 |
| WO | WO 05/010162 | 2/2005 |
| WO | WO 05/021738 | 3/2005 |
| WO | WO 05/038012 | 4/2005 |
| WO | WO 05/042703 | 5/2005 |
| WO | WO 06/071773 | 7/2006 |
| WO | WO 06/071777 | 7/2006 |
| WO | WO 06/071778 | 7/2006 |
| WO | WO 06/071794 A2 | 7/2006 |
| WO | WO 06/071802 | 7/2006 |
| WO | WO 06/083394 | 8/2006 |
| WO | WO 06/105152 | 10/2006 |
| WO | WO 06/117237 | 11/2006 |
| WO | WO 07/051625 | 5/2007 |
| WO | WO 13/096686 A1 | 6/2013 |
| WO | WO 13/096686 R | 6/2013 |

OTHER PUBLICATIONS

In the U.S. Patent and Trademark Office, Final Office Action in re: U.S. Appl. No. 10/877,446, dated Jun. 27, 2007, 24 pages.
In the U.S. Patent and Trademark Office, Non-Final Office Action in re: U.S. Appl. No. 10/877,446, dated Nov. 20, 2006, 24 pages.
In the U.S. Patent and Trademark Office, Non-Final Office Action in re: U.S. Appl. No. 10/877,269, dated Jan. 17, 2008, 10 pages.
In the U.S. Patent and Trademark Office, Final Office Action in re: U.S. Appl. No. 10/877,269, dated Aug. 14, 2007, 6 pages.
In the U.S. Patent and Trademark Office, Non-Final Office Action in re: U.S. Appl. No. 10/877,269, dated May 3, 2007, 12 pages.
In the U.S. Patent and Trademark Office, Non-Final Office Action in re: U.S. Appl. No. 11/315,898, dated Feb. 13, 2008, 12 pages.
In the U.S. Patent and Trademark Office, Final Office Action in re: U.S. Appl. No. 11/315,943, dated Aug. 20, 2008, 7 pages.
In the U.S. Patent and Trademark Office, Non-Final Office Action in re: U.S. Appl. No. 11/315,943, dated Feb. 12, 2008, 11 pages.
In the U.S. Patent and Trademark Office, Non-Final Office Action in re: U.S. Appl. No. 10/877,445, dated Jul. 11, 2008, 12 pages.
In the U.S. Patent and Trademark Office, Non-Final Office Action in re: U.S. Appl. No. 10/877,445, dated Mar. 19, 2008, 12 pages.
In the U.S. Patent and Trademark Office, Final Office Action in re: U.S. Appl. No. 10/877,445, dated Nov. 5, 2007, 17 pages.
In the U.S. Patent and Trademark Office, Non-Final Office Action in re: U.S. Appl. No. 10/877,445, dated May 17, 2007, 19 pages.
In the U.S. Patent and Trademark Office, Final Office Action in re: U.S. Appl. No. 10/877,445, dated Sep. 11, 2006, 30 pages.
In the U.S. Patent and Trademark Office, Non-Final Office Action in re: U.S. Appl. No. 10/877,445, dated Nov. 21, 2005, 17 pages.
In the U. S. Patent and Trademark Office, Non-Final Office Action in re: U.S. Appl. No. 11/322,372, dated Sep. 3, 2008, 13 pages.
In the U.S. Patent and Trademark Office, Non-Final Office Action in re: U.S. Appl. No. 10/877,541, dated Jul. 25, 2007, 13 pages.
In the U.S. Patent and Trademark Office, Advisory Office Action in re: U.S. Appl. No. 10/877,541, dated Apr. 18, 2007, 4 pages.
In the U.S. Patent and Trademark Office, Final Office Action in re: U.S. Appl. No. 10/877,541, dated Jan. 10, 2007, 19 pages.
In the U.S. Patent and Trademark Office, Non-Final Office Action in re: U.S. Appl. No. 10/877,541, dated Feb. 22, 2006, 13 pages.
In the U.S. Patent and Trademark Office, Advisory Office Action in re: U.S. Appl. No. 11/317,574, dated Jun. 4, 2008, 3 pages.
In the U.S. Patent and Trademark Office, Final Office Action in re: U.S. Appl. No. 11/317,574, dated Mar. 5, 2008, 10 pages.
In the U.S. Patent and Trademark Office, Final Office Action in re: U.S. Appl. No. 11/317,574, dated Aug. 10, 2007, 14 pages.
In the U.S. Patent and Trademark Office, Non-Final Office Action in re: U.S. Appl. No. 10/877,009, dated Jan. 9, 2008, 12 pages.
In the U.S. Patent and Trademark Office, Final Office Action in re: U.S. Appl. No. 10/877,009, dated Jul. 25, 2007, 17 pages.
In the U.S. Patent and Trademark Office, Non-Final Office Action in re: U.S. Appl. No. 10/877,009, dated Nov. 21, 2006, 15 pages.
In the U.S. Patent and Trademark Office, Non-Final Office Action in re: U.S. Appl. No. 10/876,998, dated Jun. 25, 2008, 9 pages.
In the U.S. Patent and Trademark Office, Final Office Action in re: U.S. Appl. No. 10/876,998, dated Feb. 27, 2008, 18 pages.
In the U.S. Patent and Trademark Office, Non-Final Office Action in re: U.S. Appl. No. 10/876,998, dated Jul. 13, 2007, 30 pages.
In the U.S. Patent and Trademark Office, Final Office Action in re: U.S. Appl. No. 10/876,998, dated Oct. 18, 2006, 29 pages.
In the U.S. Patent and Trademark Office, Non-Final Office Action in re: U.S. Appl. No. 10/876,998, dated Mar. 30, 2006, 24 pages.
In the U.S. Patent and Trademark Office, Non-Final Office Action in re: U.S. Appl. No. 11/321,863, dated Aug. 19, 2008, 15 pages.

(56) References Cited

OTHER PUBLICATIONS

In the U.S. Patent and Trademark Office, Non-Final Office Action in re: U.S. Appl. No. 11/322,003, dated Jun. 2, 2008, 14 pages.
In the U.S. Patent and Trademark Office, Non-Final Office Action in re: U.S. Appl. No. 11/321,864, dated Apr. 21, 2008, 7 pages.
In the U.S. Patent and Trademark Office, Final Office Action in re: U.S. Appl. No. 11/315,969, dated May 19, 2008, 9 pages.
In the U.S. Patent and Trademark Office, Non-Final Office Action in re: U.S. Appl. No. 11/315,969, dated Nov. 1, 2007, 11 pages.
In the U. S. Patent and Trademark Office, Final Office Action in re: U.S. Appl. No. 11/315,898, dated Sep. 16, 2008, 8 pages.
In the U. S. Patent and Trademark Office, Non-Final Office Action, in re: U.S. Appl. No. 11/297,156, dated Oct. 10, 2008, 11 pages.
In the U. S. Patent and Trademark Office, Non-Final Office Action in re: U.S. Appl. No. 11/317,574, dated Sep. 30, 2008, 23 pages.
In the U. S. Patent and Trademark Office, Final Office Action in re: U.S. Appl. No. 11/315,969, dated Dec. 23, 2008, 11 pages.
In the U. S. Patent and Trademark Office, Final Office Action in re: U.S. Appl. No. 11/321,864, dated Jan. 8, 2009, 11 pages.
In the U. S. Patent and Trademark Office, Final Office Action in re: U.S. Appl. No. 11/321,863, dated Feb. 12, 2009, 15 pages.
In the U. S. Patent and Trademark Office, Non-Final Office Action in re: U.S. Appl. No. 11/315,943, dated Feb. 20, 2009, 9 pages.
In the U. S. Patent and Trademark Office, Final Office Action in re: U.S. Appl. No. 10/877,445, dated Mar. 19, 2009, 15 pages.
In the U. S. Patent and Trademark Office, Non-Final Office Action in re: U.S. Appl. No. 11/481,481, dated Mar. 20, 2009, 12 pages.
In the U. S. Patent and Trademark Office, Final Office Action in re: U.S. Appl. No. 11/315,897, dated Mar. 20, 2009, 13 pages.
In the U. S. Patent and Trademark Office, Non-Final Office Action in re: U.S. Appl. No. 11/481,480, dated Mar. 20, 2009, 13 pages.
In the U. S. Patent and Trademark Office, Final Office Action in re: U.S. Appl. No. 11/322,003, dated Feb. 13, 2009, 17 pages.
In the U. S. Patent and Trademark Office, Final Office Action in re: U.S. Appl. No. 10/876,998, dated Feb. 13, 2009, 10 pages.
In the U. S. Patent and Trademark Office, Final Office Action in re: U.S. Appl. No. 11/322,372, dated Feb. 13, 2009, 14 pages.
In the U. S. Patent and Trademark Office, Non-Final Office Action in re: U.S. Appl. No. 11/315,898, dated Feb. 18, 2009, 10 pages.
In the U. S. Patent and Trademark Office, Non-Final Office Action in re: U.S. Appl. No. 11/481,456, dated Apr. 16, 2009, 14 pages.
In the U. S. Patent and Trademark Office, Final Office Action in re: U.S. Appl. No. 11/317,574, dated Apr. 29, 2009, 21 pages.
In the U. S. Patent and Trademark Office, Advisory Action in re: U.S. Appl. No. 11/315,969, dated Sep. 29, 2009, 9 pages.
In the U. S. Patent and Trademark Office, Advisory Action in re: U.S. Appl. No. 11/322,372, dated May 12, 2009, 10 pages.
In the U. S. Patent and Trademark Office, Non-Final Office Action in re: U.S. Appl. No. 10/877,446, dated Jun. 12, 2009, 16 pages.
In the U. S. Patent and Trademark Office, Final Office Action in re: U.S. Appl. No. 11/322,372, dated Aug. 6, 2009, 12 pages.
In the U. S. Patent and Trademark Office, Final Office Action in re: U.S. Appl. No. 11/481,456, dated Oct. 9, 2009, 11 pages.
In the U. S. Patent and Trademark Office, Non-Final Office Action in re: U.S. Appl. No. 11/612,872, dated Oct. 2, 2009, 9 pages.
In the U. S. Patent and Trademark Office, Final Office Action in re: U.S. Appl. No. 10/877,445, dated Aug. 25, 2009, 18 pages.
In the U. S. Patent and Trademark Office, Final Office Action in re: U.S. Appl. No. 11/321,863, dated Aug. 7, 2009, 11 pages.
In the U. S. Patent and Trademark Office, Final Office Action in re: U.S. Appl. No. 11/321,864, dated Aug. 17, 2009, 13 pages.
In the U. S. Patent and Trademark Office, Final Office Action in re: U.S. Appl. No. 11/315,969, dated May 13, 2009, 11 pages.
In the U. S. Patent and Trademark Office, Non-Final Office Action in re: U.S. Appl. No. 11/317,574, dated Dec. 28, 2009, 26 pages.
In the U. S. Patent and Trademark Office, Non-Final Office Action in re: U.S. Appl. No. 11/321,863, dated Jan. 7, 2010, 13 pages.
In the U. S. Patent and Trademark Office, Non-Final Office Action in re: U.S. Appl. No. 11/321,864, dated Jan. 27, 2010, 12 pages.

In the U. S. Patent and Trademark Office, Non-Final Office Action in re: U.S. Appl. No. 11/315,969, dated Jan. 27, 2010, 12 pages.
In the U. S. Patent and Trademark Office, Non-Final Office Action in re: U.S. Appl. No. 11/315,943, dated Feb. 19, 2010, 13 pages.
In the U. S. Patent and Trademark Office, Final Office Action in re: U.S. Appl. No. 11/316,104, dated Mar. 24, 2010, 12 pages.
In the U. S. Patent and Trademark Office, Non-Final Office Action in re: U.S. Appl. No. 11/481,456, dated May 14, 2010, 9 pages.
In the U. S. Patent and Trademark Office, Non-Final Office Action in re: U.S. Appl. No. 11/481,481, dated May 13, 2010, 9 pages.
In the U. S. Patent and Trademark Office, Final Office Action in re: U.S. Appl. No. 11/315,897, dated May 14, 2010, 13 pages.
In the U. S. Patent and Trademark Office, Non-Final Office Action in re: U.S. Appl. No. 11/481,480, dated May 17, 2010, 10 pages.
In the U. S. Patent and Trademark Office, Final Office Action in re: U.S. Appl. No. 11/612,872, dated May 26, 2010, 11 pages.
In the U. S. Patent and Trademark Office, Final Office Action in re: U.S. Appl. No. 10/877,445, dated Jul. 8, 2010, 20 pages.
In the U. S. Patent and Trademark Office, Non-Final Office Action in re: U.S. Appl. No. 10/876,998, dated Aug. 3, 2010, 14 pages.
In the U. S. Patent and Trademark Office, Final Office Action in re: U.S. Appl. No. 11/321,863, dated Aug. 17, 2010, 15 pages.
In the U. S. Patent and Trademark Office, Final Office Action in re: U.S. Appl. No. 11/321,864, dated Aug. 31, 2010, 7 pages.
In the U. S. Patent and Trademark Office, Final Office Action in re: U.S. Appl. No. 11/315,969, dated Aug. 31, 2010, 6 pages.
In the U. S. Patent and Trademark Office, Final Office Action in re: U.S. Appl. No. 11/322,372, dated Aug. 31, 2010, 11 pages.
In the U. S. Patent and Trademark Office, Non-Final Office Action in re: U.S. Appl. No. 11/316,104, dated Sep. 21, 2010, 13 pages.
In the U. S. Patent and Trademark Office, Final Office Action in re: U.S. Appl. No. 11/317,574, dated Oct. 6, 2010, 16 pages.
In the U. S. Patent and Trademark Office, Non-Final Office Action in re: U.S. Appl. No. 11/939,360, dated Oct. 7, 2010, 4 pages.
In the U. S. Patent and Trademark Office, Non-Final Office Action in re: U.S. Appl. No. 12/054,718, dated Sep. 29, 2010, 18 pages.
In the U. S. Patent and Trademark Office, Non-Final Office Action in re: U.S. Appl. No. 11/322,372, dated Jan. 21, 2010, 10 pages.
In the U. S. Patent and Trademark Office, Final Office Action in re: U.S. Appl. No. 11/481,481, dated Sep. 18, 2009, 11 pages.
In the U. S. Patent and Trademark Office, Advisory Action in re: U.S. Appl. No. 11/315,897, dated Jun. 30, 2009, 3 pages.
In the U. S. Patent and Trademark Office, Non-Final Office Action in re: U.S. Appl. No. 11/315,897, dated Sep. 2, 2009, 12 pages.
In the U. S. Patent and Trademark Office, Final Office Action in re: U.S. Appl. No. 11/481,480, dated Sep. 17, 2009, 12 pages.
In the U. S. Patent and Trademark Office, Final Office Action in re: U.S. Appl. No. 10/877,446, dated Jun. 4, 2010, 17 pages.
In the U. S. Patent and Trademark Office, Non-Final Office Action in re: U.S. Appl. No. 11/316,104, dated Oct. 31, 2008, 15 pages.
In the U. S. Patent and Trademark Office, Final Office Action in re: U.S. Appl. No. 10/876,998, dated May 27, 2009, 14 pages.
In the U. S. Patent and Trademark Office, Non-Final Office Action in re: U.S. Appl. No. 10/876,998, dated Nov. 24, 2009, 7 pages.
In the U. S. Patent and Trademark Office, Non-Final Office Action in re: U.S. Appl. No. 10/876,998, dated Feb. 1, 2011, 11 pages.
In the U. S. Patent and Trademark Office, Non-Final Office Action in re: U.S. Appl. No. 11/481,456, dated Feb. 3, 2011, 10 pages.
In the U. S. Patent and Trademark Office, Non-Final Office Action in re: U.S. Appl. No. 11/481,481, dated Feb. 3, 2011, 10 pages.
In the U. S. Patent and Trademark Office, Non-Final Office Action in re: U.S. Appl. No. 12/389,305, dated Feb. 8, 2011, 14 pages.
In the U. S. Patent and Trademark Office, Non-Final Office Action in re: U.S. Appl. No. 11/481,480, dated Feb. 3, 2011, 10 pages.
In the U.S. Patent and Trademark Office, Final Office Action in re: U.S. Appl. No. 10/877,446, dated Nov. 2, 2011, 12 pages.
In the U.S. Patent and Trademark Office, Final Office Action in re: U.S. Appl. No. 12/389,305, dated Oct. 12, 2011, 12 pages.
In the U.S. Patent and Trademark Office, Final Office Action in re: U.S. Appl. No. 12/429,849, dated Mar. 20, 2012, 9 pages.
In the U. S. Patent and Trademark Office, Final Office Action in re: U.S. Appl. No. 11/481,456, dated Oct. 11, 2011, 6 pages.

(56) References Cited

OTHER PUBLICATIONS

In the U.S. Patent and Trademark Office, Non-Final Office Action in re: U.S. Appl. No. 12/697,081, dated Apr. 2, 2012, 8 pages.
In the U.S. Patent and Trademark Office, Non-Final Office Action in re: U.S. Appl. No. 13/605,716, dated Feb. 13, 2013, 13 pages.
In the U.S Patent and Trademark Office, Final Office Action in re: U.S. Appl. No. 11/939,360, dated Mar. 15, 2011, 6 pages.
In the U.S. Patent and Trademark Office, Non-Final Office Action in re: U.S. Appl. No. 13/722,849 dated Jan. 16, 2014, 17 pages.
In the U.S. Patent and Trademark Office, Final Office Action in re: U.S. Appl. No. 13/722,849 dated Jul. 28, 2016, 18 pages.
Abbas, A.K. et al., *Cellular and Molecular Immunology*, 5th Ed. (2003) Saunders, Philadelphia, p. 171.
Aboody, K.S. et al., "Neural Stem Cells Display Extensive Tropism for Pathology in Adult Brain: Evidence From Intracranial Gliomase," *PNAS*, 2000; 97(23):12846-12851.
Agbulut, O. et al., "Comparison of Human Skeletal Myoblasts and Bone Marrow-Derived CD133+ Progenitors for the Repair of Infarcted Myocardium," *Journal of the American College of Cardiology*, 2004; 44(2):458-463.
Aggarwal et al., "Human Mesenchymal Stem Cells Modulate Allogeneic Immune Cell Responses," *Blood*, 2005; 105(4):1815-1822.
Aldskogius, H. et al., "Strategies for Repair of the Deafferented Spinal Cord," *Brain Res. Rev.*, 2002; 40:301-308.
Armulik, A. et al., "Endothelial/Pericyte Interactions," *Circ. Res.*, 2005; 97:512-523.
Auda-Boucher, G. et al., "Staging of the Commitment of Murine Cardiac Cell Progenitors," *Dev. Bio.*, 2000; 225(1):214-225.
Avital, I. et al., "Isolation, Characterization, and Transplantation of Bone Marrow-Derived Hepatocyte Stem Cells," *Biochem. & Biophys. Res. Comm.*, 2001; 288:156-164.
Azizi, S.A. et al., "Engraftment and Migration of Human Bone Marrow Stromal Cells Implanted in the Brains of Albino Rats—Similarities to Astrocyte Grafts," *Proc. Natl. Acad. Sci. USA*, 1998; 95:3908-3913.
Bader, P. et al., "How and when should we monitor chimerism after allogeneic stem cell transplantation?", *Bone Marrow Transplantation*, 2005; 35:107-119.
Bakhshi, et al., "Mesenchymal stem cells from the Wharton's jelly of umbilical cord segments provide stromal support for the maintenance of cord blood hematopoietic stem cells during long-term ex vivo culture", *Transfusion*, 2008; 48: 2638-2644.
Bensinger, W. L. et al., "Allogeneic Peripheral Blood Stem Cell Transplantation in Patients With Advanced Hematologic Malignancies: A Retrospective Comparison With Marrow Transplantation," *Blood*, 1996; 88:2794-2800.
Bradley, B.A., "The Role of HLA Matching in Transplantation," *Immunol. Lett.*, 1991; 29:55-59.
Bunge et al., "The Role of the Schwann Cell in Trophic Support and Regeneration," *Journal of Neurology*, 1994; 241:536.
Can et al., "Concise Review: Human Umbilical Cord Stroma with Regard to the Source of Fetus-Derived Stem Cells," *Stem Cells*, 2007; 25:2886-2895.
Caplan, A.I. et al., "Mesenchymal Stem Cells: Building Blocks for Molecular Medicine in the 21st Century," *Trends in Molecular Med.*, 2001; 7(6):259-264.
Cheng, A. et al. "Nitric Oxide Acts in a Positive Feedback Loop With BDNF to Regulate Neural Progenitor Cell Proliferation and Differentiation in the Mammalian Brain," *Dev. Biol.*, 2003; 258:319-333.
Cho et al., "Immunogenicity of Umbilical Cord Tissue-Derived Cells," *Blood*, 2008; 111(1):430-438.
Daley, G.Q. et al., "Realistic Prospects for Stem Cell Therapeutics," *Hematol.*, 2003; 398-418.
D'Arena, G., "Flow cytometric characterization of human umbilical cord blood lymphocytes: immunophenotypic features," *Haematologica*, 1998; 83:197-20.
Dekel-Naftali, M. et al., "Screening of human pluripotent stem cells using CGH and FISH reveals low-grade mosaic aneuploidy and a recurrent amplification of chromosome 1q," *European Journal of Human Genetics*, 2012; 20: 1248-1255.
Dimri, G.P. et al., "A Biomarker That Identifies Senescent Human Cells in Culture and in Aging Skin In Vivo," *Proc. Natl. Acad. Sci. USA*, 1995; 92:9363-9367.
Doyle, J., "Spiraling Complexity, Robustness, and Fragility in Biology," http://www.cds.caltech.edu/~doyle/CmplxNets/Bio1.pdf, available online Feb. 28, 2004.
Draper et al., "Surface Antigens of Human Embryonic Stem Cells: Changes Upon Differentiation in Culture," *J. Anat.*, 2002; 200:249-258.
Durnman, D.M. et al., "Analysis of the origin of marrow cells in bone marrow transplant recipients using a Y-chromosome-specific in situ hybridization assay," *Blood*, 1989; 74:2220-2236.
Dutton, R, et al., "Precursor Cells in the Subventricular Zone of the Adult Mouse are Actively Inhibited from Differentiating into Neurons," *Dev Neurosci*, 2000; 22:96-105.
Eblenkamp, M. et al., "Umbilical Cord Stromal Cells (UCSC). Cells Featuring Osteogenic Differentiation Potential," *Der Orthopade*, Dec. 2004; 33:1338-1345 (English abstract on p. 1339).
Eisenhofer, G.E. et al., "Tyrosinase: A Developmentally Specific Major Determinant of Peripheral Dopamine," *FASEB J.*, 2003; 17:1248-1255.
Erices et al., Mesenchymal Progenitor Cells in Human Umbilical Cord Blood, *Br. J. Haematol.*, 2000; 109:235-242.
Evers, B.M., et al., "Stem Cells in Clinical Practice," *J Am Coll Surg.*, 2003; 197(3):458-478.
Fiegel, H.C. et al., "Liver-Specific Gene Expression in Cultured Human Hematopoietic Stem Cells," *Stem Cells*, 2003; 21:98-104.
Fukuchi, Y. et al., "Human Placenta-Derived Cells Have Mesenchymal Stem/Progenitor Cell Potential," *Stem Cells*, 2004; 22:649-658.
Fukuda, K., "Reprogramming of Bone Marrow Mesenchymal Stem Cells Into Cardiomyocytes," *C.R. Biol.*, 2002; 325:1027-1038.
Gellersen, B. et al., "Cyclic AMP and Progesterone Receptor Cross-Talk in Human Endometrium: A Decidualizing Affair," *J. Endocrinol.*, 2003; 178(3):357-372.
Gerdes, D. et al., "Cloning and Tissue Expression of Two Putative Steroid Membrane Receptors," *Biol. Chem.*, 1998; 379:907-911.
Gökhan, S. et al., "Basic and Clinical Neuroscience Applications of Embryonic Stem Cells," *Anat. Rec. (New Anat)*, 2001; 265:142-156.
Goodwin, H.S. et al., "Multilineage Differentiation Activity by Cells Isolated from Umbilical Cord Blood: Expression of Bone, Fat, and Neural Markers," *Biology of Blood and Marrow Transplantation*, 2001; 7: 581-588.
Gosiewska, A. et al., "Development of a Three-Dimensional Transmigration Assay for Testing Cell-Polymer Interactions for Tissue Engineering Applications," *Tissue Eng.*, 2001; 7(3):267-277.
Gottlieb, D.I. "Large-Scale Sources of Neural Stem Cells," *Annu. Rev. Neurosci.*, 2002; 25:381-407.
Gupta, S. et al., "Isolation and Characterization of Kidney-Derived Stem Cells," *J. of Am. Soci. of Nephrol.*, 2006; 17(11):3028-3040.
Hall, JM et al., "Detection of Maternal Cells in Human Umbilical Cord Blood Using Fluorescence In Situ Hybridization," *Blood*, 1995; 86: 2829-2832.
Hayflick, L., "The Longevity of Cultured Human Cells," *J. Am. Geriatr. Soc.*, 1974; 22(1):1-12.
Hayflick, L., "The Strategy of Senescence," *Gerontologist*, 1974; 14(1):37-45.
Haynesworth et al., "Cell Surface Antigens on Human Marrow-Derived Mesenchymal Cells are Detected by Monoclonal Antibodies," *Bone*, 1992; 13:69-80.
Herrera, M.B. et al., "Mesenchymal Stem Cells Contribute to the Renal Repair of Acute Tubular Epithelial Injury," *Int. J. Mol. Med.*, 2004; 14(6):1035-1041.
Hishikawa, K. et al., "Musculin/MyoR is Expressed in Kidney Side Population Cells and Can Regulate Their Function," *Journal of Cell Biology*, 2005; 169(6):921-928.
Ho, et al., "En Bloc Transfer of Extracellular Matrix In Vitro," *Curr. Eye Res.*, 1996; 15:991-997.
Hongpaisan, J., "Inhibition of Proliferation of Contaminating Fibroblasts by D-Valine in Cultures of Smooth Muscle Cells From Human Myometrium," *Cell Biol. Int.*, 2000; 24(1):1-7.

(56) References Cited

OTHER PUBLICATIONS

Hoynowski, S.M. et al., "Characterization and Differentiation of Equine Umbilical Cord-Derived Matrix Cells," *Biochemical and Biophysical Research Communications*, 2007; 362:347-353.

Hu, A. et al., "Hepatic Differentiation From Embryonic Stem Cells In Vitro," *Chin. Med. J.*, 2003; 116(12):1893-1897.

Hughes, G.C. et al., "Therapeutic Angiogenesis in Chronically Ischemic Porcine Myocardium: Comparative Effects of BFGF and VEGF," *Ann. Thorac. Surg.*, 2004; 77:812-818.

Igura et al., "Human Placental Derived Stem Cells Differentiate into Neural Cells," *Blood*, 2002; 100(11): 517A (Abstract 2021).

In't Anker, P., et al., "Isolation of Mesenchymal Stem Cells of Fetal or Maternal Origin from Human Placenta," *Stem Cells*, 2004; 22:1338-1345.

Ishii, M. et al., "Molecular Markers Distinguish Bone Marrow Mesenchymal Stem Cells From Fibroblasts," *Biochemical and Biophysical Research Communications*, 2005; 332:297-303.

Ishizawa, K. et al. "Bone marrow-derived cells contribute to lung regeneration after elastase-induced pulmonary emphysema," *FEBS Letters*, 2004; 556:249-252.

Ito, Y. et al., "A Quantitative Assay Using Basement Membrane Extracts to Study Tumor Angiogenesis In Vivo," *Int. J. Cancer*, 1996; 67:148-152.

Jaffe, E.A. et al., "Culture of Human Endothelial Cells Derived From Umbilical Veins; Identification by Morphologic and Immunologic Criteria" *J Clin Invest*, 1973; 52:2745-2756.

Janderová, L. et al., "Human Mesenchymal Stem Cells as an In Vitro Model for Human Adipogenesis," *Obes. Res.*, 2003; 11(1):65-74.

Johe, K.K. et al., "Single Factors Direct the Differentiation of Stem Cells From the Fetal and Adult Central Nervous System," *Genes & Devel.*, 1996; 10:3129-3140.

Johnstone, B. et al., "In Vitro Chondrogenesis of Bone-Marrow-Derived Mesenchymal Progenitor Cells," *Exp. Cell Res.*, 1998; 238:265-272.

Jones, J. et al., "Insulin-Like Growth Factors and their Binding Proteins: Biological Actions," *Endocrine Review*, 1995; 16(1):3-34.

Karasawa, M. et al., "Long-Term Persistence of Host Cells Detected by X-Chromosome Gene-Based Assay in Patients Undergoing Gender-Mismatched Hematopoietic Stem Cell Transplantation," *American Journal of Hematology*, 2005; 80:101-105.

Kawata, M. et al., "Transcriptional Control of HLA-A,B,C Antigen in Human Placental Cytotrophoblast Isolated Using Trophoblast- and HLA-Specific Monoclonal Antibodies and the Fluorescence-Activated Cell Sorter," *J. Exp. Med.*, Sep. 1984; 160:633-651.

Keirstead, H. et al., "Human Embryonic Stem Cell-Derived Oligodendrocyte Progenitor Cell Transplants Remyelinate and Restore Locomotion after Spinal Cord Injury," *The Journal of Neuroscience*, 2005; 25(19):4694-4705.

Klein, A. K. et al., "T-cell recovery in adults and children following umbilical cord blood transplantation", Biology of Blood and Marrow Transplant, 2001; 7:454-466.

Kurtz, A. et al., "Activity in Fetal Bovine Serum that Stimulates Erythroid Colony Formation in Fetal Mouse Livers is Insulinlike Growth Factor I," *J. Clin. Invest.*, 1985; 76:1643-1648.

Kusama et al., "Growth and morphogenesis of mouse prostate epithelial cells in collagen gel matrix culture" Cell Biol Int Rep, 1989; 13:569-575.

Le Bouteiller, P. et al., "Soluble HLA-G1 at The Materno-Foetal Interface—A Review," *Placenta*, 2003; 24(Suppl. A):S10-S15. Also filed as "Bouteiller".

Li, A. et al., "IL-8 Directly Enhanced Endothelial Cell Survival, Proliferation, and Matrix Metalloproteinases Production and Regulated Angiogenesis," *J. Immunol.*, 2003; 170:3369-3376.

Li, C.D. et al, "Mesenchymal Stem Cells Derived From Human Placenta Suppress Allogeneic Umbilical Cord Blood Lymphocyte Proliferation," *Cell Research*, 2005; 15(7):539-547.

Liddiard, et al., "An Improved Method for the Preparation of Human Fetal and Adult Hepatocytes," *Arch. Toxicol.*, 1980; 44:107-112.

Linkhart et al., Growth Factors for Bone Growth and Repair: IGF, TGFβ and BMP1, *Bone*, 1996; 19(Suppl 1):1S-12S.

Liu, K. et al, "Constitutive and Regulated Expression of Telomerase Reverse Transcriptase (hTERT) in Human Lymphocytes," *Proc. Natl. Acad. Sci.*, 1999; 96:5147-5152.

Lockhart, D.J. et al., "Expression Monitoring by Hybridization to High-Density Oligonucleotide Arrays," *Nat. Biotechnol.*, 1996;14:1675-1680.

Lodie, T.A. et al., "Systematic Analysis of Reportedly Distinct Populations of Mulitpotent Bone Marrow-Derived Stem Cells Reveals a Lack of Distinction," *Tissue Engineering*, 2002; 8(5):739-751.

Luyten, F.P. et al., "Skeletal Tissue Engineering: Opportunities and Challenges," *Best Pract. Res. Clin. Rheumatol.*, 2001; 15(5):759-769.

Ma, L. et al., "Human Umbilical Cord Wharton's Jelly-Derived Mesenchymal Stem Cells Differentiation into Nerve-Like Cells," *Chinese Med. Jour.*, 2005; 118(23):1987-1993.

Mackay, A.M. et al., "Chondrogenic Differentiation of Cultured Human Mesenchymal Stem Cells From Marrow," *Tissue Engineering*, 1998; 4(4):415-428.

Makino, S. et al., "Cardiomyocytes can be generated from marrow stromal cells in vitro," *J. Clin. Invest.*, 1999; 103:697-705.

Marx, W.F. et al., "Endovascular Treatment of Experimental Aneurysms by Use of Biologically Modified Embolic Devices: Coil-Mediated Intraaneurysamal Delivery of Fibroblast Tissue Allografts," *Am. J. Neuroradiol.*, 2001; 22:323-333.

Mayer-Proschel, M. et al., "Isolation of Lineage-Restricted Neuronal Precursors From Multipotent Neuroepithelial Stem Cells," *Neuron.*, 1997; 19:773-785.

McAdams, T.A., et al., "Hematopoietic Cell Culture Therapies (Part I): Cell Culture Considerations," TibTech, 1996; 14:341-349.

Medicetty, S. et al., "Transplantation of Human Umbilical Cord Matrix Stem Cells Alleviates Apomorphine-Induced Rotations in Parkinsonian Rats", Society for Neuorscience, 2003; XP-002383776, Abstract (Presentation No. 300.14), 1 page.

Melero-Martin, J. et al., "Optimal In-Vitro Expansion of Chondroprogenitor Cells in Monolayer Culture," *Biotechnology and Bioengineering*, 2006; 93(3):519-533.

Messina, D.J., et al., "Comparison of Pure and Mixed Populations of Human Fetal-Derived Neural Progenitors Transplanted Into Intact Adult Rat Brain," *Exper. Neurol.*, 2003; 184:816-829.

Mitchell, K.E. et al., "Matrix Cells From Wharton's Jelly Form Neurons and Glia," *Stem Cells*, 2003; 21:50-60.

Mombaerts, P. et al., "Creation of a Large Genomic Deletion at the T-Cell Antigen Receptor β-Subunit Locus in Mouse Embryonic Stem Cells by Gene Targeting," *Proc. Nat. Acad. Sci. USA*, 1991; 88:3084-3087.

Naughton et al., "Cells isolated from Wharton's jelly of the human umbilical cord develop a cartilage phenotype when treated with TGF-b in vitro," 1997; FASEB J 11:A19 (Abstract 108).

Nicosia, R.F. et al., "Modulation of Microvascular Growth and Morphogenesis by Reconstituted Basement Membrane Gel in Three-Dimensional Cultures of Rat Aorta: A Comparative Study of Angiogenesis in Matrigal, Collagen, Fibrin, and Plasma Clot," *In Vitro Cell Dev. Biol.*, 1990; 26:119-128.

Oh, S.H. et al., "Hepatocyte Growth Factor Induces Differentiation of Adult Rat Bone Marrow Cells Into a Hepatocyte Lineage In Vitro," *Biochem. & Biophys. Res. Comm.*, 2000; 279:500-504.

Ornitz, D.M. et al., "Elastase I Promoter Directs Expression of Human Growth Hormone and SV40 T Antigen Genes to Pancreatic Acinar Cells in Transgenic Mice," *Cold Spring Harbor Symp. Quant. Biol.*, 1985; 50:399-409.

Pera, M.F. et al.,"Human Embryonic Stem Cells", *J. Cell Science*, 2000; 113:5-10.

Pesce, M. et al., "Myoendothelial Differentiation of Human Umbilical Cord Blood-Derived Stem Cells in Ischemic Limb Tissues," Circulation Research, 2003; 93:e51-e62.

Pilling, D. et al., "Identification of markers that distinguish monocyte-derived fibrocytes from monocytes, macrophages, and fibroblasts", PLoS One, 2009; 4(10):e7475.

Pittenger, M.F. et al., "Mesenchymal Stem Cells and Their Potential as Cardiac Therapeutics," *Circ. Res.*, 2004; 95:9-20.

(56) References Cited

OTHER PUBLICATIONS

Pittenger, M.F. et al., "Multilineage Potential of Adult Human Mesenchymal Stem Cells," *Science*, 1999; 284:143-47 and seven pages of online supplementary material.

Plaia, T., et al., "Characterization of a New NIH-Registered Variant Human Embryonic Stem Cell Line, BG01V: A Tool for Human Embryonic Stem Cell Research," *Stem Cells*, 2006: 24: 531-546.

Pountos, I. et al., "Mesenchymal Stem Cell Tissue Engineering: Techniques for Isolation, Expansion and Application," *Injury, Int. J. Care Injured*, 2007; 38:S23-S33.

Rahman, Z. et al., "Isolation and Primary Culture Urothelial Cells from Normal Human Bladder," *Urol. Research*, 1987; 15:315-320.

Rehman, J. et al., "Secretion of Angiogenic and Antiapoptotic Factors by Human Adipose Stromal Cells," *Circulation*, 2004; 109:1292-1298.

Reubinoff, B.E. et al., "Neural Progenitors From Human Embryonic Stem Cells," *Nature Biotechnology*, 2001; 19:1134-1140.

Reyes, M. et al., "Purification and Ex Vivo Expansion of Postnatal Human Marrow Mesodermal Progenitor Cells," *Blood*, 2001; 98(9):2615-2625.

Romanov, Y.A. et al., "Searching for Alternative Sources of Postnatal Human Mesenchymal Stem Cells: Candidate MSC-Like Cells from Umbilical Cord," *Stem Cells*, 2003; 21:105-110.

Rosen, E.M. et al., "HGF/SF in Angiogenesis," *Ciba Found. Symp.*, 1997; 212:215-229.

Russo, E., Cultivating Policy from Cell Types, *The Scientist*, 2001; 15(11):6 (printout is numbered 1-6).

Rutherford, A. et al., "Eyeing-Up Stem Cell Transplantation," *Trends in Molecular Medicine*, 2001; 7(1):11.

Safarik, I. et al., "Use of magnetic techniques for the isolation of cells," *J Chromatogr B Biomed Sci Appl.*, 1999; 722(1-2):33-53.

Sakariassen, K.S. et al., "Methods and Models to Evaluate Shear-Dependent and Surface Reactivity-Dependent Antithrombotic Efficacy," *Thromb. Res.*, 2001; 104:149-174.

Salcedo, R. et al., "Human Endothelial Cells Express CCR2 and Respond to MCP-1: Direct Role of MCP-1 in Angiogenesis and Tumor Progression," *Blood*, 2000; 96(1):34-40.

Sébire, G. et al., "In Vitro Production of IL-6, IL-1β, and Tumor Necrosis Factor-α by Human Embryonic Microglial and Neural Cells," *J. Immunol.*, 1993; 150(4):1517-1523.

Seiji, T. et al., "Possibility of Regenerative Medicine Using Human Amniotic Cells," *Regenerative Medicine*, 2002; 1(2):79-85 (with English language Abstract).

Sethe, S. et al., "Aging of Mesenchymal Stem Cells," *Ageing Research Reviews*, 2006; 5:91-116.

Somers, J. et al.,"Double Umbilical Cord Blood Transplantation Preceded by a Reduced-Intensity Conditioning Regimen: Rapid Induction of Single Donor Chimerism and Highly Predictive Value of Early CD4+ T Cell and NK Cell Predominance," *Blood* (*ASH Annual Meeting Abstracts*), 2011; 118:1303-1304 (Abstract 3026).

Sordillo, L.M. et al., "Culture of Bovine Mammary Epithelial Cells in D-Valine Modified Medium: Selective Removal of Contaminating Fibroblasts," *Cell Biol. Int. Rep.*, 1988; 12(5):354-365.

Sudo, K. et al., "Gene expression profiles of cryopreserved CD34(+) human umbilical cord blood cells are related to their bone marrow reconstitution abilities in mouse xenografts," *Biochem Biophys Res Commun.*, 2010; 397:697-705.

Tresco, P.A. et al., "Cellular Transplants As Sources for Therapeutic Agents," *Advanced Drug Delivery Reviews*, 2000; 42:3-27.

Turner, D., "The Human Leucocyte Antigen (HLA) System," *Vox Sang.*, 2004; 87(Suppl 1):S87-S90.

Tusher, V.G. et al., "Significance Analysis of Microarrays Applied to the Ionizing Radiation Response," *PNAS*, 2001; 98(9):5116-5121.

Ulloa-Montoya, F. et al., "Culture Systems for Pluripotent Stem Cells," *Journal of Bioscience and Bioengineering*, 2005; 100(1):12-27.

Wang, Y. et al., "Enhanced Recovery of Hematopoietic Progenitor and Stem Cells from Cultivated, Postpartum Human Placenta," *Blood*, 2001; 98(11): 183a (Abstract 769).

Watanabe, N. et al., "Recipient-derived cells after cord blood transplantation: dynamics elucidated by multicolor FACS, reflecting graft failure and relapse," *Biol Blood Marrow Transplant*, 2008; 14(6):693-701.

Weiss, M.L. et al., "Human Umbilical Cord Matrix Stem Cells: Preliminary Characterization and Effect of Transplantation in a Rodent Model of Parkinson's Disease," *Stem Cells*, 2006; 24:781-792.

Weiss, M.L. et al., "Transplantation of Porcine Umbilical Cord Matrix Cells Into the Rat Brain," *Exp. Neur.*, 2003; 182:288-299.

Wenning, G.K. et al., "Neural Transplantation in Animal Models of Multiple System Atrophy: A Review," *J. Neural Transm.*, 1999; Suppl.(55):103-113.

Ye Q. et al., "Recovery of Placental-Derived Adherent Cells With Mesenchymal Stem Cell Characteristics", *Blood*, 2001; 98(11 Part 2):147B (Abstract No. 4260).

Zhang, L-F. et al., "Telomeric RNAs Mark Sex Chromosomes in Stem Cells," *Genetics*, 2009; 182: 685-698.

Zimmerman, S. et al., "Lack of Telomerase Activity in Human Mesenchymal Stem Cells," *Leukemia*, 2003; 17:1146-1149.

| LABEL | Name | Cell Line |
|---|---|---|
| R52550 | Donor 1 PDL=11.80 | HUTC-DCB |
| R52551 | Donor 1 PDL=20.26 | Umb 041505 |
| R52552 | Donor 1 PDL=30.06 | Umb 041505 |
| R52553 | Donor 1 PDL=33.58 | Umb 041505 |
| R52554 | Donor 1 PDL=36.78 | Umb 041505 |
| R52555 | Donor 1 PDL=40.03 | Umb 041505 |
| R52556 | Donor 1 PDL=43.00 | Umb 041505 |
| R52557 | Donor 1 PDL=44.98 | Umb 041505 |
| R52559 | Donor 2 PDL=11.30 | Umb 072804A |
| R52560 | Donor 2 PDL=20.92 | Umb 072804A |
| R52561 | Donor 2 PDL=30.29 | Umb 072804A |
| R52562 | Donor 2 PDL=31.13 | Umb 072804A |
| R52563 | Donor 2 PDL=32.66 | Umb 072804A |
| R52564 | Donor 2 PDL=33.01 | Umb 072804A |
| R52565 | Donor 2 PDL=33.81 | Umb 072804A |
| R52558 | Donor 2 PDL=5.00 | Umb 072804A |
| R52567 | Donor 3 PDL=10.79 | Umb 083105 |
| R52568 | Donor 3 PDL=20.12 | Umb 083105 |
| R52569 | Donor 3 PDL=30.03 | Umb 083105 |
| R52570 | Donor 3 PDL=30.48 | Umb 083105 |
| R52571 | Donor 3 PDL=31.16 | Umb 083105 |
| R52572 | Donor 3 PDL=31.47 | Umb 083105 |
| R52573 | Donor 3 PDL=31.69 | Umb 083105 |
| R52566 | Donor 3 PDL=5.00 | Umb083105 |
| R52575 | Donor 4 PDL=10.71 | Umb 090304A |
| R52576 | Donor 4 PDL=14.66 | Umb 090304A |
| R52577 | Donor 4 PDL=19.55 | Umb 090304A |
| R52578 | Donor 4 PDL=25.06 | Umb 090304A |
| R52579 | Donor 4 PDL=27.25 | Umb 090304A |
| R52580 | Donor 4 PDL=28.60 | Umb 090304A |
| R52581 | Donor 4 PDL=30.15 | Umb 090304A |
| R52574 | Donor 4 PDL=5.00 | Umb 090304A |

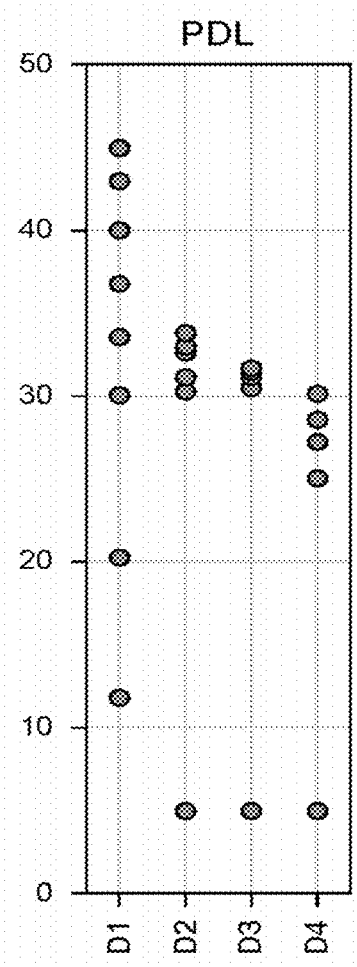

Fig. 1A  Fig. 1B

DETECTION OF HUMAN UMBILICAL CORD TISSUE-DERIVED CELLS

CROSS-REFERENCE TO RELATED APPLICATIONS

This application is a divisional application of Ser. No. 13/722,849 filed on Dec. 20, 2012 (now U.S. Pat. No. 9,611,513, issued Apr. 4, 2017), which claims priority to U.S. Provisional Application 61/579,710 filed on Dec. 23, 2011, the contents of which are incorporated by reference in their entirety.

FIELD OF THE INVENTION

The invention relates to methods of detecting allogeneic therapeutic cells, such as e.g. human umbilical cord tissue-derived cells, in a sample from a patient that treated with the therapeutic cells.

BACKGROUND OF THE INVENTION

Allogeneic cell therapies are a promising new technology for the treatment of a number of unmet medical needs. However, cell therapies are unique products and pose some unique challenges in the development process. One specific example of this technology is the development of human umbilical cord tissue-derived cells ("hUTC") for a number of clinical indications. Following administration of hUTC to subjects, measuring the presence and/or the number of cells detected in the subject's blood is desirable information relevant to the pharmacokinetics of hUTC as a cell therapy product. However, this poses a challenge since hUTC may have characteristics that are similar to cells gathered from the blood of the subject. Therefore, it is necessary to distinguish hUTC from other cells.

Clinical studies during drug development include pharmacokinetic studies to examine parameters of absorption, distribution, metabolism, and excretion of the drug in vivo. An important element of the pharmacokinetic studies is to determine the level of exposure of a drug in subjects. Typically, this is done through analysis of drug levels from blood samples; exposure levels are evaluated relative to efficacy and safety outcomes. In the case of a cell therapy product, such as hUTC, studying the bio-distribution or pharmacokinetics of hUTC in clinical trials presents a challenge because there is no established method to distinguish hUTC (or other cell products) from the subjects' own cells. Therefore, it is difficult to determine the bioavailability of hUTC.

Presently accepted approach for determining if allogeneic therapeutic cells (e.g. hUTC) are present in the circulation requires the use of allogeneic therapeutic cells (e.g. hUTC) from a male donor and intravenous transfusion into female subjects. See e.g. Bader P. et al., "How and when should we monitor chimerism after allogeneic stem cell transplantation?" *Bone Marrow Transplantation,* 2005; 35: 107-119; see also Durnman, D M et al., "Analysis of the origin of marrow cells in bone marrow transplant recipients using a Y-chromosome-specific in situ hybridization assay," *Blood,* 1989; 74: 2220-2226. Real time PCR is used to detect the Y chromosome in a sample of the subject's blood and the results provide a relative quantification or binary signal to indicate the presence or absence of allogeneic therapeutic cells (e.g. hUTC) in the blood sample. See Brader P. et al. This approach necessitates excluding female cell (e.g. hUTC) donors and male subjects from analyses on pharmacokinetics of hUTC in clinical studies. Therefore, there remains a need for a method for detecting allogeneic cells, such as e.g. UTC, in patients after administration of the cells.

SUMMARY OF THE INVENTION

The invention provides for detecting the presence of allogeneic therapeutic cells in a sample of human peripheral blood mononuclear cells. The invention allows for the detection of such therapeutic cells without being constrained by the therapeutic cells karyotype (XY vs. XX) and recipient (patient) gender.

One embodiment of the invention is a method of detecting allogeneic therapeutic cells in blood comprising: (a) assaying allogeneic therapeutic cells and human peripheral blood mononuclear cells to identify one or more markers positive for allogeneic therapeutic cells and one or more markers positive for patient peripheral blood mononuclear cells; (b) providing a blood sample from a patient that has been treated with allogeneic therapeutic cells; (c) analyzing the sample using an assay method to detect one or more markers positive for patient peripheral blood mononuclear cells and one or more markers positive for allogeneic therapeutic cells; and (d) distinguishing between the patient peripheral blood mononuclear cells and allogeneic therapeutic cells based on the detection of one or more markers positive for patient peripheral blood mononuclear cells and one or more markers positive for allogeneic therapeutic cells. In one embodiment, the one or more positive markers for patient peripheral blood mononuclear cells comprises CD45. Alternatively, the method for detecting allogeneic therapeutic cells in blood includes: (a) assaying allogeneic therapeutic cells and human peripheral blood mononuclear cells to identify one or more markers positive for allogeneic therapeutic cells and one or more markers positive for patient peripheral blood mononuclear cells; (b) comparing the one or more markers positive for allogeneic therapeutic cells and the one or more markers positive for patient peripheral blood mononuclear cells to identify one or more unique markers which distinguishes the allogeneic therapeutic cells from the patient peripheral blood mononuclear cells; (c) providing a blood sample from a patient that has been treated with allogeneic therapeutic cells; (d)analyzing the sample using an assay method to detect the one or more unique markers positive for the allogeneic therapeutic cells; and (e) distinguishing between the patient peripheral blood mononuclear cells and allogeneic therapeutic cells based on the detection of the one or more unique markers.

The methods may be suitable to detect any allogeneic therapeutic cells of interest. For example, the allogeneic therapeutic cells may be selected from the group consisting of human umbilical cord tissue-derived cells, human umbilical cord blood-derived cells, placental-derived cells, mesenchymal stem cell derived cells, liver cells, pancreatic islet cells, cardiomyocytes, and insoluble collagenous bone matrix cells. The methods may also be used to detect two or more different types of allogeneic therapeutic cells in a blood sample.

A variety of different assay methods may be used for these methods, such as e.g. flow cytometry, ELISA, immunohistochemistry, nucleic acid detection, PCR, and combinations thereof. Additionally, the methods may include an enrichment step between steps (a) and (b). The enrichment step may include magnetic capture technology. The step of distinguishing includes differentiating between allogeneic therapeutic cells administered to the patient and peripheral blood mononuclear cells from the patient. The patient may be a human, non-human primate, mouse, rat, hamster, guinea pig, dog, or pig.

The invention also provides for kits, which may be used use in the method of detecting allogeneic therapeutic cells in a blood sample. The kits may include a marker profile having one or more markers positive allogeneic therapeutic cells and one or more markers positive for patient peripheral blood mononuclear cells.

Another embodiment of the invention is a method of detecting human umbilical cord tissue-derived cells in blood including: (a) assaying human umbilical cord tissue-derived cells and human peripheral blood mononuclear cells to identify one or more markers positive for human umbilical cord tissue-derived cells and one or more markers positive for human peripheral blood mononuclear cells; (b) providing a blood sample from a patient that has been treated with human umbilical cord tissue-derived cells; (c) analyzing the sample using an assay method to detect one or more markers positive for patient peripheral blood mononuclear cells and one or more markers positive for human umbilical cord tissue-derived cells; and (d) distinguishing between the patient peripheral blood mononuclear cells and human umbilical cord tissue-derived cells based on the detection of one or more markers positive for patient peripheral blood mononuclear cells and one or more markers positive for human umbilical cord tissue-derived cells. Alternatively, the method of detecting human umbilical cord tissue-derived cells in blood includes: (a) assaying human umbilical cord tissue-derived cells and human peripheral blood mononuclear cells to identify one or more markers positive for human umbilical cord tissue-derived cells and one or more markers positive for patient peripheral blood mononuclear cells; (b) comparing the one or more markers positive for human umbilical cord tissue-derived cells and the one or more markers positive for human peripheral blood mononuclear cells to identify one or more unique markers which distinguishes the umbilical cord tissue-derived cells from the patient peripheral blood mononuclear cells; (c) providing a blood sample from a patient that has been treated with human umbilical cord tissue-derived cells; (d) analyzing the sample using an assay method to detect one or more unique markers positive for human umbilical cord tissue-derived cells; and (e) distinguishing between the patient peripheral blood mononuclear cells and human umbilical cord tissue-derived cells based on the detection of the one or more unique markers. The patient may be a human, non-human primate, mouse, rat, hamster, guinea pig, dog, or pig.

In one embodiment, the positive marker for patient peripheral blood mononuclear cells is CD45 and the positive marker for human umbilical cord tissue-derived cells is CD10. In another embodiment, markers for patient peripheral blood mononuclear cells and for human umbilical cord tissue-derived cells include one or more of CD10, CD13, NRP1, CD45, LAMP1, DKK3, NRP1, or LAMB1. The method may employ a variety of assay techniques including flow cytometry, ELISA, immunohistochemistry, nucleic acid detection, PCR, and combinations thereof. The one or more unique markers positive for human umbilical cord tissue-derived cells may be one or more of CD10, CD13, NRP1, LAMP1, DKK3, NRP1, LAMB1 and combinations thereof.

The method may further comprise performing an enrichment step between steps (a) and (b). The enrichment step may be magnetic capture technology. Another embodiment of the invention is a kit for use in the method of detecting human umbilical cord tissue-derived cells in blood comprising a marker profile having one or more markers positive for human umbilical cord tissue-derived cells and one or more markers positive for human peripheral blood mononuclear cells. The invention also provides for systems for use with the methods of the invention.

Another embodiment of the invention is a method of detecting human umbilical cord tissue-derived cells in blood including the steps of: assaying human umbilical cord tissue-derived cells and human peripheral blood mononuclear cells to identify one or more markers positive for human umbilical cord tissue-derived cells and one or more markers positive for human peripheral blood mononuclear cells; providing a blood sample containing human umbilical cord tissue-derived cells; isolating the human umbilical cord tissue-derived cell/peripheral blood mononuclear cell fraction from the blood sample; analyzing the human umbilical cord tissue-derived cell/peripheral blood mononuclear cell fraction by flow cytometry for CD45 as a positive marker for peripheral blood mononuclear cell and CD10 or CD13 as a positive marker for human umbilical cord tissue-derived cells and detecting the presence of the human peripheral blood mononuclear cells and human umbilical cord tissue-derived cells based on the detection of CD45 as a marker positive for human peripheral blood mononuclear cells and CD10 or CD13 as a marker positive for human umbilical cord tissue-derived cells.

The step of analyzing may include analysis of the human umbilical cord tissue-derived cell/peripheral blood mononuclear cell fraction by flow cytometry for CD45 as a positive marker for peripheral blood mononuclear cell and CD13 as a positive marker for human umbilical cord tissue-derived cells. Alternatively the step of analysis may include analysis of the human umbilical cord tissue-derived cell/peripheral blood mononuclear cell fraction by flow cytometry for CD45 as a positive marker for peripheral blood mononuclear cell and CD10 as a positive marker for human umbilical cord tissue-derived cells. The method may also further include performing an enrichment step prior to analyzing the human umbilical cord tissue-derived cell/peripheral blood mononuclear cell fraction such as e.g. magnetic capture technology.

Another embodiment of the invention is a method of detecting human umbilical cord tissue-derived cells in blood including the steps of: providing a blood sample containing human umbilical cord tissue-derived cells; isolating the human umbilical cord tissue-derived cell/peripheral blood mononuclear cell fraction from the blood sample; removing any plasma; analyzing the human umbilical cord tissue-derived cell/peripheral blood mononuclear cell fraction by flow cytometry for CD45 as a positive marker for peripheral blood mononuclear cell and CD13 as a positive marker for human umbilical cord tissue-derived cells and detecting the presence of the human peripheral blood mononuclear cells and human umbilical cord tissue-derived cells based on the detection of CD45 as a marker positive for human peripheral blood mononuclear cells and CD13 as a marker positive for human umbilical cord tissue-derived cells. The method may also further include performing an enrichment step prior to analyzing the human umbilical cord tissue-derived cell/peripheral blood mononuclear cell fraction such as e.g. magnetic capture technology. The method may also further include detecting for CD10 as a marker positive for human umbilical cord tissue-derived cells.

Human umbilical cord tissue-derived cells are isolated from human umbilical cord tissue substantially free of blood, are capable of self-renewal and expansion in culture, and have the potential to differentiate. In one embodiment, the human umbilical cord tissue-derived cells are isolated from human umbilical cord tissue substantially free of blood, are capable of self-renewal and expansion in culture, have the potential to differentiate, and have the following characteristics: (1) express CD10, CD13, CD44, CD90, and HLA-ABC; (2) do not express CD31, CD34, CD45, HLA-DR and CD117, and (3) do not express hTERT or telomerase. Alternatively, the human umbilical cord tissue-derived cells may be isolated from human umbilical cord tissue substantially free of blood, are capable of self-renewal and expansion in culture, have the potential to differentiate, and have the following characteristics: (1) express CD10, CD13, CD44, CD90, and HLA-ABC; (2) do not express CD31, CD34, CD45, HLA-DR and CD117; (3) do not express hTERT or telomerase; (4) express oxidized low density lipoprotein receptor 1, reticulon, chemokine receptor ligand 3, and/or granulocyte chemotactic protein; and (4) express, relative to a human fibroblast, mesenchymal stem cell, or iliac crest bone marrow cell, increased levels of interleukin 8 or reticulon 1.

Another embodiment of the invention is method of detecting human umbilical cord tissue-derived cells in blood including the steps of: (a) providing a blood sample from a patient that has been treated with human umbilical cord tissue-derived cells; (b) analyzing the sample using an assay method to detect one or more markers positive for human peripheral blood mononuclear cells and one or more markers positive for human umbilical cord tissue-derived cells; and (c) distinguishing between the human peripheral blood mononuclear cells and one or more markers positive for human umbilical cord tissue-derived cells. In one embodiment, the positive marker for human peripheral blood mononuclear cells is CD45 and the positive marker for human umbilical cord tissue-derived cells is CD10. The step of analyzing may utilize flow cytometry, ELISA, immunohistochemistry, nucleic acid detection, and/or PCR. The method may further include the performing an enrichment step between steps (a) and (b). The enrichment step may be magnetic capture technology.

Yet another embodiment of the invention is a method of detecting human umbilical cord tissue-derived cells in blood including the steps of: (a) providing a blood sample containing human umbilical cord tissue-derived cells; (b) isolating the human umbilical cord tissue-derived cell/peripheral blood mononuclear cell fraction from the blood sample; and (c) analyzing the human umbilical cord tissue-derived cell/peripheral blood mononuclear cell fraction by flow cytometry for CD45 as a positive marker for peripheral blood mononuclear cell and CD10 as a positive marker for human umbilical cord tissue-derived cells.

An alternate embodiment of the invention is a method of detecting human umbilical cord tissue-derived cells in blood comprising the steps of: providing a blood sample containing human umbilical cord tissue-derived cells; isolating the human umbilical cord tissue-derived cell/peripheral blood mononuclear cell fraction from the blood sample; removing any plasma; and analyzing the human umbilical cord tissue-derived cell/peripheral blood mononuclear cell fraction by flow cytometry for CD45 as a positive marker for peripheral blood mononuclear cell and CD13 as a positive marker for human umbilical cord tissue-derived cells.

Other features and advantages of the invention will be apparent from the detailed description and examples that follow.

BRIEF DESCRIPTION OF THE DRAWINGS

The foregoing summary, as well as the following detailed description of the invention, will be better understood when read in conjunction with the appended figures. For the purpose of illustrating the invention, the figures demonstrate embodiments of the present invention. It should be understood, however, that the invention is not limited to the precise arrangements, examples, and instrumentalities shown.

FIG. 1A and FIG. 1B list the 24 samples and the age of the cell culture for each sample used for Study 1 in Example 1. In particular, the Table at FIG. 1A lists the 24 samples used for microarray analysis and the chart at FIG. 1B shows the age of the cell culture for each of these 24 samples.

With reference to FIG. 4A, panes A1, B1, C1, D1, and E1 show the unstained controls. Pane A2 shows CD13 and 7AAD. Pane B2 shows CD10 and 7AAD. Pane C2 shows NRP1 and 7AAD. Pane D2 shows CD45 and 7AAD. Pane E2 shows LAMP1 and 7AAD.

With reference to FIG. 4B, panes A1, B1, C1, D1, and E1 show the unstained controls. Pane A2 shows CD13 and 7AAD. Pane B2 shows CD10 and 7AAD. Pane C2 shows NRP1 and 7AAD. Pane D2 shows CD45 and 7AAD. Pane E2 shows LAMP1 and 7AAD.

DETAILED DESCRIPTION

Figure 2A:
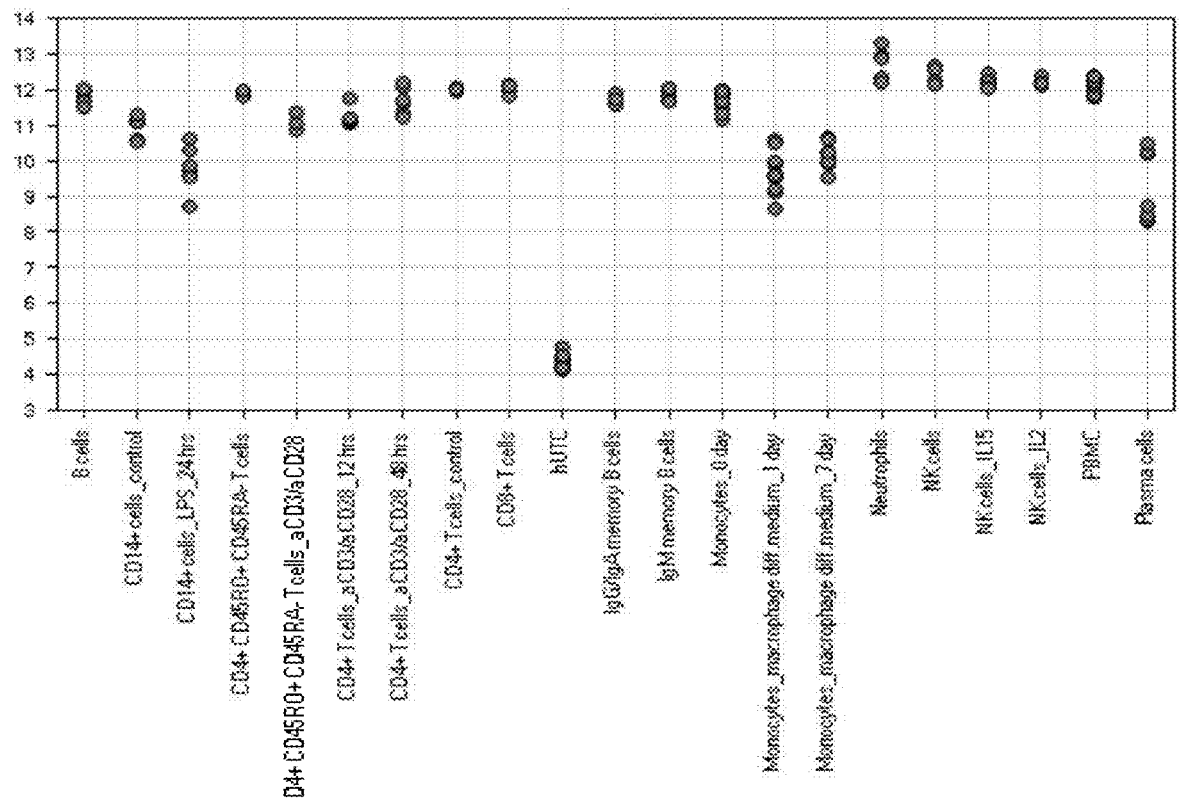
FIG. 2A shows a comparative expression of PTPRC (CD45) gene in human umbilical cord tissue-derived cells (hUTC) and in various types of blood cells that comprise of human PBMC.

This application is directed to methods of detecting allogeneic therapeutic cells such as progenitor cells circulating in the blood of a patient (e.g. human). Progenitor cells or other engineered cells, which are components of a cell therapy product, are being developed for a number of clinical indications. These cells, such as e.g. hUTC, are administered to the patient via e.g. intravenous administration. The disposition of these cells in circulating blood needs to be determined in order to assess the pharmacokinetics of the cells as a cell therapy product and also to more accurately determine success of the therapy. However, human blood is composed of multiple types of blood cells, one or more type of which express some proteins that may also be expressed in the progenitor or engineered cells. Moreover, it is important to develop a sufficiently sensitive assay that can detect a small number of these cells (such as e.g. hUTC) in a large excess of cells in the recipient's blood. Detecting these cells in the presence of human blood, therefore, becomes a challenge that requires obtaining sufficient sensitivity and specificity. Thus, there is a need for an assay that can identify and distinguish progenitor or engineered cells from human blood cells.

I. Definitions

A "sample" as used herein, refers to any substance, which may contain the analyte of interest. A sample can be biological fluid, such as whole blood or whole blood components including red blood cells, white blood cells, platelets, serum and plasma, ascetic fluid, urine, cerebrospinal fluid, and other constituents of the body.

The cells which may be identified in a blood sample containing peripheral mononuclear cells using the methods of the invention are generally referred to as postpartum cells or postpartum-derived cells (PPDCs). The cells are more specifically "umbilicus-derived cells" or "umbilical cord-derived cells" (UDC), or "umbilical cord tissue-derived cells" (UTC) or "human umbilical cord tissue-derived cells" (hUTC). In addition, the cells may be described as being stem or progenitor cells, the latter term being used in the broad sense. The term "derived" is used to indicate that the cells have been obtained from their biological source and grown or otherwise manipulated in vitro (e.g., cultured in a growth medium to expand the population and/or to produce a cell line). The in vitro manipulations of umbilical stem cells and the unique features of the umbilicus-derived cells of the present invention are described in detail below.

Stem cells are undifferentiated cells defined by the ability of a single cell both to self-renew and to differentiate to produce progeny cells, including self-renewing progenitors, non-renewing progenitors, and terminally differentiated cells. Stem cells are also characterized by their ability to differentiate in vitro into functional cells of various cell lineages from multiple germ layers (endoderm, mesoderm and ectoderm), as well as to give rise to tissues of multiple germ layers following transplantation, and to contribute substantially to most, if not all, tissues following injection into blastocysts.

Stem cells are classified according to their developmental potential as: (1) totipotent; (2) pluripotent; (3) multipotent; (4) oligopotent; and (5) unipotent. Totipotent cells are able to give rise to all embryonic and extraembryonic cell types. Pluripotent cells are able to give rise to all embryonic cell types. Multipotent cells include those able to give rise to a subset of cell lineages, but all within a particular tissue, organ, or physiological system. For example, hematopoietic stem cells (HSC) can produce progeny that include HSC (self-renewal), blood cell-restricted oligopotent progenitors, and all cell types and elements (e.g., platelets) that are normal components of the blood. Cells that are oligopotent can give rise to a more restricted subset of cell lineages than multipotent stem cells. Cells that are unipotent are able to give rise to a single cell lineage (e.g., spermatogenic stem cells).

Stem cells are also categorized based on the source from which they are obtained. An adult stem cell is generally a multipotent undifferentiated cell found in tissue comprising multiple differentiated cell types. The adult stem cell can renew itself. Under normal circumstances, it can also differentiate to yield the specialized cell types of the tissue from which it originated, and possibly other tissue types. An embryonic stem cell is a pluripotent cell from the inner cell mass of a blastocyst-stage embryo. A fetal stem cell is one that originates from fetal tissues or membranes. A postpartum stem cell is a multipotent or pluripotent cell that originates substantially from extraembryonic tissue available after birth, namely, the umbilical cord. These cells have been found to possess features characteristic of pluripotent stem cells, including rapid proliferation and the potential for differentiation into many cell lineages. Postpartum stem cells may be blood-derived (e.g., as are those obtained from umbilical cord blood) or non-blood-derived (e.g., as obtained from the non-blood tissues of the umbilical cord).

Various terms are used to describe cells in culture. "Cell culture" refers generally to cells taken from a living organism and grown under controlled conditions ("in culture" or "cultured"). A "primary cell culture" is a culture of cells, tissues, or organs taken directly from an organism(s) before the first subculture. Cells are "expanded" in culture when they are placed in a growth medium under conditions that facilitate cell growth and/or division, resulting in a larger population of the cells. When cells are expanded in culture, the rate of cell proliferation is sometimes measured by the amount of time needed for the cells to double in number. This is referred to as "doubling time."

The term "cell line" generally refers to a population of cells formed by one or more subcultivations of a primary cell culture. Each round of subculturing is referred to as a passage. When cells are subcultured, they are referred to as having been "passaged." A specific population of cells, or a cell line, is sometimes referred to or characterized by the number of times it has been passaged. For example, a cultured cell population that has been passaged ten times may be referred to as a P10 culture. The primary culture, i.e., the first culture following the isolation of cells from tissue, is designated P0. Following the first subculture, the cells are described as a secondary culture (P1 or passage 1). After the second subculture, the cells become a tertiary culture (P2 or passage 2), and so on. It will be understood by those of skill in the art that there may be many population doublings during the period of passaging; therefore, the number of population doublings of a culture is greater than the passage number. The expansion of cells (i.e., the number of population doublings) during the period between passaging depends on many factors, including, but not limited to, the seeding density, substrate, medium, growth conditions, and time between passaging.

"Differentiation" is the process by which an unspecialized ("uncommitted") or less specialized cell acquires the features of a specialized cell, such as e.g. a nerve cell or a muscle cell. A "differentiated" cell is one that has taken on a more specialized ("committed") position within the lineage of a cell. The term "committed", when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. "De-differentiation" refers to the process by which a cell reverts to a less specialized (or committed) position within the lineage of a cell. As used herein, the "lineage" of a cell defines the heredity of the cell, i.e., which cells it came from and what cells it can give rise to. The lineage of a cell places the cell within a hereditary scheme of development and differentiation.

In a broad sense, a "progenitor cell" is a cell that has the capacity to create progeny that are more differentiated than itself, and yet retains the capacity to replenish the pool of progenitors. By that definition, stem cells themselves are also progenitor cells, as are the more immediate precursors to terminally differentiated cells. When referring to the cells of the present invention, as described in more detail below, this broad definition of progenitor cell may be used. In a narrower sense, a progenitor cell is often defined as a cell that is intermediate in the differentiation pathway, i.e., it arises from a stem cell and is intermediate in the production of a mature cell type or subset of cell types. This type of progenitor cell is generally not able to self-renew. Accordingly, if this type of cell is referred to herein, it will be referred to as a "non-renewing progenitor cell" or as an "intermediate progenitor or precursor cell."

Generally, a "trophic factor" is defined as a substance that promotes survival, growth, proliferation, and/or maturation of a cell, or stimulates increased activity of a cell.

The term "standard growth conditions," as used herein refers to culturing of cells at 37° C., in a standard atmosphere comprising 5% $CO_2$ and relative humidity maintained at about 100%. While the foregoing conditions are useful for culturing, it is to be understood that such conditions are capable of being varied by the skilled artisan who will appreciate the options available in the art for culturing cells.

The term "isolate" as used herein generally refers to a cell, which has been separated from its natural environment. This term includes gross physical separation from its natural environment, e.g., removal from the donor animal. In preferred embodiments, an isolated cell is not present in a tissue, i.e., the cell is separated or dissociated from the neighboring cells with which it is normally in contact. Preferably, cells are administered as a cell suspension. As used herein, the phrase "cell suspension" includes cells which are in contact with a medium and which have been dissociated, e.g., by subjecting a piece of tissue to gentle trituration.

As used herein, the term peripheral blood mononuclear cell ("PBMC") encompasses any blood cell having a round nucleus. Exemplary peripheral blood mononuclear cells include but are not limited to lymphocytes, monocytes, and macrophages.

II. Methods of Detecting Allogeneic Therapeutic Cells in a Patient Blood Sample This application provides for methods of detecting allogeneic therapeutic cells in a patient's blood sample after the cells have been administered to the patient. The methods involve the steps of (a) providing a blood sample from a patient that has been treated with the allogeneic therapeutic cells; (b) analyzing the sample using an assay method to detect one or more markers positive for patient peripheral blood mononuclear cells ("PBMC") (e.g. any blood cell having a round nucleus) and/or one or more markers positive for therapeutics cells; and (c) distinguishing between the human peripheral blood mononuclear cells and one or more markers positive for allogeneic therapeutic cells that are not expressed by the peripheral blood mononuclear cells. To be able to distinguish between the markers for patient peripheral blood mononuclear cells and one or more markers positive for therapeutics cells that are not expressed by the peripheral blood mononuclear cells, one needs to also first identify these markers. Thus, the methods may further include the step of assaying for these markers. The methods of the invention allow detection of such cells without being limited by the karyotype of the allogeneic therapeutic cell (i.e. XX vs. XY) and the gender of the patient. Thus, the methods are not constrained by gender nor are they limited to only identifying male allogeneic therapeutic cells (XX) in a female patient.

In one embodiment, the invention provides methods for detecting or identifying human umbilical cord tissue-derived cells in a blood sample. The methods involve the steps of: (a) providing a blood sample from a patient that has been treated with human umbilical cord tissue-derived cells; (b) analyzing the sample using an assay method to detect one or more markers positive for human peripheral blood mononuclear cells and one or more markers positive for human umbilical cord tissue-derived cells; and (c) distinguishing between the human peripheral blood mononuclear cells and the human umbilical cord tissue-derived cells. To able to distinguish, one also needs to assay for the unique marker profile to be able to select the distinguishing unique marker profile. A further step of quantifying the amount of hUTC may also be employed. In one embodiment, the markers shown in Example 3 may be used.

In another embodiment, the invention describes methods to distinguish and/or measure an hUTC cell therapy product following intravenous administration in humans. The methods identify molecular markers that are expressed at substantially higher levels in hUTC as compared to cells normally present in blood, i.e., peripheral blood mononuclear cells ("PBMC"). Since the methods rely on a unique marker profile for the identification of hUTC, they allow detection of such cells without being limited by karyotype of the hUTC (XX vs. XY) and the gender of the patient. They are not constrained by gender nor are they limited to only male hUTC. Thus, these methods permit analysis of both male and female hUTC in both male and female subjects, in any combination.

The methods of the invention are suitable to distinguish allogeneic therapeutic cells in the blood of a patient from a variety of sources. In particular, the methods of the invention are suitable for detecting a small number of hUTC in the presence of a large excess of a recipient's blood. This method is applicable for any member of the mammalian system and is not restricted to that derived from humans. For example, the methods of the invention may be used to distinguish allogeneic therapeutic cells such as e.g. hUTC from PBMC in a human. Alternatively, the methods may be used to distinguish allogeneic therapeutic cells such as e.g. hUTC from PBMC in a non-human primate, mouse, rat, hamster, guinea pig, dog, or pig.

These methods help differentiate hUTC and other allogeneic therapeutic cells from the PBMC and may help monitor pharmacokinetics in subjects who receive a cell therapy product.

The methods of the invention are suitable for detection of allogeneic therapeutic cells (such as e.g. hUTC) in blood samples from patients having been treated with the cells. Thus, the methods of the invention are suitable for detection of allogeneic therapeutic cells (such as e.g. hUTC) that may have been previously administered. The methods of the invention may be suitable for the detection of any cell of therapeutic interest such as e.g. human cord blood-derived cells, placenta-derived cells, mesenchymal stem cells and mesenchymal stem cell-derived cells, hUTC, cardiomyocytes etc. or any targeted cells expressing a specific protein or proteins of interest. Other suitable cells for use in these methods include liver cells, pancreatic islet cells, fibroblasts and insoluble collagenous bone matrix-derived (ICBM) cells.

The methods may also be suitable for detection of two or more kinds of allogeneic therapeutic cells (such as e.g.

hUTC) in blood samples from patients having been treated with the cells. For example, the methods may be used to detect both human umbilical cord tissue-derived cells and placenta-derived cells in a blood sample. Alternatively, the methods can be used to detect human umbilical cord tissue-derived cells and dermal fibroblasts in a blood sample. The methods may also be used to detect human umbilical cord tissue-derived cells, placenta-derived cells, and dermal fibroblasts in a blood sample.

A. Identification of a Distinguishing Unique Marker Profile

The methods of the invention include the step of identifying a distinguishing unique marker profile based on the presence of the therapeutic cell (such as e.g. a human umbilical cord tissue-derived cells) in a patient blood sample containing PBMC.

To derive this unique marker profile, the expression of genes and presence of cell surface markers needs to be compared between the cells (e.g. human umbilical cord tissue-derived cells) and PBMC. Multiple technologies including protein-based technologies such as ELISA and immune-histochemistry or nucleic acid based technologies such as in situ hybridization may be used to detect the presence of hUTC in blood. Alternatively, PCR technology may be also used. As outlined in the Examples below, the expression level of various genes in PBMC and/or the allogeneic therapeutic cells may also be obtained from publically available sources.

Based on the expression level of these various genes, certain unique marker genes may be identified. In one embodiment, particularly suitable for rapid screening, the marker is a cell surface marker.

As illustrated in the examples below, molecular markers on hUTC may be identified by comparing the expression profile of these cells to that of human peripheral blood mononuclear cells (PBMC). By comparing expression profiles of hUTC and PBMC markers that are expressed at substantially higher levels in hUTC compared to cells normally present in the circulation and vice versa are thus identified for each patient. The markers identified include CD45, CD13, and CD10. As both hUTC and circulating cells can show dynamic expression levels, the method relies on multiple markers that can distinguish hUTCs from cells in the recipient's circulation.

The unique marker profile may include one or more markers positive for the allogeneic cells, the presence of which is being assayed, and one or more markers positive for the peripheral blood mononuclear cells. Thus, when assaying for human umbilical cord tissue-derived cells, the marker profile may include one or more markers positive for hUTC and one or more markers positive for peripheral blood mononuclear cells. Alternatively, the allogeneic cells, the presence of which is being assayed, may be identified using only one or more unique markers for the allogeneic cells sufficient to distinguish these cells from the peripheral blood mononuclear cells.

In one embodiment, particularly useful for identifying hUTC in PBMC, the unique marker profile includes one or more of CD10, CD13, NRP1, CD45, LAMP1, DKK3, NRP1, or LAMB1. In one embodiment, the unique marker profile comprises at least one or more marker characteristic (e.g. positive) for the hUTC and at least one marker characteristic (e.g. positive) for PBMC (such as e.g. CD45).

In another embodiment, also particularly useful for identifying hUTC in PBMC, the unique marker profiles includes one or more unique markers that are positive for the hUTC and that are sufficient to distinguish hUTC from the peripheral blood mononuclear cells. These one or more unique markers may include one or more of CD10, CD13, NRP1, LAMP1, DKK3, NRP1, or LAMB1.

Those of skill will recognize that the choice of which marker to use may vary depending on which technique is used. For example, using a microarray analysis (such as e.g. Affymetrix GeneChip® HT HG-U133+ PM array), ANPEP (CD13), LAMP1 and LAMB1 may be insufficient to distinguish while one or more of the others markers may be sufficient to distinguish. Similarly, using RT-PCT, LAMP1 may not be suitable as part of the unique marker profile that distinguishes hUTC from PBMC, while one or more of the other markers may be sufficient. In one embodiment, the unique marker profile used for screening for hUTC by cell surface flow cytometry does not include DKK3 and LAMB1. In another embodiment, the unique marker profile for intracellular cytometry includes LAMP1 and DKK3.

Exemplary suitable markers for identifying hUTC in a PBMC sample, using selected techniques are shown below.

| Technique | Markers only positive for hUTC using technique | Markers only positive for PBMC using technique |
|---|---|---|
| Microarray analysis | MME (CD10), NRP1, DKK3 | PTPRC (CD45) |
| RT-PCR | MME (CD10), NRP1, DKK3, LAMB1 | PTPRC (CD45) |
| Flow cytometry (surface) | MME (CD10), ANPEP (CD13) | PTPRC (CD45) |
| Flow cytometry (intracellular) | LAMP1 | |

Thus, in one embodiment, the unique marker profile includes CD10 as the one or more markers positive hUTC and CD45 as the one or more markers positive for PBMC. In another embodiment, the unique marker profile includes CD10 and/or CD13 as the one or more markers positive hUTC and CD45 as the one or more markers positive for PBMC.

In another embodiment, using flow cytometry as the assay method, the unique marker profile for identifying hUTC in PBMC includes CD45 as the one or more markers positive for peripheral blood mononuclear cell and CD10 as one or more markers positive for human umbilical cord tissue-derived cells.

In another embodiment of the invention, the maker profile to distinguish hUTC and PBMC comprises CD45, CD10, and CD13 using flow cytometry, wherein CD10 and CD13 are the one or more markers positive for hUTC and wherein CD45 is the one or more markers positive for PBMC.

Exemplary suitable markers for the identifying selected therapeutic cells in a PBMC sample are shown below:

| Type of cell | Marker for cell type | Marker for host PBMC |
|---|---|---|
| Human umbilical cord-blood derived | CD10, CD13, CD107a | CD45 |
| Placenta derived | Renin | Heat shock 27 kd |
| Mesenchymal stem cell derived | IL26, a-glucosidase | CD45 |
| Liver | FOXa2, HNFa1 | CD45 |
| Pancreatic islet cells | G6PC2, INSULIN | CD45 |
| Fibroblast | SDF-1, GCP-2 | CD45 |
| Human umbilical cord-blood derived and placenta-derived cells and dermal fibroblasts | IL8, GCP-2 | CD45 |

| Type of cell | Marker for cell type | Marker for host PBMC |
| --- | --- | --- |
| Human umbilical cord-blood derived and placenta-derived cells | IL6, MCP-1 | CD45 |
| Insoluble collagenous bone matrix (ICBM) | Integrin a-10; cardiac ankyrin repeat protein | CD45 |
| Cardiomyocytes | FoxA2, GATA4, MIR20 | CD45 |

The unique marker profile is obtainable using the following procedures as well the methodology described in the examples. The procedures describe below may encompass both obtaining the unique marker profile and verifying its accuracy. While the step of verification may encompass analysis of a sample, the step may be necessary to determine the accuracy and testing limits of the specific procedure by which the unique marker gene or protein will be detected. In this embodiment, flow cytometry may be used to identify the markers.

Obtaining the Unique Marker Profile.

The gene expression profile of hUTC, sourced from multiple sources, was generated using an Affymetrix GeneChip® HT HG-U133+ PM. The gene expression profiles of human and rat PBMC and other types of blood cells were obtained from publicly available databases. From the results of the gene expression profiles, a set of markers that are highly expressed in hUTC and a set of markers that are highly expressed in human PBMC can be identified. Sixty-one (61) genes were thus identified, a subset of which were studied in more detail. From this list of 61 genes, CD45 was identified as a positive marker for hPBMC and CD10 and CD13 as two positive markers for hUTC.

Verifying the Testing Methodology for the Marker Profile.

Since the number of hUTC in a sample of a subject's blood is anticipated to be low, it was determined whether a small number of hUTC in the presence of a large excess of human PBMC using the above-identified markers could be detected and quantified. For this purpose, known quantities of hUTC were spiked into approximately one million PBMC in 1 ml of human serum. Subsequently, an aliquot of each sample was analyzed by flow cytometry for CD45 as a positive marker for hPBMC and CD10 or CD13 as positive markers for hUTC. The cells were harvested by centrifugation, washed once with PBS and then fixed and permeabilized. Aliquots of cells were then incubated with: (1) FITC-labeled anti-CD45 (Abcam, Cat #27287); (2) mouse monoclonal to CD10 (Abcam, Cat #34175) followed by FITC-labeled goat anti-mouse Ab (Abcam, Cat #6785); and (3) mouse monoclonal to CD13 (Abcam, Cat #7417) followed by FITC-labeled goat anti-mouse Ab (Abcam, Cat #6785). Propidium iodide (PI) was included in each sample to monitor viability as only live cells were gated for further analysis. Using this procedure, it was confirmed that testing for a marker profile comprising CD10, CD13, and CD45 using flow cytometry is successful to identify hUTC and PBMC.

In one embodiment, the unique marker profile may be provided as part of a kit containing the materials for testing for the unique marker profile.

The step of identifying the unique marker profile may also include the step of verifying its correctness and possible validation of the unique marker profile in compliance with relevant regulations.

B. Obtaining a Patient Sample

The step of obtaining a patient sample includes the step of taking a blood sample from the patient. As mentioned above, in one embodiment, the patient may be a human, non-human primate, mouse, rat, hamster, guinea pig, dog, or pig. The blood sample may be further purified or concentrated to isolate the cells. For example, in one embodiment, the plasma may be removed from the blood. The plasma may be removed using standard techniques in the art including centrifugation.

The patient sample (e.g. fraction) used for further analysis comprises the allogeneic therapeutic cells of interest and the peripheral blood mononuclear cells from the patient. In one embodiment, the patient sample comprises a human umbilical cord tissue-derived/peripheral blood mononuclear cell fraction.

In one embodiment, the step of obtaining a patient sample further includes isolating the human umbilical cord tissue-derived/peripheral blood mononuclear cell fraction from the blood sample. This embodiment may further include the step of removing plasma.

In an alternate embodiment, the step of obtaining a patient sample includes use of Ficoll extraction.

C. Analysis of the Patient Sample

Generally, the step of analysis comprises taking the patient blood sample and testing it for the presence of the distinguishing unique marker profile for allogeneic therapeutic cells (e.g. hUTC). The step of analysis may also include determining the presence of PBMC based on a unique marker profile as determined above. For instance, the step of analyzing the patient sample includes use of an assay method to test for one or more markers positive for the allogeneic therapeutic cells and one or more markers positive for peripheral blood mononuclear cells. Thus, the step of analysis includes detecting the presence of cells based on the unique marker profile assayed above. Alternatively, the step of analyzing the patient sample includes use of an assay method to test for one or more unique markers positive for the allogeneic therapeutic cell sufficient to distinguish these cells from the peripheral blood mononuclear cells.

In one embodiment, the step of analysis includes detecting one or more markers positive for peripheral blood mononuclear cells and one or more markers positive for human umbilical cord tissue-derived cells in the patient blood sample. In another embodiment, the step of analysis includes detecting one or more unique markets positive for hUTC sufficient to distinguish these cells from PBMC in the patient blood sample. The patient blood sample may be a human umbilical cord tissue-derived/peripheral blood mononuclear cell fraction.

The step of analysis may be carried out using a variety of standard laboratory techniques. In one embodiment, the step of analyzing may utilize flow cytometry, ELISA, immunohistochemistry, nucleic acid detection, PCR, or combinations thereof.

Multiple technologies including protein-based technologies such as ELISA and immune-histochemistry or nucleic acid based technologies such as in situ hybridization may be used to detect the presence of hUTC in blood. Alternatively, PCR technology may be used to facilitate the relative quantification of hUTC in a blood sample.

In one preferred embodiment of the invention, the methods of the invention are used to distinguish human hUTC from human PBMC. In one embodiment, the unique marker profile comprises one or more of CD10, CD13, NRP1, CD45, LAMP1, DKK3, NRP1, or LAMB1 and the step of analyzing may utilize flow cytometry, ELISA, immunohistochemistry, nucleic acid detection, PCR, or combinations thereof. In another embodiment, step of analysis includes flow cytometry to test for CD10 and/or CD13 as a positive marker for human umbilical cord tissue-derived cells and CD45 as a positive marker for human peripheral blood mononuclear cells. In another embodiment, the methods of the invention are used to distinguish hUTC from human PBMC based on the presence of one or more unique positive markers (such as e.g. CD10, CD13, NRP1, LAMP1, DKK3, NRP1, or LAMB1) sufficient to distinguish these cells from the PBMC.

D. Optional Enrichment Steps

The methods of the invention may further include one or more enrichment steps. The term "enrichment" as used herein refers to the process of substantially increasing the ratio of target bioentities (e.g., allogeneic therapeutic cells (such as e.g. hUTC)) to non-target materials (e.g. PBMC) in the processed analytical sample compared to the ratio in the original biological sample.

In particular, if more sensitivity is required for detection of the allogeneic therapeutic cells (e.g. hUTC), an enrichment step may be necessary prior to analyzing the patient sample. For example, an enrichment step may be necessary where there are so few allogeneic therapeutic cells (e.g. hUTC) present relative to the number of blood cells or that the amount of allogeneic therapeutic cells falls below the limits of detection of the laboratory technique. Using enrichment, the methods of the invention can identify and quantify allogeneic therapeutic cells, even if present in very low concentration in the patient's blood and provide a mechanism to facilitate quantification of cells present in any given sample.

A variety of standard techniques may be used for the one or more enrichment steps. These techniques include, but are not limited to, the use of selective medium for enrichment and depletion of specific cell types, selective adhesions method, physical and biological methods of cell separation, density gradient electrophoresis, centrifugation and the like. Exemplary enrichment techniques are immunoaffinity column, immunoaffinity beads, centrifugation through a sucrose or Ficoll gradient.

Thus, depending on the number of hUTC/ml of blood and the number of hUTC/million PBMC, it may be necessary to isolate or enrich the hUTC fraction prior to analysis. Anti-CD45 antibody, conjugated to magnetic beads may be used for this purpose (see discussion below).

Cell Separation with Magnetic Beads

The enrichment step may include cell separation with magnetic particles/beads. Magnetic particles are well known in the art, as is their use in immune and other bio-specific affinity reactions. Generally, any material that facilitates magnetic or gravitational separation may be employed for this purpose. Exemplary enrichment procedures using magnetic beads are described in U.S. Pat. No. 7,863,012 and U.S. Published Application No. 2011/0147180, which are incorporated by reference.

Magnetic particles can be classified based on size: large (1.5 to about 50 microns); small (about 0.7-1.5 microns); or colloidal (<200 nm), which are also referred to as nanoparticles. The third, which are also known as ferrofluids or ferrofluid-like materials and have many of the properties of classical ferrofluids, are sometimes referred to herein as colloidal, superparamagnetic particles.

Small magnetic particles of the type described above are quite useful in analyses involving bio-specific affinity reactions, as they are conveniently coated with biofunctional polymers (e.g., proteins), provide very high surface areas, and give reasonable reaction kinetics. Magnetic particles ranging from about 0.7-1.5 microns have been described in the patent literature, including, by way of example, U.S. Pat. Nos. 3,970,518; 4,018,886; 4,230,685; 4,267,234; 4,452,773; 4,554,088; and 4,659,678. Certain of these particles are disclosed to be useful solid supports for immunological reagents.

The efficiency with which magnetic separations can be done and the recovery and purity of magnetically labeled cells will depend on many factors. These include: number of cells being separated, receptor or epitope density of such cells, magnetic load per cell, non-specific binding (NSB) of the magnetic material, carry-over of entrapped non-target cells, technique employed, nature of the vessel, nature of the vessel surface, viscosity of the medium, and magnetic separation device employed. If the level of non-specific binding of a system is substantially constant, as is usually the case, then as the target population decreases so will the purity.

As an example, a system with 0.8% NSB that recovers 80% of a population, which is at 0.25% in the original mixture, will have a purity of 25%. Whereas, if the initial population was at 0.01% (one target cell in $10^6$ bystander cells), and the NSB were 0.001%, then the purity would be 8%. Hence, a high the purity of the target material in the specimen mixture results in a more specific and effective collection of the target material. Extremely low non-specific binding is required or advantageous to facilitate detection and analysis of rare cells, such as epithelial derived tumor cells present in the circulation.

The smaller the population of a targeted cell (such as e.g. hUTC), the more difficult it will be to magnetically label and to recover. Furthermore, labeling and recovery will markedly depend on the nature of magnetic particle employed. For example, when cells are incubated with large magnetic particles, such as Dynal® magnetic beads (Invitrogen), cells are labeled through collisions created by mixing of the system, as the beads are too large to diffuse effectively. Thus, if a cell were present in a population at a frequency of 1 cell per ml of blood or even less, then the probability of labeling target cells will be related to the number of magnetic particles added to the system and the length of time of mixing. Since mixing of cells with such particles for substantial periods would be deleterious, it becomes necessary to increase particle concentration as much as possible. There is, however, a limit to the quantity of magnetic particle that can be added, as one can substitute a rare cell mixed in with other blood cells for a rare cell mixed in with large quantities of magnetic particles upon separation. The latter condition does not markedly improve the ability to enumerate the cells of interest or to examine them.

In one embodiment, the magnetic particles for use in carrying out the enrichment step behave as colloids. Such particles are characterized by their sub-micron particle size, which is generally less than about 200 nm (0.20 microns), and their stability to gravitational separation from solution for extended periods. In addition to the many other advantages, this size range makes them essentially invisible to analytical techniques commonly applied to cell analysis. Particles within the range of about 90-150 nm and having between about 70-90% magnetic mass are contemplated for use in the present invention. Suitable magnetic particles are composed of a crystalline core of superparamagnetic material surrounded by molecules, which are bonded, e.g., physically absorbed, or covalently attached to the magnetic core and which confer stabilizing colloidal properties. The coating material should preferably be applied in an amount effective to prevent non-specific interactions between biological macromolecules found in the sample and the magnetic cores. Such biological macromolecules may include carbohydrates such as sialic acid residues on the surface of non-target cells, lectins, glycoproteins, and other membrane components. In addition, the material should contain as much magnetic mass per nanoparticle as possible. The size of the magnetic crystals comprising the core is sufficiently small that they do not contain a complete magnetic domain. The size of the nanoparticles is sufficiently small such that their Brownian energy exceeds their magnetic moment. Consequently, North Pole, South Pole alignment and subsequent mutual attraction/repulsion of these colloidal magnetic particles does not appear to occur even in moderately strong magnetic fields, contributing to their solution stability. Finally, the magnetic particles should be separable in high magnetic gradient external field separators. That characteristic facilitates sample handling and provides economic advantages over the more complicated internal gradient columns loaded with ferromagnetic beads or steel wool. Magnetic particles having the above-described properties can be prepared by modification of base materials described in U.S. Pat. Nos. 4,795,698; 5,597,531, and 5,698,271, each incorporated by reference herein.

Since small nanoparticles (30-70 nm) will diffuse more readily, they will preferentially label cells compared with their larger counterparts. When very high gradients are used, such as in internal gradient columns, the performance of these materials, regardless of size, makes little difference. On the other hand, when using external gradients, or gradients of lesser magnitude than can be generated on micro bead or steel wool columns, the occupancy of small nanoparticles on cells has a significant effect. This was conclusively shown to be the case by fractionating DC nanoparticles and studying the effects on recovery. Based on these studies and other optimization experiments, means for fractionating nanoparticles magnetically or on columns was established where base coated magnetic particles could be prepared that were devoid of excessively small or large nanoparticles. For example, base coated particles of mean diameter 100 nm can be produced which contain at best trace amounts of material smaller than 80 nm or over 130 nm. Similarly, material of about 120 nm can be made with no appreciable material smaller than 90-95 nm and over 160 nm. Such materials performed optimally with regard to recovery and could be made sub-optimal by the inclusion of 60-70 nm nanoparticles. One preferred particle size range for use in practicing this invention is 90-150 nm for base coated magnetic particles, e.g., BSA-coated magnetite.

Based on the foregoing, high gradient magnetic separation with an external field device employing highly magnetic, low non-specific binding, colloidal magnetic particles is the method of choice for separating a cell subset of interest from a mixed population of eukaryotic cells (such as e.g. allogeneic therapeutic cells (e.g. hUTC) in peripheral blood mononuclear cells), particularly if the subset of interest comprises but a small fraction of the entire population. Such materials, because of their diffusive properties, readily find and magnetically label rare events, such as tumor cells in blood. In one embodiment, for magnetic separations for allogeneic therapeutic (e.g. hUTC) cell analysis to be successful, the magnetic particles must be specific for epitopes that are not present on the allogeneic therapeutic cells (e.g. hUTC).

An enrichment step by use of magnetic beads includes using magnetic nanoparticles (such as those described above) which are labeled with a monoclonal antibody. These monoclonal antibodies may be antibodies identifying peripheral blood mononuclear cells but not allogeneic therapeutic cells. The monoclonal antibody attached to the nanoparticles bind to the peripheral blood mononuclear cells which may then be separated using magnetic means. Typically, such separation is achieved via the use of a high magnetic gradient external field separators. An exemplary suitable technique to separate by magnetic means is described in U.S. Pat. No. 6,365,362, the disclosure which is incorporated herein. In one embodiment, an Anti-CD45 antibody conjugated to a magnetic particle is used. Alternatively, the enrichment step includes use of Anti-CD4 and anti-CD8 antibodies, to remove T-cells.

In another embodiment, the enrichment step includes monoclonal antibodies identifying the allogeneic therapeutic cells. In a further embodiment, the allogeneic therapeutic cells are hUTC and the antibodies include one or more of anti-CD10 or anti-CD13 antibodies.

In one embodiment, the methods of the invention include use of a Cell Search System (Veridex, LLC (Raritan, N.J.)), which has been optimized for the detection of hUTC and PBMC.

As the approximate amount of allogeneic therapeutic cells (such as e.g. hUTC) in a patient sample may be unknown, the methods of the invention may also include the step of preserving a sufficient patient sample to run an additional analysis. This may be particularly useful where initial analysis might not be able to detect the allogeneic therapeutic cells (such as e.g. hUTC) due to allogeneic therapeutic cells being present in an amount below the detection limit of the assay technique used. Thus, in one embodiment, the method further includes an additional analysis of a patient sample if no allogeneic therapeutic cells are initially detected (such as e.g. hUTC). This additional analysis also includes one or more enrichment steps such as those discussed above.

E. Determining Presence of Allogeneic Therapeutic Cells and Peripheral Blood Mononuclear Cells in the Patient's Blood Sample The methods of the invention further comprise determining the presence of allogeneic therapeutic cells in a sample of peripheral blood mononuclear cells. The step of determining the presence of said cells includes comparing the results of the analysis of the sample to the unique marker, which was assayed for above, wherein the presence of unique markers for allogeneic therapeutic cells indicates the presence of the allogeneic therapeutic cells in the sample. The step of determining may also include comparing the result to a unique marker for the PBMC as identified above. Thus, the determination step includes comparing the results for the one or more markers positive for the allogeneic therapeutic cell (e.g. hUTC) and the one or more markers negative for PBMC to the marker profile above.

In another embodiment, the method of the invention comprises determining the presence of human umbilical cord tissue-derived in a sample of peripheral blood mononuclear cells (such as e.g. human or rodent). The determination step includes comparing the results of the analysis of the sample to the unique marker, which was assayed for above, wherein the presence of unique markers for the allogeneic therapeutic cells indicates the presence of the hUTC cells in the sample. The determination step may also include comparing the result to a unique marker for the PBMC as identified above. The determination step may include one or more markers positive for the hUTC and one or more markers positive for PBMC as discussed above.

The determination step also includes distinguishing between the human peripheral blood mononuclear cells and human umbilical cord tissue-derived cells based on the detection of one or more markers positive for human peripheral blood mononuclear cells and one or more markers positive for human umbilical cord tissue-derived cells. The determination step may also include differentiating between human umbilical cord tissue-derived cells administered to the patient and human peripheral blood mononuclear cells from the patient.

The step of determining the presence of the cells may also include quantifying the cells. In one embodiment, the determination step for the presence of hUTC includes quantifying the number of hUTC in the sample.

The step of determining the presence may further include selecting one or more human umbilical cord tissue-derived cells based on the presence of the unique marker profile (such as e.g. one or more markers positive for hUTC).

The determination step may also include detecting the presence of the human peripheral blood mononuclear cells and human umbilical cord tissue-derived cells based on the detection of CD45 as a marker positive for human peripheral blood mononuclear cells and CD10 or CD13 as a marker positive for human umbilical cord tissue-derived cells.

In alternate embodiments, the methods described herein may be suitable to distinguish allogeneic therapeutic cells from rat PBMC, which may be particularly useful for monitoring in rat disease models.

In one embodiment, the present invention describes a method for the identification of hUTC in blood. The method involves the following steps: (a) providing a blood sample from a patient that has been treated with human umbilical cord tissue-derived cells; (b) analyzing the sample using an assay method to detect one or more markers positive for human peripheral blood mononuclear cells and one or more markers positive for human umbilical cord tissue-derived cells; and (c) distinguishing between the human peripheral blood mononuclear cells and one or more markers positive for human umbilical cord tissue-derived cells. A further step of quantifying the amount of hUTC may also be employed. In one embodiment, one or more of the markers shown in Example 3 are used.

In another embodiment, the methods of the invention are suitable for identifying about 1,700 or more hUTC/ml in the presence of 1 million human PBMC using flow cytometry without relying on an enrichment step.

III. Kits and Systems for Testing for Allogeneic Therapeutic Cells in a Blood Sample Another embodiment of the invention is a kit for testing for the presence of allogeneic therapeutic cells such as hUTC in a blood sample using the methods of the invention.

The kits may comprise the distinguishing unique marker profile and suitable components for identifying the distinguishing unique marker profile according to one or more analytical procedures. For example, a kit suitable for distinguishing a unique marker profile by using RT-PCR would include PCR primers suitable for amplifying the unique marker profile genes. Similarly, a kit suitable for distinguishing a unique marker profile by an antibody-linked assay would include the antibodies that bind to the markers.

In one embodiment, the kit is designed to detect hUTC in a population of PBMC. In another embodiment, the kit comprises the unique marker profile CD10, CD13 and CD45 and other suitable components for identifying CD10, CD13 and CD45 using one or more of flow cytometry, ELISA, immunohistochemistry, nucleic acid detection, PCR or combinations thereof.

Yet another embodiment is a system for detecting allogeneic therapeutic cells (such as e.g. hUTC) in a population of PBMC. The system includes materials necessary for carrying out the methods of the invention.

IV. Human Umbilical Cord Tissue-Derived Cells

While it is contemplated that the methods of the invention may be used to distinguish therapeutic (e.g. progenitor/stem cells) from host cells, in a preferred embodiment, the cells may be human umbilical cord tissue-derived-cells ("hUTC" or "UTC"). Useful human umbilical cord tissue-derived cells are isolated from human umbilical cord tissue substantially free of blood, are capable of self-renewal and expansion in culture, and have the potential to differentiate. The UTC and UTC populations suitable for identification by the methods of the invention are described in detail in detailed herein below as well as U.S. Pat. Nos. 7,510,873; 7,524,489; and U.S. Pub. App. No. 2005/005863.

A. Isolation and Growth of Umbilical Cord Tissue-Derived Cells

According to the methods described herein, a mammalian umbilical cord is recovered upon or shortly after termination of either a full-term or a pre-term pregnancy, e.g., after expulsion of after birth. The postpartum tissue may be transported from the birth site to a laboratory in a sterile container such as a flask, beaker, culture dish, or bag. The container may have a solution or medium, including but not limited to a salt solution, such as Dulbecco's Modified Eagle's Medium (DMEM) (also known as Dulbecco's Minimal Essential Medium) or phosphate buffered saline (PBS), or any solution used for transportation of organs used for transplantation, such as University of Wisconsin solution or perfluorochemical solution. One or more antibiotic and/or antimycotic agents, such as but not limited to penicillin, streptomycin, amphotericin B, gentamicin, and nystatin, may be added to the medium or buffer. The postpartum tissue may be rinsed with an anticoagulant solution such as heparin-containing solution. It is preferable to keep the tissue at about 4-10° C. prior to extraction of UTC. It is even more preferable that the tissue not be frozen prior to extraction of UTC.

Isolation of UTC preferably occurs in an aseptic environment. The umbilical cord may be separated from the placenta by means known in the art. Blood and debris are preferably removed from the postpartum tissue prior to isolation of UTC. For example, the postpartum tissue may be washed with buffer solution, including but not limited to phosphate buffered saline. The wash buffer also may comprise one or more antimycotic and/or antibiotic agents, including but not limited to penicillin, streptomycin, amphotericin B, gentamicin, and nystatin.

Postpartum tissue comprising an umbilical cord or a fragment or section thereof is disaggregated by mechanical force (mincing or shear forces). In a presently preferred embodiment, the isolation procedure also utilizes an enzymatic digestion process. Many enzymes are known in the art to be useful for the isolation of individual cells from complex tissue matrices to facilitate growth in culture. Digestion enzymes range from weakly digestive (e.g. deoxyribonucleases and the neutral protease, dispase) to strongly digestive (e.g. papain and trypsin), and are available commercially. A non-exhaustive list of enzymes compatible herewith includes mucolytic enzyme activities, metalloproteases, neutral proteases, serine proteases (such as trypsin, chymotrypsin, or elastase), and deoxyribonucleases. Presently preferred are enzyme activities selected from metalloproteases, neutral proteases and mucolytic activities. For example, collagenases are known to be useful for isolating various cells from tissues. Deoxyribonucleases can digest single-stranded DNA and can minimize cell clumping during isolation. Preferred methods involve enzymatic treatment with e.g. collagenase and dispase, or collagenase, dispase, and hyaluronidase. In certain embodiments, a mixture of collagenase and the neutral protease dispase are used in the dissociating step. More specific embodiments employ digestion in the presence of at least one collagenase from *Clostridium histolyticum*, and either of the protease activities, dispase, and thermolysin. Still other embodiments employ digestion with both collagenase and dispase enzyme activities. Also utilized are methods that include digestion with a hyaluronidase activity in addition to collagenase and dispase activities. The skilled artisan will appreciate that many such enzyme treatments are known in the art for isolating cells from various tissue sources. For example, the enzyme blends for tissue disassociation sold under the trade name LIBERASE (Roche, Indianapolis, Ind.) are suitable for use in the instant methods. Other sources of enzymes are known, and the skilled artisan may also obtain such enzymes directly from their natural sources. The skilled artisan is also well-equipped to assess new or additional enzymes or enzyme combinations for their utility in isolating the cells of the invention. Preferred enzyme treatments are 0.5, 1, 1.5, or 2 hours long or longer. In other preferred embodiments, the tissue is incubated at 37° C. during the enzyme treatment of the dissociation step.

In some embodiments of the invention, postpartum tissue is separated into sections comprising various aspects of the tissue, such as neonatal, neonatal/maternal, and maternal aspects of the placenta, for instance. The separated sections then are dissociated by mechanical and/or enzymatic dissociation according to the methods described herein. Cells of neonatal or maternal lineage may be identified by any means known in the art, e.g. by karyotype analysis or in situ hybridization for a Y chromosome.

Isolated cells or umbilical cord tissue from which a UTC is derived may be used to initiate, or seed, cell cultures. Isolated cells are transferred to sterile tissue culture vessels either uncoated or coated with extracellular matrix or ligands such as laminin, collagen (native, denatured or cross-linked), gelatin, fibronectin, and other extracellular matrix proteins. In addition to the culture media disclosed herein, a UTC may be cultured in any culture medium capable of sustaining growth of the cell such as, but not limited to, DMEM (high or low glucose), advanced DMEM, DMEM/MCDB 201, Eagle's basal medium, Ham's F10 medium (F10), Ham's F-12 medium (F12), Iscove's modified Dulbecco's medium, Mesenchymal Stem Cell Growth Medium (MSCGM), DMEM/F12, RPMI 1640, and serum/media free medium sold under the trade name CELL-GRO-FREE (Mediatch, Inc., Herndon, Va.). The culture medium may be supplemented with one or more components including, e.g., fetal bovine serum (FBS), preferably about 2-15% (v/v); equine serum (ES); human serum (HS); beta-mercaptoethanol (BME or 2-ME), preferably about 0.001% (v/v); one or more growth factors, e.g., platelet-derived growth factor (PDGF), epidermal growth factor (EGF), fibroblast growth factor (FGF), vascular endothelial growth factor (VEGF), insulin-like growth factor-1 (IGF-1), leukocyte inhibitory factor (LIF) and erythropoietin (EPO); amino acids, including L-valine; and one or more antibiotic and/or antimycotic agents to control microbial contamination, such as penicillin G, streptomycin sulfate, amphotericin B, gentamicin, and nystatin, either alone or in combination. The culture medium may comprise Growth Medium as defined in the Examples below.

The cells are seeded in culture vessels at a density to allow cell growth. In a preferred embodiment, the cells are cultured at about 0 to about 5% by volume $CO_2$ in air. In some preferred embodiments, the cells are cultured at about 2 to about 25% $O_2$ in air, preferably about 5 to about 20% $O_2$ in air. The cells preferably are cultured at a temperature of about 25 to about 40° C. and more preferably are cultured at 37° C. The cells are preferably cultured in an incubator. The medium in the culture vessel can be static or agitated, e.g., using a bioreactor. The UTC is preferably grown under low oxidative stress (e.g., with addition of glutathione, Vitamin C, Catalase, Vitamin E, N-Acetylcysteine). "Low oxidative stress" refers to conditions of no or minimal free radical damage to the cultured cells.

Methods for the selection of the most appropriate culture medium, medium preparation, and cell culture techniques are well known in the art and are described in a variety of sources, including Doyle et al., (eds.), 1995, Cell & Tissue Culture: Laboratory Procedures, John Wiley & Sons, Chichester; and Ho and Wang (eds.), 1991, Animal Cell Bioreactors, Butterworth-Heinemann, Boston, which are incorporated herein by reference.

After culturing the isolated cells or tissue fragments for a sufficient period, a UTC will have grown out, either because of migration from the postpartum tissue or cell division, or both. In some embodiments of the invention, the UTC is passaged, or removed to a separate culture vessel containing fresh medium of the same or a different type as that used initially, where the population of cells can be mitotically expanded. The cells of the invention may be used at any point between passage 0 and senescence. The cells preferably are passaged between about 3 and about 25 times, more preferably are passaged about 4 to about 12 times, and preferably are passaged 10 or 11 times. Cloning and/or subcloning may be performed to confirm that a clonal population of cells has been isolated.

In certain embodiments, the different cell types present in postpartum tissue are fractionated into subpopulations from which the UTC can be isolated. Fractionation or selection may be accomplished using standard techniques for cell separation including, but not limited to, enzymatic treatment to dissociate postpartum tissue into its component cells, followed by cloning and selection of specific cell types, including but not limited to selection based on morphological and/or biochemical markers; selective growth of desired cells (positive selection), selective destruction of unwanted cells (negative selection); separation based upon differential cell agglutinability in the mixed population such as, e.g., with soybean agglutinin; freeze-thaw procedures; differential adherence properties of the cells in the mixed population; filtration; conventional and zonal centrifugation; centrifugal elutriation (counter-streaming centrifugation); unit gravity separation; countercurrent distribution; electrophoresis; and fluorescence activated cell sorting (FACS). For a review of clonal selection and cell separation techniques, see Freshney, 1994, Culture of Animal Cells: A Manual of Basic Techniques, 3rd Ed., Wiley-Liss, Inc., New York, which is incorporated herein by reference.

The culture medium is changed as necessary, e.g., by carefully aspirating the medium from the dish, e.g., with a pipette, and replenishing with fresh medium. Incubation is continued until a sufficient number or density of cells accumulates in the dish. The original explanted tissue sections may be removed and the remaining cells trypsinized using standard techniques or using a cell scraper. After trypsinization, the cells are collected, removed to fresh medium, and incubated as above. In some embodiments, the medium is changed at least once at approximately 24 hours post-trypsinization to remove any floating cells. The cells remaining in culture are considered to be UTC.

The UTC may be cryopreserved. Accordingly, UTC for autologous transfer (for either the mother or child) may be derived from appropriate postpartum tissues following the birth of a child, then cryopreserved so as to be available in the event they are later needed for transplantation.

B. Characteristics of Umbilical Cord Tissue-Derived Cells

While hUTC may be distinguished from PBMC based on the presence of e.g. CD45, CD13, and CD10 and other markers discussed above and in the examples below, hUTC possess a variety of other unique characteristics.

The UTC may be characterized, e.g., by growth characteristics (e.g., population doubling capability, doubling time, passages to senescence), karyotype analysis (e.g., normal karyotype; maternal or neonatal lineage), flow cytometry (e.g., FACS analysis), immunohistochemistry and/or immunocytochemistry (e.g., for detection of epitopes), gene expression profiling (e.g., gene chip arrays); polymerase chain reaction (e.g., reverse transcriptase PCR, real time PCR, and conventional PCR)), protein arrays, protein secretion (e.g., by plasma clotting assay or analysis of PDC-conditioned medium, e.g., by Enzyme Linked ImmunoSorbent Assay (ELISA)), mixed lymphocyte reaction (e.g., as measure of stimulation of PBMCs), and/or other methods known in the art.

Examples of suitable UTC derived from umbilicus tissue were deposited with the American Type Culture Collection (10801 University Boulevard, Manassas, Va. 20110) on Jun. 10, 2004, and assigned ATCC Accession Numbers as follows: (1) strain designation UMB 022803 (P7) was assigned Accession No. PTA-6067; and (2) strain designation UMB 022803 (P17) was assigned Accession No. PTA-6068.

In various embodiments, the UTC possesses one or more of the following growth features: (1) they require L-valine for growth in culture; (2) they are capable of growth in atmospheres containing oxygen from about 5% to at least about 20%; (3) they have the potential for at least about 40 doublings in culture before reaching senescence; and (4) they attach and expand on a coated or uncoated tissue culture vessel, wherein the coated tissue culture vessel comprises a coating of gelatin, laminin, collagen, polyornithine, vitronectin or fibronectin.

In certain embodiments, the UTC possesses a normal karyotype, which is maintained as the cells are passaged. Methods for karyotyping are available and known to those of skill in the art.

In other embodiments, the UTC may be characterized by production of certain proteins, including: (1) production of at least one of tissue factor, vimentin, and alpha-smooth muscle actin; and (2) production of at least one of CD10, CD13, CD44, CD73, CD90, PDGFr-alpha, PD-L2 and HLA-A,B,C cell surface markers, as detected by flow cytometry. In other embodiments, the UTC may be characterized by lack of production of at least one of CD31, CD34, CD45, CD80, CD86, CD117, CD141, CD178, B7-H2, HLA-G, and HLA-DR, DP, DQ cell surface markers, as detected by flow cytometry. Particularly preferred are cells that produce at least two of tissue factor, vimentin, and alpha-smooth muscle actin. Also preferred are those cells producing all three of the proteins tissue factor, vimentin, and alpha-smooth muscle actin.

In other embodiments, the UTC may be characterized by gene expression, which relative to a human cell that is a fibroblast, a mesenchymal stem cell, or an iliac crest bone marrow cell, is increased for a gene encoding at least one of: interleukin 8; reticulon 1; chemokine (C-X-C motif) ligand 1 (melonoma growth stimulating activity, alpha); chemokine (C-X-C motif) ligand 6 (granulocyte chemotactic protein 2); chemokine (C-X-C motif) ligand 3; and tumor necrosis factor, alpha-induced protein 3.

In yet other embodiments, the UTC may be characterized by gene expression, which relative to a human cell that is a fibroblast, a mesenchymal stem cell, or an iliac crest bone marrow cell, is reduced for a gene encoding at least one of: short stature homeobox 2; heat shock 27 kDa protein 2; chemokine (C-X-C motif) ligand 12 (stromal cell-derived factor 1); elastin (supravalvular aortic stenosis, Williams-Beuren syndrome); *Homo sapiens* mRNA; cDNA DKFZp586M2022 (from clone DKFZp586M2022); mesenchyme homeo box 2 (growth arrest-specific homeo box); sine oculis homeobox homolog 1 (*Drosophila*); crystallin, alpha B; disheveled associated activator of morphogenesis 2; DKFZP586B2420 protein; similar to neuralin 1; tetranectin (plasminogen binding protein); src homology three (SH3) and cysteine rich domain; cholesterol 25-hydroxylase; runt-related transcription factor 3; interleukin 11 receptor, alpha; procollagen C-endopeptidase enhancer; frizzled homolog 7 (*Drosophila*); hypothetical gene BC008967; collagen, type VIII, alpha 1; tenascin C (hexabrachion); iroquois homeobox protein 5; hephaestin; integrin, beta 8; synaptic vesicle glycoprotein 2; neuroblastoma, suppression of tumorigenicity 1; insulin-like growth factor binding protein 2, 36 kDa; *Homo sapiens* cDNA FLJ12280 fis, clone MAMMA1001744; cytokine receptor-like factor 1; potassium intermediate/small conductance calcium-activated channel, subfamily N, member 4; integrin, beta 7; transcriptional co-activator with PDZ-binding motif (TAZ); sine oculis homeobox homolog 2 (*Drosophila*); KIAA1034 protein; vesicle-associated membrane protein 5 (myobrevin); EGF-containing fibulin-like extracellular matrix protein 1; early growth response 3; distal-less homeo box 5; hypothetical protein FLJ20373; aldo-keto reductase family 1, member C3 (3-alpha hydroxysteroid dehydrogenase, type II); biglycan; transcriptional co-activator with PDZ-binding motif (TAZ); fibronectin 1; proenkephalin; integrin, beta-like 1 (with EGF-like repeat domains); *Homo sapiens* mRNA full length insert cDNA clone EUROIMAGE 1968422; EphA3; KIAA0367 protein; natriuretic peptide receptor C/guanylate cyclase C (atrionatriuretic peptide receptor C); hypothetical protein FLJ14054; *Homo sapiens* mRNA; cDNA DKFZp564B222 (from clone DKFZp564B222); BCL2/adenovirus E1B 19 kDa interacting protein 3-like; AE binding protein 1; and cytochrome c oxidase subunit VIIa polypeptide 1 (muscle).

In other embodiments, the UTC may be characterized when cultured by secretion of at least one of MCP-1, IL-6, IL-8, GCP-2, HGF, KGF, FGF, HB-EGF, BDNF, TPO, MIP1b, 1309, MDC RANTES, and TIMP1. In addition, the UTC may be characterized when cultured by lack of secretion of at least one of TGF-beta2, ANG2, PDGFbb, MIP1A, and VEGF.

In some embodiments, the UTC are derived from umbilical cord tissue substantially free of blood, are capable of self-renewal and expansion in culture, require L-valine for growth, can grow in at least about 5% oxygen, and comprise at least one of the following characteristics: potential for at least about 40 doublings in culture; attachment and expansion on a coated or uncoated tissue culture vessel that comprises a coating of gelatin, laminin, collagen, polyornithine, vitronectin, or fibronectin; production of vimentin and alpha-smooth muscle actin; production of CD10, CD13, CD44, CD73, and CD90; and, expression of a gene, which relative to a human cell that is a fibroblast, a mesenchymal stem cell, or an iliac crest bone marrow cell, is increased for a gene encoding interleukin 8 and reticulon 1. In some embodiments, such UTC does not produce CD45 and CD117.

In preferred embodiments, the cell comprises two or more of the above-listed growth, protein/surface marker production, gene expression, or substance-secretion characteristics. More preferred is a cell comprising three, four, five, or more of the characteristics. Still more preferred is a UTC comprising six, seven, eight, or more of the characteristics. More preferred is a cell comprising all of above characteristics.

Among cells that are presently preferred for use with the invention in several of its aspects are postpartum cells having the characteristics described above and more particularly those wherein the cells have normal karyotypes and maintain normal karyotypes with passaging, and further wherein the cells express each of the markers CD10, CD13, CD44, CD73, CD90, PDGFr-alpha, and HLA-A, B,C, wherein the cells produce the immunologically-detectable proteins which correspond to the listed markers. Still more preferred are those cells which in addition to the foregoing do not produce proteins corresponding to any of the markers CD31, CD34, CD45, CD117, CD141, or HLA-DR,DP,DQ, as detected by flow cytometry.

In an embodiment, the UTC are isolated from human umbilical cord tissue substantially free of blood, are capable of self-renewal and expansion in culture, have the potential to differentiate, lack the production of CD117 or CD45, express CD10 and CD13, and do not express hTERT or telomerase. These UTC optionally express oxidized low density lipoprotein receptor 1, reticulon, chemokine receptor ligand 3, and/or granulocyte chemotactic protein; and/or do not express CD31 or CD34; and/or express, relative to a human fibroblast, mesenchymal stem cell, or iliac crest bone marrow cell, increased levels of interleukin 8 or reticulon 1; and/or express CD44, CD73, and CD90.

In another embodiment, the UTC are isolated from human umbilical cord tissue substantially free of blood, are capable of self-renewal and expansion in culture, have the potential to differentiate, express CD10, CD13, CD90, and HLA-ABC, and do not express CD34, CD45, CD117, and HLA-DR. Optionally, these cells also do not express hTERT or telomerase. In one embodiment, the cells also express CD44, and CD43. In yet another embodiment, the cells also do not express CD31. These UTC optionally: (i) express oxidized low density lipoprotein receptor 1, reticulon, chemokine receptor ligand 3, and/or granulocyte chemotactic protein; and/or (ii) express, relative to a human fibroblast, mesenchymal stem cell, or iliac crest bone marrow cell, increased levels of interleukin 8 or reticulon 1.

In an alternate embodiment, the UTC are isolated from human umbilical cord tissue substantially free of blood, are capable of self-renewal and expansion in culture, have the potential to differentiate, and have the following characteristics: (1) express CD10, CD13, CD44, CD90, and HLA-ABC; (2) do not express CD31, CD34, CD45, HLA-DR and CD117, and (3) do not express hTERT or telomerase. In another embodiment, the UTC are isolated from human umbilical cord tissue substantially free of blood, are capable of self-renewal and expansion in culture, have the potential to differentiate, and have the following characteristics: (1) express CD10, CD13, CD44, CD90, and HLA-ABC; (2) do not express CD31, CD34, CD45, HLA-DR and CD117; (3) do not express hTERT or telomerase; (4) express oxidized low density lipoprotein receptor 1, reticulon, chemokine receptor ligand 3, and/or granulocyte chemotactic protein; and (5) express, relative to a human fibroblast, mesenchymal stem cell, or iliac crest bone marrow cell, increased levels of interleukin 8 or reticulon 1.

In one embodiment, the hUTC are provided as a population of cells, which may be homogenous. In some embodiments, the cell population may be heterogeneous. A heterogeneous cell population of the invention may comprise at least about 5%, 10%, 20%, 30%, 40%, 50%, 60%, 70%, 80%, 90%, or 95% UTC of the invention. The heterogeneous cell populations of the invention may further comprise stem cells or other progenitor cells, such as myoblasts or other muscle progenitor cells, hemangioblasts, or blood vessel precursor cells; or it may further comprise fully differentiated skeletal muscle cells, smooth muscle cells, pericytes, or blood vessel endothelial cells. In some embodiments, the population is substantially Additionally, as used in the following examples and elsewhere in the specification, the hUTC which may be identified using the screening methods may be isolated and characterized according to the disclosure of U.S. Pat. Nos. 7,510,873; 7,524,489; and U.S. Pub. App. No. 2005/005863, which are incorporated by reference in their entireties as they relate to the description, isolation and characterization of hUTC. Furthermore, enrichment procedures using magnetic beads are described in U.S. Pat. No. 7,863,012 and U.S. Published Application No. 2011/0147180, which are being incorporated in their entireties as they relate to enrichment procedures and magnetic beads.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

EXAMPLES

Example 1

Isolation, Maintenance, and Expansion of hUTC

Human umbilical cord tissue-derived-cells were isolated from four donors and propagated in growth medium supplemented with 15% fetal bovine serum as described above in U.S. Pat. Nos. 7,510,873; 7,524,489; and U.S. Pub. App. No. 2005/005863 and in the Examples below. Early passage cultures were cryopreserved to generate development and working cell banks, termed DCB and WCB, respectively. Live cultures of hUTC were maintained by using one of the following two methods: 1) as adherent cultures in tissue culture flasks; and 2) as suspension cultures in spinner flasks and stirred tank bioreactors. Cells were first seeded onto microcarriers for the latter method.

Three sets of samples were subjected to microarray analysis as follows: (1) Study 1 (Donor microarray study); (2) Study 2 (Temperature excursion study); and (3) Study 3 (Biomarker study).

Study 1 (Donor Microarray Study)

In this set of samples, cells were cultured in spinner flasks, starting from an early passage cell line population doubling PDL 5 and ending with PDL44. A typical culture was initiated by seeding fresh growth medium with an inoculum of about $5 \times 10^5$ cells/ml and left undisturbed for 4 days, at which time a peak viable cell density (VCD of about $3\text{-}4 \times 10^6$ cells/ml) was achieved. Aliquots of cultures were harvested periodically, for a total of thirty-two (32) samples. Table 1-1 below lists the samples in the study.

TABLE 1-1

List of samples included in Study 1 (Donor microarray study)

| Label | Name | Donor Number |
|---|---|---|
| R52550 | Donor 1; PDL = 11.30 | Umb 041505 |
| R52551 | Donor 1; PDL = 20.26 | Umb 041505 |
| R52552 | Donor 1; PDL = 30.06 | Umb 041505 |
| R52553 | Donor 1; PDL = 33.58 | Umb 041505 |
| R52554 | Donor 1; PDL = 36.78 | Umb 041505 |
| R52555 | Donor 1; PDL = 40.03 | Umb 041505 |
| R52556 | Donor 1; PDL = 43.00 | Umb 041505 |
| R52557 | Donor 1; PDL = 44.98 | Umb 041505 |
| R52559 | Donor 2; PDL = 11.30 | Umb 072304A |
| R52560 | Donor 2; PDL = 20.92 | Umb 072304A |
| R52561 | Donor 2; PDL = 30.29 | Umb 072304A |
| R52562 | Donor 2; PDL = 31.13 | Umb 072304A |
| R52563 | Donor 2; PDL = 32.66 | Umb 072304A |
| R52564 | Donor 2; PDL = 33.01 | Umb 072304A |
| R52565 | Donor 2; PDL = 33.81 | Umb 072304A |
| R52558 | Donor 2; PDL = 5.00 | Umb 072304A |
| R52567 | Donor 3; PDL = 10.79 | Umb 083105 |
| R52568 | Donor 3; PDL = 20.12 | Umb 083105 |
| R52569 | Donor 3; PDL = 30.03 | Umb 083105 |
| R52570 | Donor 3; PDL = 30.45 | Umb 083105 |
| R52571 | Donor 3; PDL = 31.16 | Umb 083105 |
| R52572 | Donor 3; PDL = 31.47 | Umb 083105 |
| R52573 | Donor 3; PDL = 31.69 | Umb 083105 |

Harvesting of cells was conducted at any one of the four days of growth as shown in FIG. 1 (right hand side). From the list of 32 samples, 24 were selected for microarray analysis. FIG. 1 shows the population doubling level (PDL) and the region of the growth curve when a particular sample was harvested.

Study 2 (Temperature Excursion Study)

In this set of samples, cells were held at temperatures ranging from 25° C. to 42° C. for up to 18 hours before harvesting. The samples used in this study are shown in Table 1-2 below.

TABLE 1-2

List of samples included in Study 2 (Temperature excursion study)

| Label | Name | Donor |
|---|---|---|
| R52550 | Donor 1; PDL = 11.30 | Umb 041505 |
| R52551 | Donor 1; PDL = 20.26 | Umb 041505 |
| R52552 | Donor 1; PDL = 30.06 | Umb 041505 |
| R52553 | Donor 1; PDL = 33.58 | Umb 041505 |
| R52554 | Donor 1; PDL = 36.78 | Umb 041505 |
| R52555 | Donor 1; PDL = 40.03 | Umb 041505 |
| R52556 | Donor 1; PDL = 43.00 | Umb 041505 |
| R52557 | Donor 1; PDL = 44.98 | Umb 01505 |
| R52559 | Donor 2; PDL = 11.30 | Umb 072304A |
| R52560 | Donor 2; PDL = 20.92 | Umb 072304A |
| R52561 | Donor 2; PDL = 30.29 | Umb 072304A |
| R52562 | Donor 2; PDL = 31.13 | Umb 072304A |
| R52563 | Donor 2; PDL = 32.66 | Umb 072304A |
| R52564 | Donor 2; PDL = 33.01 | Umb 072304A |
| R52565 | Donor 2; PDL = 33.81 | Umb 072304A |
| R52558 | Donor 2; PDL = 5.00 | Umb 072304A |
| R52567 | Donor 3; PDL = 10.79 | Umb 083105 |
| R52568 | Donor 3; PDL = 20.12 | Umb 083105 |
| R52569 | Donor 3; PDL = 30.03 | Umb 083105 |
| R52570 | Donor 3; PDL = 30.45 | Umb 083105 |
| R52571 | Donor 3; PDL = 31.16 | Umb 083105 |
| R52572 | Donor 3; PDL = 31.47 | Umb 083105 |
| R52573 | Donor 3; PDL = 31.69 | Umb 083105 |
| R52566 | Donor 3; PDL = 5.00 | Umb 0105 |
| R52575 | Donor 4; PDL = 10.71 | Umb 090304A |
| R52576 | Donor 4; PDL = 14.66 | Umb 090304A |
| R52577 | Donor 4; PDL = 19.55 | Umb 090304A |
| R52578 | Donor 4; PDL = 25.06 | Umb 090304A |
| R52579 | Donor 4; PDL = 27.25 | Umb 090304A |
| R52580 | Donor 4; PDL = 23.60 | Umb 090304A |
| R52581 | Donor 4; PDL = 30.15 | Umb 090304A |
| R52574 | Donor 4; PDL = 5.00 | Umb 090304A |

Study 3 (Biomarker Study)

For this study, a set of eight (8) samples were used. The cells were expanded in a stirred tank bioreactor and harvested at PDL30. The samples used in this study are shown in Table 1-3 below.

TABLE 1-3

List of samples included in Study 3 (Biomarker study)

| Exp. ID | Exp. Name |
|---|---|
| E55465 | Donor 1_DCB_Early Passage PDL 12_Set1 |
| E55466 | Donor 1_DCB_Early Passage PDL 12_Set2 |
| E55467 | Donor 1_DCB_Late Passage PDL 40_Set1 |
| E55468 | Donor 1_DCB_Late Passage PDL 40_Set2 |
| E55469 | Donor 1_WCB_Early Passage PDL 16_Set1 |
| E55470 | Donor 1_WCB_Early Passage PDL 16_Set2 |
| E55471 | Donor 1_WCB_Late Passage PDL 36_Set1 |
| E55472 | Donor 1_WCB_Late Passage PDL 36_Set2 |

Data Analysis

An Affymetrix GeneChip® HT HG-U133+ PM array was used for microarray data generation. The data was analyzed in two stages. In the first step, the microarray data generated from the temperature excursion study (Study 2, Table 1-2) to compare the expression profile of hUTC with that of human PBMC. The expression level of various genes in PBMC, was obtained from public sources, including, the National Center for Biotechnology (NCBI) database, administered by the National Institutes of Health. In the second step, the microarray data generated from Study 1 and archived data from eight (8) samples generated in Study 3 (see Tables 1-1 and 1-3) were used. The expression profile of hUTC was compared with that of (1) human PBMC and (2) rat PBMC. The expression profile of human PBMC was obtained from healthy human subjects (NCBI database study GSE14642), while the expression profile of rat PBMC was obtained from NCBI database studies GSE11083 and GSE19537. Expression profiles of subtypes of human blood cells (B cell, NK cell, dendritic cell, lymphoid T cell, myeloid monocyte and neutrophils) were also obtained from NCBI databases (study GSE22886 and study GSE3982). Additionally, mining the Gene Ontology and Entrez databases identified 3976 human plasma membrane protein genes (GO:0005886), 355 cell surface protein genes (GO:0009986) and 349 CD antigen genes. A subset of 2614 human and rat plasma membrane protein genes and 288 cell surface protein genes were matched to genes on the human and rat microarrays and 315 CD antigen genes and were matched to human microarrays were included for this study.

Based on the dynamics of the expression signal, i.e., log 2 (intensity) of greater or equal to ten as threshold for high expression signals for all the datasets, a list of 314 probe sets from over 200 genes that are highly expressed in both types of samples were identified. In both cases, genes whose expression in hUTC was dramatically different from that of human PBMC were selected and rank ordered. Table 1-4 shows the list of genes, generated in Study 2, whose expression levels were significantly different between hUTC and that of human PBMC. These include cell surface and plasma membrane proteins as well as intracellular proteins.

In Table 1-4, genes that were identified in all three sets of samples are underlined. Genes that were examined in more detail are bolded (they include DKK3, LAMB1, ANPEP (CD13), LAMP1 (CD107a), PTPRC (CD45), MME (CD10) and NRP1).

TABLE 1-4

List of genes whose expression levels were significantly different between hUTC and that of human PBMC in Study 2 samples

| Gene Symbol | Entrez Gene | Gene Title |
|---|---|---|
| KRT19 | 3880 | Keratin 19 |
| DKK3 | 27122 | Dickkopf homolog 3 (*Xenopus laevis*) |
| GJA1 | 2697 | Gap junction protein, alpha 1, 43 kDa |
| LOX | 4015 | Lysyl oxidase |
| FBN1 | 2200 | Fibrillin 1 |
| COL3A1 | 1281 | Collagen, type III, alpha 1 |
| TPM2 | 7169 | Tropomyosin 2 (beta) |
| COL1A1 | 1277 | Collagen, type I, alpha 1 |
| CYR61 | 3491 | Cysteine-rich, angiogenic inducer, 61 |
| DKK1 | 22943 | Dickkopf homolog 1 (*Xenopus laevis*) |
| CTGF | 1490 | Connective tissue growth factor |
| DCBLD2 | 131566 | Discoidin, CUB and LCCL domain containing |
| ITGB5 | 3693 | Integrin, beta 5 |
| COL5A1 | 1289 | Collagen, type V, alpha 1 |
| THY1 | 7070 | Thy-1 cell surface antigen |
| FTL | 2512 | Ferritin, light polypeptide |
| NNMT | 4837 | Nicotinamide N-methyltransferase |
| TMEM47 | 83604 | Transmembrane protein 47 |
| CDH11 | 1009 | Cadherin 11, type 2, OB-cadherin (osteoblast) |
| SPTBN1 | 6711 | Spectrin, beta, non-erythrocytic 1 |
| RPS19 | 6223 | Ribosomal protein S19 |
| DCN | 1634 | Decorin |
| RPS20 | 6224 | Ribosomal protein S20 |
| LAMB1 | 3912 | Laminin, beta 1 |
| COL5A2 | 1290 | Collagen, type V, alpha 2 |
| SERPINE2 | 5270 | Terpin peptidase inhibitor, clade E (nexin) |
| TPBG | 7162 | Trophoblast glycoprotein |
| CLMP | 79827 | CXADR-like membrane protein |
| MAP1B | 4131 | Microtubule-associated protein 1B |
| SLIT2 | 9353 | Slit homolog 2 (*Drosophila*) |
| FRMD6 | 122786 | FERM domain containing 6 |
| CSPG4 | 1464 | Chondroitin sulfate proteoglycan 4 |
| PLOD2 | 5352 | Procollagen-lysine, 2-oxoglutarate 5-dioxygenase 2 |
| CDH2 | 1000 | Cadherin 2, type 1, N-cadherin (neuronal) |
| COL1A2 | 1278 | Collagen, type I, alpha 2 |
| FAT1 | 2195 | FAT tumor suppressor homolog 1 (*Drosophila*) |
| GNG12 | 55970 | Guanine nucleotide binding protein (G protein), gamma 12 |
| FGG | 2266 | Fibrinogen gamma chain |
| SULF1 | 23213 | Sulfatase 1 |
| ANTXR1 | 84168 | Anthrax toxin receptor 1 |
| PAPPA | 5069 | PAPPA antisense RNA (non-protein coding) |
| MFAP5 | 8076 | Microfibrillar associated protein 5 |
| SSTR1 | 6751 | Somatostatin receptor 1 |
| CAP2 | 10486 | CAP, adenylate cyclase-associated protein, |
| EDIL3 | 10085 | EGF-like repeats and discoidin I-like domains |
| TEK | 7010 | TEK tyrosine kinase, endothelial |
| YAP1 | 10413 | Yes-associated protein 1 |
| PTRF | 284119 | Polymerase I and transcript release factor |
| LUM | 4060 | lumican |
| WWTR1 | 25937 | WW domain containing transcription regulator |
| NR2F2 | 7026 | nuclear receptor subfamily 2, group F, member |
| ANPEP (CD13) | 290 | alanyl (membrane) aminopeptidase |
| LAMP1 (CD107a) | 3916 | lysosomal-associated membrane protein 1 |
| PTPRC (CD45) | 5788 | protein tyrosine phosphatase, receptor type, C |
| MME (CD10) | 4311 | matrix metallo proteasr |
| NRP1 | 8829 | neuropilin 1 |

Table 1-5 shows the list of genes (generated in Study 1 and Study 2), whose expression levels were significantly different between hUTC and that of human PBMC. In Table 1-5, underlining indicates genes that were identified in all three sets of samples, i.e., Study 1, 2, and 3 (they include LAMB1, DKK3 and CAP2). Genes that were examined in more detail are bolded (they include ANPEP (CD13), LAMP1 (CD107a), PTPRC (CD45), MME (CD10) and NRP1).

TABLE 1-5

List of genes whose expression levels were significantly different between hUTC and that of human PBMC in samples generated for Study 2 and 3

| Gene Symbol | Entrees Gene | Gene Title |
| --- | --- | --- |
| LAMB1 | 3912 | laminin, beta 1 |
| LUM | 4060 | Lumican |
| WWTR1 | 25937 | WW domain containing transcription regulator |
| DKK3 | 27122 | dickkopf homolog 3 (Xenopus laevis) |
| NR2F2 | 7026 | nuclear receptor subfamily 2, group F, member |
| CAP2 | 10486 | CAP, adenylate cyclase-associated protein, 2 |
| ANPEP (CD13) | 290 | alanyl (membrane) aminopeptidase |
| LAMP1 (CD107a) | 3916 | lysosomal-associated membrane protein 1 |
| PTPRC (CD45) | 5788 | protein tyrosine phosphatase, receptor type, C |
| MME (CD10) | 4311 | matrix metallo protease |
| NRP1 | 8829 | neuropilin 1 |

As shown in Table 1-5, eleven genes were identified by analysis of sample sets comprising of Study 2 and 3, including three genes that were identified in all three sets of samples. Of these eleven genes, seven genes (NRP1, DKK3, LAMP1, LAMB1, MME (CD10), PTPRC (CD45) and ANPEP (CD13)) were examined in more detail.

Of these seven genes, NRP1, DKK3, LAMP1, LAMB1 and MME (CD10) are cell surface markers while the expressed proteins, PTPRC (CD45) and ANPEP (CD13) are localized intracellularly. The expression levels of three genes, namely, PTPRC (CD45) (gene ID #207238), MME (CD10) (gene ID #203434) and ANPEP (CD13) (gene ID #202888) in hUTC and in various types of human blood cells that are PBMC were compared. This comparison of expression of cell surface protein genes, PTPRC (CD45), MME (CD10), and ANPEP (CD13) in hUTC and in various types of blood cells that comprise human PBMC is shown in FIGS. 2A, B, and C, respectively.

Example 2

RT-PCR Confirmation of Identified Markers

The transcription levels of selected genes in hUTC and human PBMC identified in Example 1 were then confirmed by RT-PCR. The results of the RT-PCR of select genes whose expression in hUTC was compared to that of human PBMC are shown in FIG. 3.

To obtain these results, total RNA from each hUTC preparation was isolated from which cDNA was then prepared. Fluorescent probes specific for each gene were then used to perform the RT-PCR reaction using the cDNA as the template.

Figure 3:
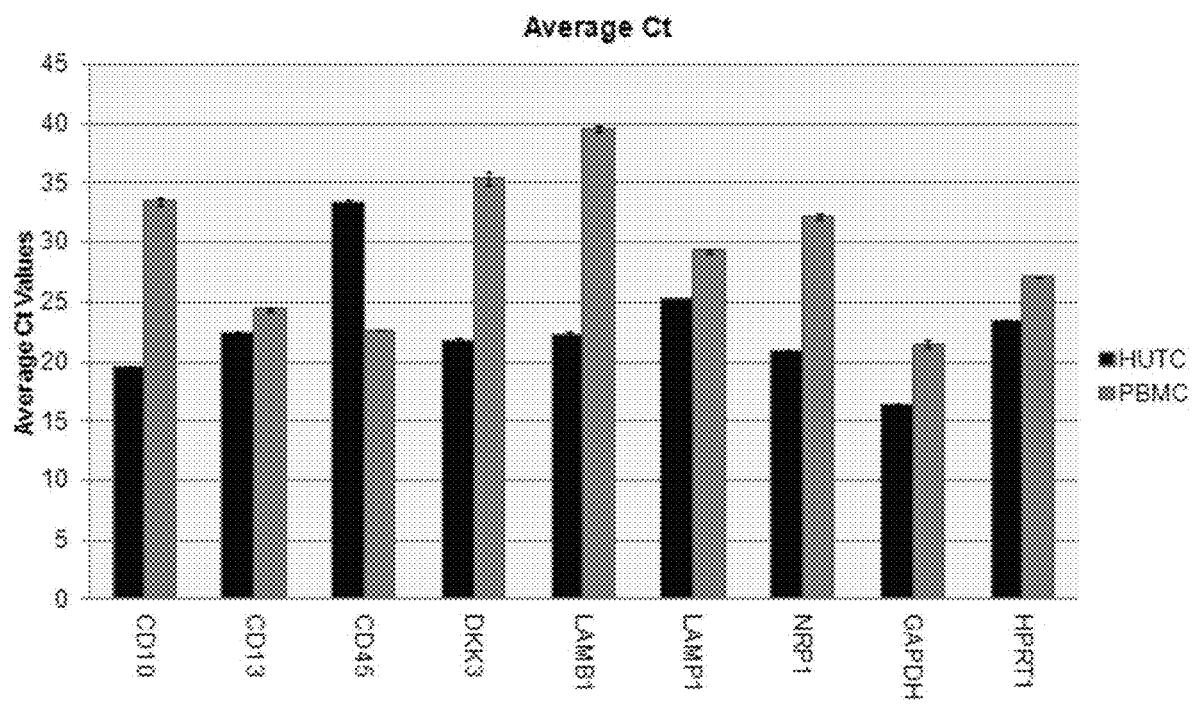
FIG. 3 shows RT-PCR analysis of select genes whose expression in hUTC is higher than that of human PBMC.

FIG. 3 shows the results of RT-PCR for MME (CD10), ANPEP (CD13), PTPRC (CD45), DKK3, LAMB1, NRP1, GAPPD, and HPRT1 in hUTC and PBMC. With the exception of the housekeeping genes, GAPDH and HPRT, all the genes tested show a greater abundance in hUTC as compared to human PBMC. Only the expression of PTPRC (CD45), which was used as a negative control and which is known to be expressed highly in human PBMC, was less abundant in hUTC. With reference to FIG. 3, a higher CT value is indicative of a lower amount of transcript.

Figure 2B:
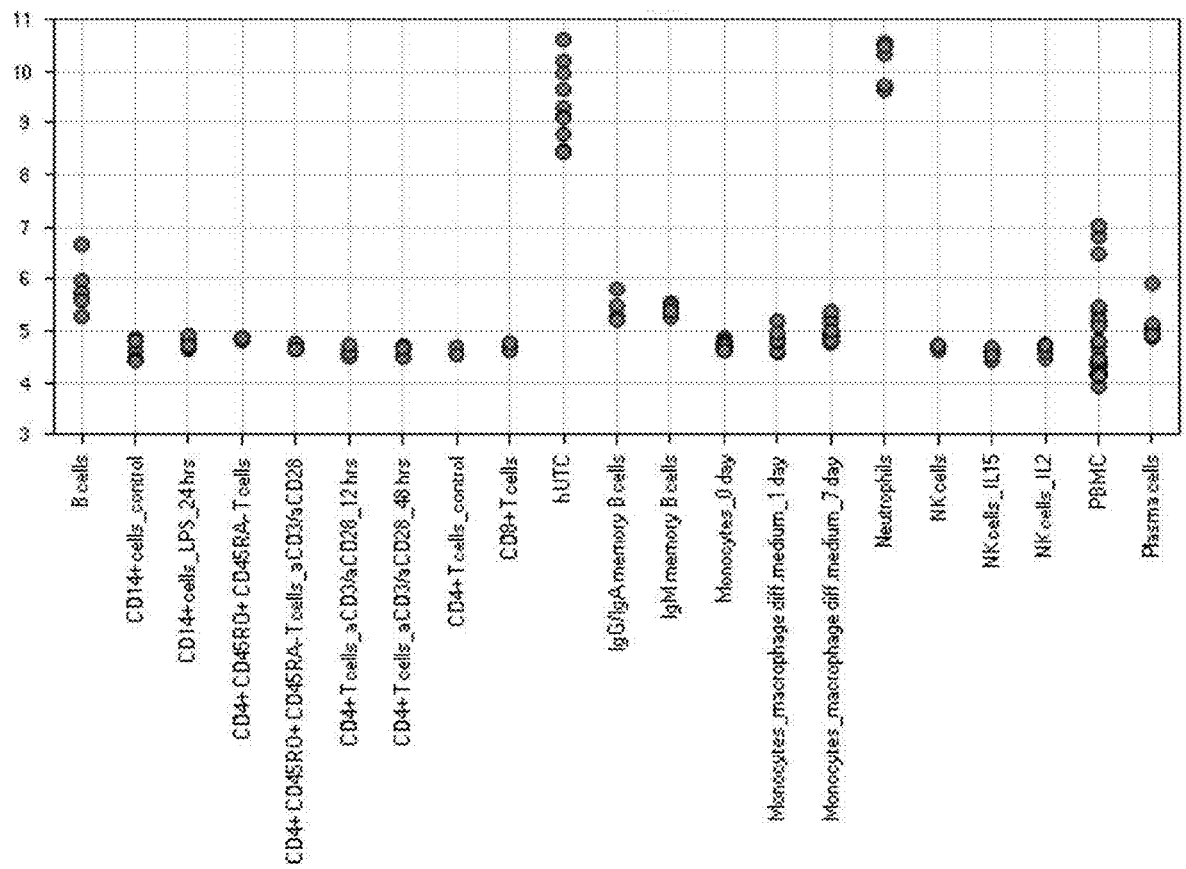
FIG. 2B shows a comparison of expression of MME (CD10) gene in hUTC and in various types of blood cells that comprise of human peripheral blood mononuclear cell (PBMC).
Figure 2C:
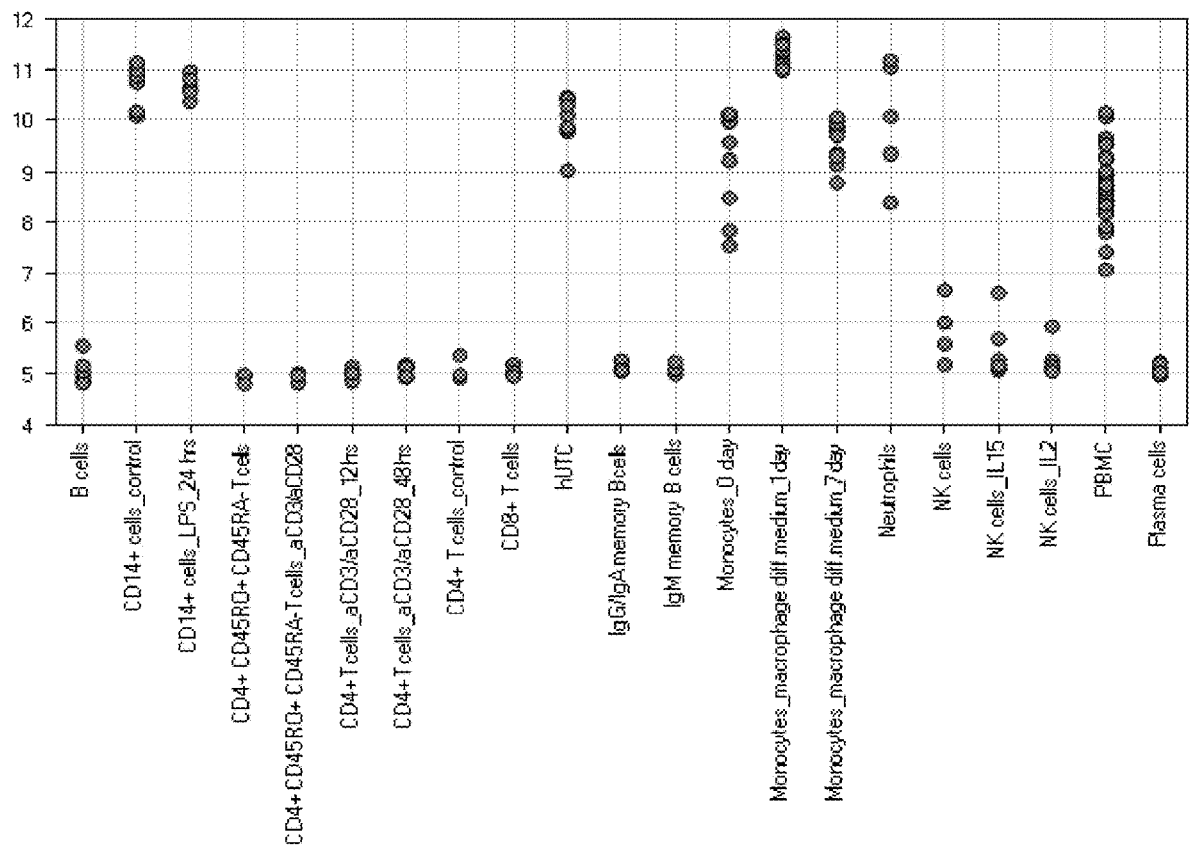
FIG. 2C shows a comparison of expression of ANPEP (CD13) gene in hUTC and in various types of blood cells that comprises of human PBMC.

Since PBMC is comprised of various types of blood cells, the gene expression profiles of select genes expressed in each of these cell types to that of hUTC were compared. As shown in FIG. 2B, while the relative expression of MME (CD10) in PBMC is low when compared to that of hUTC, its relative expression in neutrophil is high. Similarly, while the expression of ANPEP (CD13) in hUTC is comparable to that of human PBMC (see FIG. 2C), its relative expression in T-cells and macrophages is higher than that of hUTC.

Example 3

Detection of hUTC in PBMC by Flow Cytometry

From the list of genes that show differential expression in hUTC and human PBMC (see Tables 1-4 and 1-5), a subset of five genes that express the gene product on cell surface and/or plasma membrane were selected. Additionally, two genes that express the corresponding protein products intracellularly were selected. These markers included NRP1, DKK3, LAMB, LAMP1, MME (CD10), PTPRC (CD45), and ANPEP (CD13).

For the flow cytometry assay, the cells were harvested in the exponential phase and subsequently, fixed and permeablized using a kit purchased from BD Bioscience. An aliquot of this preparation was then incubated with antibodies against selected markers identified to be present on hUTC surface, namely, CD10, CD13, CD45, NRP1, and LAMP1. After removing excess antibody, the cells were incubated with a fluorescently labeled secondary antibody. Cells were then analyzed by a flow cytometer.

Figure 4A:
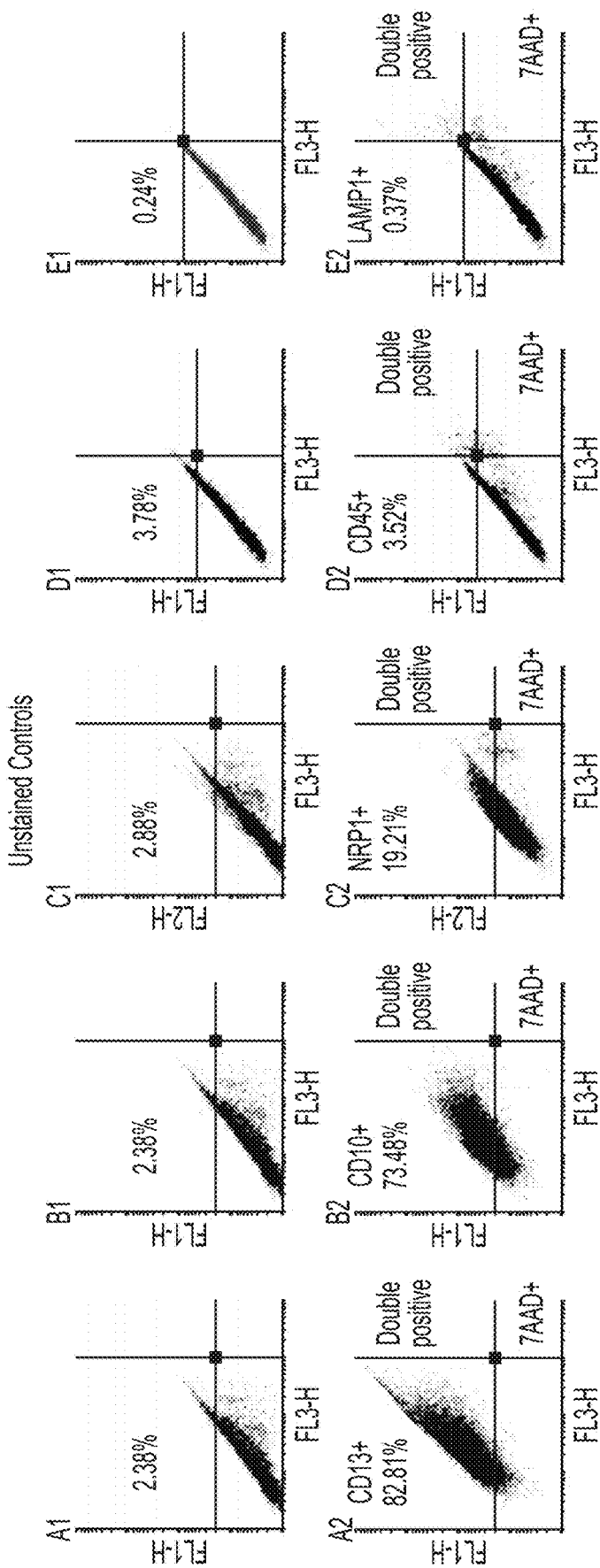
FIG. 4A shows the results of a flow cytometry assay for the detection of cell surface markers in hUTC.
Figure 4B:
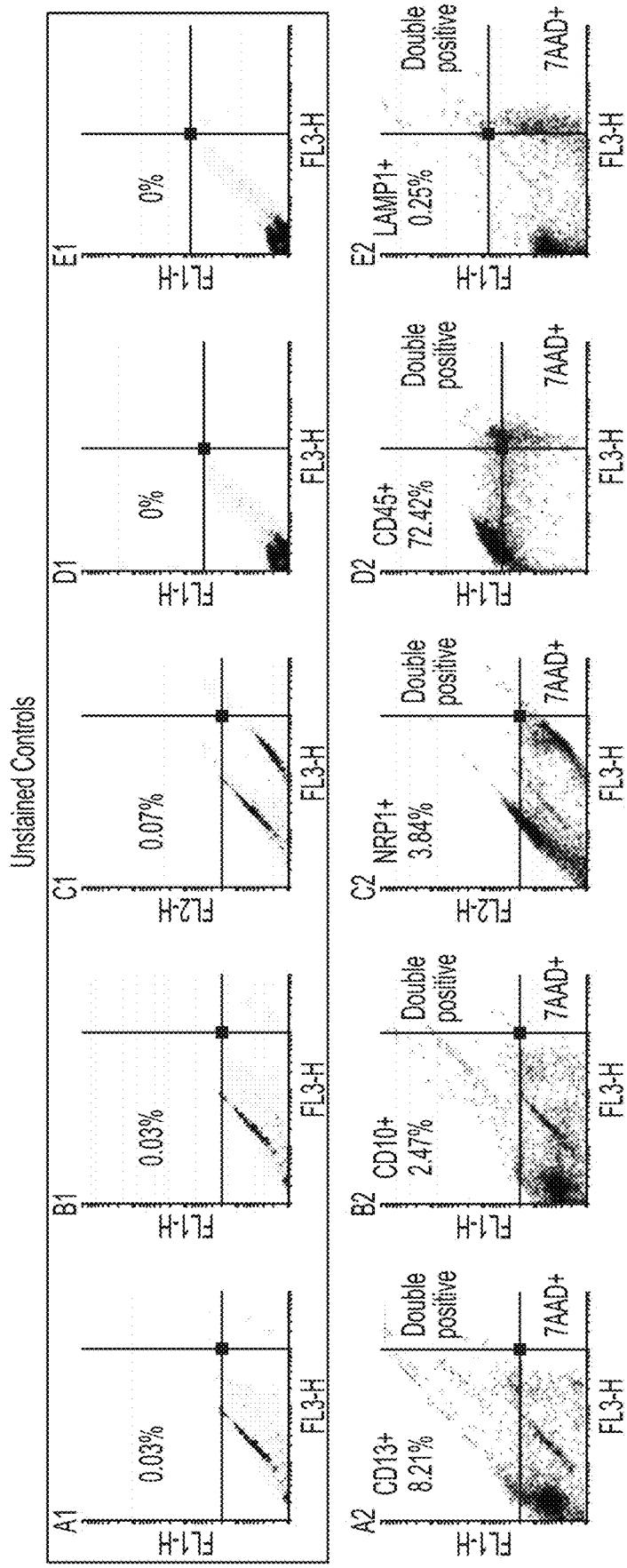
FIG. 4B shows the results of a flow cytometry assay for the detection of cell surface markers in human PBMC.
Figure 4C:
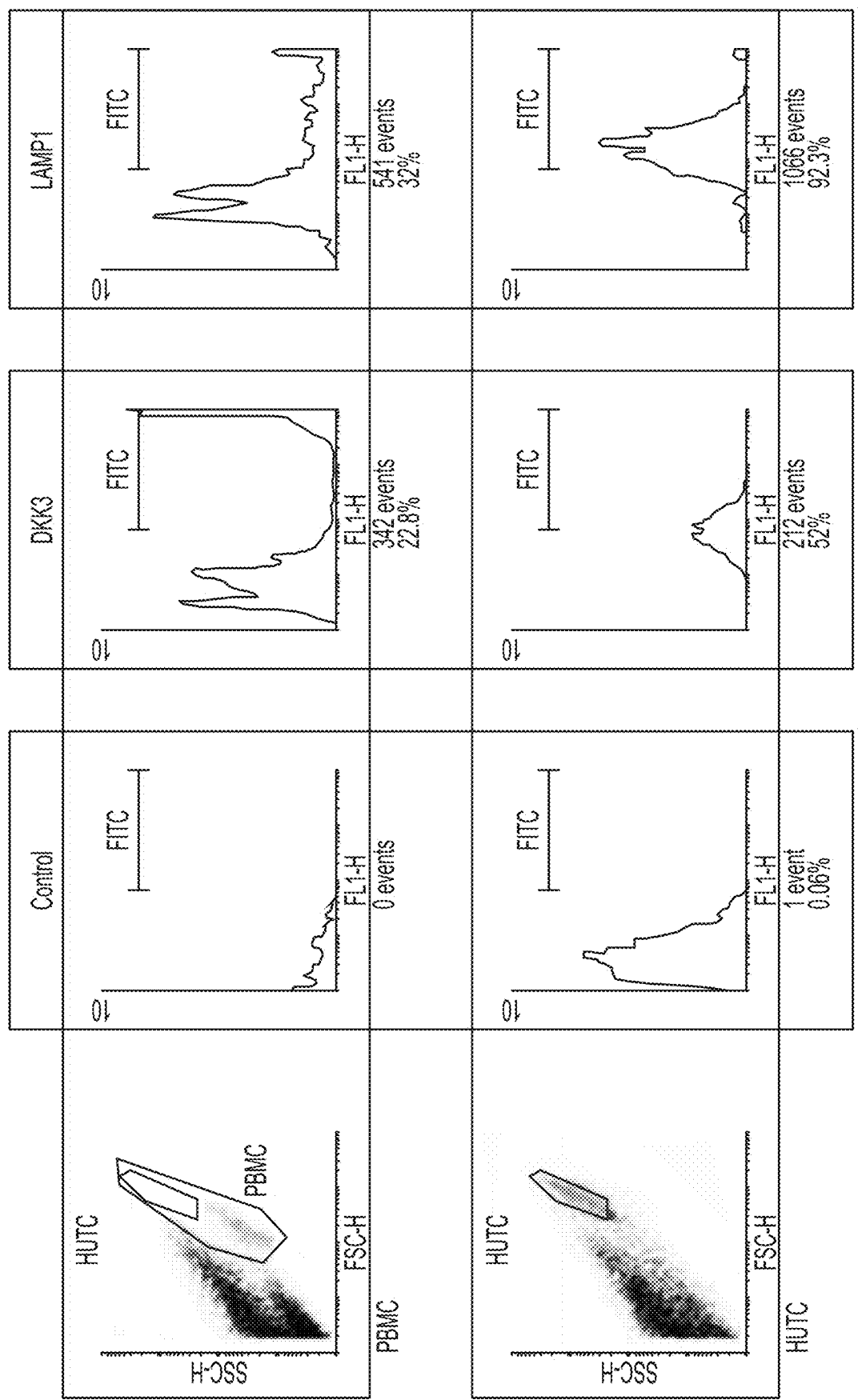
FIG. 4C shows the results for a flow cytometry assay for the detection of the internal markers DKK3 and LAMP1 in PBMC and hUTC.

The results for the flow cytometry assay for the detection of cell surface, plasma membrane, and intracellular markers are shown in FIGS. 4A to 4C. FIG. 4A shows the cell surface markers that were tested using hUTC with the top panel being the control. FIG. 4B shows the cell surface markers that were tested using PBMC with the top panel being the control. FIG. 4C shows the results for a flow cytometry assay for the detection of the internal markers DKK3 and LAMP1 in PBMC and hUTC.

With reference to FIG. 4A, 90% of the hUTC population was observed to be CD13 positive (CD13$^+$), 75% of the hUTC population was observed to be CD10 positive (CD10$^+$), and 17% of the hUTC population was observed to be NRP1 positive (NRP1$^+$). None of the hUTC population was observed to be positive for CD45 or LAMP1.

With reference to FIG. 4B, 6% of the PBMC population was observed to be CD13 positive (CD13$^+$), 2% of the PBMC population was observed to be CD10 positive (CD10$^+$), 4% of the PBMC population was observed to be NRP1 positive (NRP1$^+$), and 72% of the PBMC population was observed to be CD45 positive (CD45$^+$). None of the PBMC population was observed to be positive for LAMP1.

With reference to FIG. 4C, flow cytometry data for the intracellular markers DKK3 and LAMP1 is shown. 52% of the hUTC population was observed to be DKK3 positive. 23% of the PBMC population was observed to be DKK3 positive. FIG. 4C indicates that LAMP1 is a good internal marker for hUTC.

With the exception of NRP1, the cell surface protein gene markers could be used to detect intact, live hUTC in mixed samples containing PBMCs in serum (see FIGS. 4A and 4B). Even though NRP1 is transcribed at higher levels in hUTC as compared to that of human PBMC (FIG. 3), NRP1 could not be detected in hUTC by flow cytometry (see FIG.

4A). With respect to CD45, as expected, high levels of CD45 were being expressed on the surface of live human PBMC only (see FIG. 4B). Additionally, two intracellular markers LAMP1 and DKK3 (from the list of differentially expressed genes, Table 1-4) whose expression is higher in hUTC as compared to human PBMC) were also examined (see FIG. 4C). These markers can be used as additional confirmation for hUTC identity.

The differences between hUTC and human PBMC as assayed by flow cytometry are shown in Table 3-1 below.

TABLE 3-1

Difference between hUTC and PBMC with respect to percent positive cells as assayed by flow cytometry.

| Population | % CD13 | % CD10 | % NRP1 | % CD45 | % LAMP1 | % DKK3 | % LAMB |
|---|---|---|---|---|---|---|---|
| hUTC | 90 | 70-90 | 17 | 0 | 92 | 52 | ND |
| PBMC | 6 | 2 | 4 | 45 | 32 | 23 | ND |

Table 3-2 below summarizes the differences between hUTC and PBMC as assayed by RT-PCR in Example 2 above and by flow cytometry in the instant Example. In Table 3-2, Nd means Not determined.

TABLE 3-2

Summary of RT-PCR and flow cytometry results

| | Microarray Analysis | | RT-PCR | | Flow Analysis surface | | Flow Analysis intracellular | |
|---|---|---|---|---|---|---|---|---|
| | hUTC | PBMC | hUTC | PBMC | hUTC | PBMC | hUTC | PBMC |
| MME (CD10) | + | − | + | − | + | − | Nd | Nd |
| ANPEP (CD13) | + | + | + | + | + | − | Nd | Nd |
| PTPRC (CD45) | − | + | − | + | − | + | Nd | Nd |
| LAMP1 | + | + | + | + | − | − | + | − |
| NRP1 | + | − | + | − | − | − | Nd | Nd |
| DKK3 | + | − | + | − | Nd | Nd | ++ | + |
| LAMB1 | + | + | + | − | Nd | Nd | Nd | Nd |

Example 4

Detection of hUTC in a Mixture of hUTC and Human PBMC

To demonstrate detection of hUTC in blood, various concentrations of hUTC were mixed with 1 million human PBMC. The mixture was then analyzed by flow cytometry using CD45 (positive marker for PBMC), CD10 and CD13 (positive markers for hUTC). In particular, the detection of hUTC in a mixture comprising of hUTC (ranging from 1,500 cells/ml to 110,000 cells/ml) and human PBMC (1 million cells/ml) is shown in FIGS. 5A and 5B.

The two types of cells were mixed in 1 ml of human serum at room temperature. Immediately thereafter, aliquots of the mixture were analyzed by flow cytometry using CD10 as a marker for hUTC and CD45 as a marker for PBMC. In FIG. 5A, the concentration of hUTC ranged from 1,500 to 1,700 cells/ml and that of human PBMC was 1 million cells/ml. In FIG. 5B, the concentration of hUTC ranged from 1,700 to 110,000 cells/ml and that of human PBMC was 1 million cells/ml.

Figure 5A:
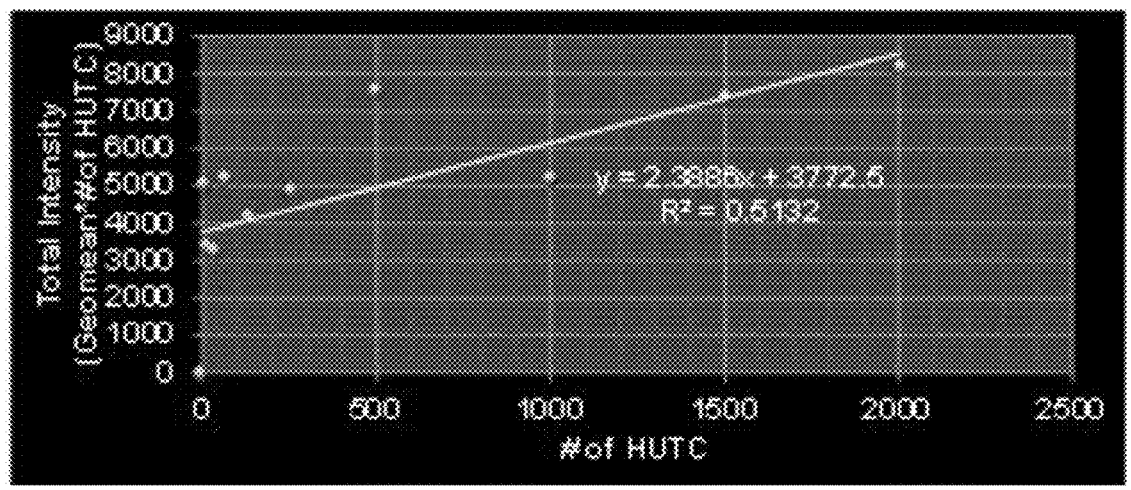
FIG. 5A shows the detection of hUTC in a mixture comprising of hUTC (ranging from 1,500-1,700 cells/ml) and human PBMC (1 million cells/ml) in the presence of 1 ml of human serum using flow cytometry.
Figure 5B:
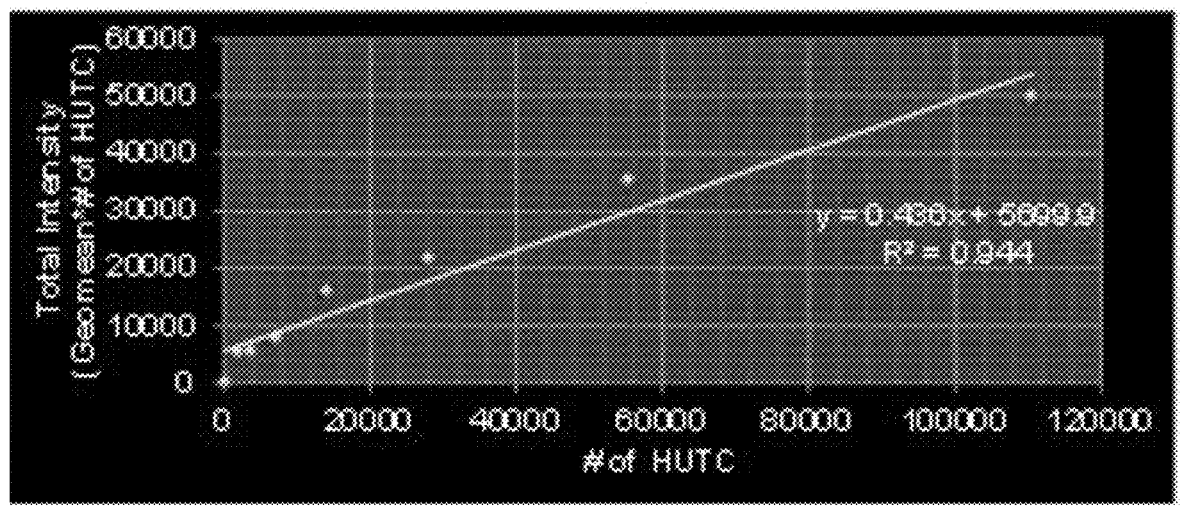
FIG. 5B shows the detection of hUTC in a mixture comprising of hUTC (ranging from 1,700 to 110,000 cells/ml) and human PBMC (1 million cells/ml) in the presence of 1 ml of human serum using flow cytometry.

As can be seen from FIG. 5A, if the sample contains 1,700 or more hUTC/ml in the presence of 1 million human PBMC, then the accuracy of determination using flow cytometry is high ($R^2=0.94$). If the sample contains 1,500 to 1,700 hUTC/ml in the presence of 1 million human PBMC (FIG. 5B), then the accuracy of determination using flow cytometry is lower ($R^2=0.51$).

Example 5

Isolation of hUTC

Umbilical Cell Isolation.

Umbilical cords were obtained from National Disease Research Interchange (NDRI, Philadelphia, Pa.). The tissues were obtained following normal deliveries. The cell isolation protocols were performed aseptically in a laminar flow hood. To remove blood and debris, the cord was washed in phosphate buffered saline (PBS; Invitrogen, Carlsbad, Calif.) in the presence of penicillin at 100 U/ml, streptomycin at 100 mg/ml and amphotericin B at 0.25 µg/ml (Invitrogen Carlsbad, Calif.). The tissues were then mechanically dissociated in 150 cm² tissue culture plates in the presence of 50 ml of medium (DMEM-low glucose or DMEM-high glucose; Invitrogen) until the tissue was minced into a fine pulp. The chopped tissues were transferred to 50 ml conical tubes (approximately 5 g of tissue per tube).

The tissue was then digested in either DMEM-low glucose medium or DMEM-high glucose medium, each containing penicillin at 100 U/ml, streptomycin at 100 mg/ml, amphotericin B at 0.25 µg/ml and the digestion enzymes. In some experiments an enzyme mixture of collagenase and dispase was used ("C:D") (collagenase (Sigma, St Louis, Mo.), 500 U/ml; and dispase (Invitrogen), 50 U/ml, in DMEM-Low glucose medium). In other experiments a mixture of collagenase, dispase and hyaluronidase ("C:D:H") was used (C:D:H=collagenase, 500 U/ml; dispase, 50 U/ml; and hyaluronidase (Sigma), 5 U/ml, in DMEM-Low glucose). The conical tubes containing the tissue, medium and digestion enzymes were incubated at 37° C. in an orbital shaker (Environ, Brooklyn, N.Y.) at 225 rpm for 2 hours.

After digestion, the tissues were centrifuged at 150×g for 5 minutes, the supernatant was aspirated. The pellet was resuspended in 20 ml of growth medium (DMEM:Low glucose (Invitrogen), 15% (v/v) fetal bovine serum (FBS; defined fetal bovine serum; Lot # AND18475; Hyclone, Logan, Utah), 0.001% (v/v) 2-mercaptoethanol (Sigma), penicillin at 100 U/ml, streptomycin at 100 µg/ml, and amphotericin B at 0.25 µg/ml (each from Invitrogen, Carlsbad, Calif.)). The cell suspension was filtered through a 70 µm nylon BD FALCON Cell Strainer (BD Biosciences, San Jose, Calif.). An additional 5 ml rinse comprising growth medium was passed through the strainer. The cell suspension was then passed through a 40-µm nylon cell strainer (BD Biosciences, San Jose, Calif.) and chased with a rinse of an additional 5 ml of growth medium.

The filtrate was resuspended in growth medium (total volume 50 ml) and centrifuged at 150×g for 5 minutes. The supernatant was aspirated and the cells were resuspended in 50 ml of fresh growth medium. This process was repeated twice more.

After the final centrifugation, supernatant was aspirated and the cell pellet was resuspended in 5 ml of fresh growth medium. The number of viable cells was determined using trypan blue staining. Cells were then cultured under standard conditions.

The cells isolated from umbilical cord tissues were seeded at 5,000 cells/cm$^2$ onto gelatin-coated T-75 flasks (Corning Inc., Corning, N.Y.) in growth medium. After two days, spent medium and unadhered cells were aspirated from the flasks. Adherent cells were washed with PBS three times to remove debris and blood-derived cells. Cells were then replenished with growth medium and allowed to grow to confluence (about 10 days from passage 0 to passage 1). On subsequent passages (from passage 1 to 2 etc.), cells reached sub-confluence (75-85% confluence) in 4-5 days. For these subsequent passages, cells were seeded at 5,000 cells/cm$^2$. Cells were grown in a humidified incubator with 5% carbon dioxide at 37° C.

In some experiments, cells were isolated from postpartum tissues in DMEM-low glucose medium after digestion with LIBERASE (2.5 mg/ml, Blendzyme 3; Roche Applied Sciences, Indianapolis, Ind.) and hyaluronidase (5 U/ml, Sigma). Digestion of the tissue and isolation of the cells was as described for other protease digestions above, however, the LIBERASE/hyaluronidase mixture was used instead of the C:D or C:D:H enzyme mixture. Tissue digestion with LIBERASE resulted in the isolation of cell populations from postpartum tissues that expanded readily.

Procedures were compared for isolating cells from the umbilical cord using differing enzyme combinations. Enzymes compared for digestion included: i) collagenase; ii) dispase; iii) hyaluronidase; iv) collagenase: dispase mixture (C:D); v) collagenase:hyaluronidase mixture (C:H); vi) dispase:hyaluronidase mixture (D:H); and vii) collagenase: dispase:hyaluronidase mixture (C:D:H). Differences in cell isolation utilizing these different enzyme digestion conditions were observed (see Table 5-1).

Other attempts were made to isolate pools of cells from umbilical cord by different approaches. In one instance, umbilical cord was sliced and washed with growth medium to dislodge the blood clots and gelatinous material. The mixture of blood, gelatinous material and growth medium was collected and centrifuged at 150×g. The pellet was resuspended and seeded onto gelatin coated flasks in growth medium. From these experiments, a cell population was isolated that readily expanded.

Cells have also been isolated from cord blood samples obtained from NDRI. The isolation protocol used was that of International Patent Application PCT/US2002/029971 by Ho et al. Samples (50 ml and 10.5 ml, respectively) of umbilical cord blood (NDRI, Philadelphia Pa.) were mixed with lysis buffer (filter-sterilized 155 mM ammonium chloride, 10 millimolar potassium bicarbonate, 0.1 mM EDTA buffered to pH 7.2 (all components from Sigma, St. Louis, Mo.)). Cells were lysed at a ratio of 1:20 cord blood to lysis buffer. The resulting cell suspension was vortexed for 5 seconds, and incubated for 2 minutes at ambient temperature. The lysate was centrifuged (10 minutes at 200×g). The cell pellet was resuspended in Complete Minimal Essential Medium (Gibco, Carlsbad Calif.) containing 10% fetal bovine serum (Hyclone, Logan Utah), 4 mM glutamine (Mediatech Herndon, Va.), penicillin at 100 U/ml and streptomycin at 100 µg/ml (Gibco, Carlsbad, Calif.). The resuspended cells were centrifuged (10 minutes at 200×g), the supernatant was aspirated, and the cell pellet was washed in complete medium. Cells were seeded directly into either T75 flasks (Corning, N.Y.), T75 laminin-coated flasks, or T175 fibronectin-coated flasks (both Becton Dickinson, Bedford, Mass.).

To determine whether cell populations could be isolated under different conditions and expanded under a variety of conditions immediately after isolation, cells were digested in growth medium with or without 0.001% (v/v) 2-mercaptoethanol (Sigma, St. Louis, Mo.), using the enzyme combination of C:D:H, according to the procedures provided above. All cells were grown in the presence of penicillin at 100 U/ml and streptomycin at 100 µg/ml. Under all tested conditions, cells attached and expanded well between passage 0 and 1 (Table 4-2). Cells in conditions 5-8 and 13-16 were demonstrated to proliferate well up to 4 passages after seeding, at which point they were cryopreserved.

The combination of C:D:H, provided the best cell yield following isolation, and generated cells that expanded for many more generations in culture than the other conditions (Table 5-1). An expandable cell population was not attained using collagenase or hyaluronidase alone. No attempt was made to determine if this result is specific to the collagenase that was tested.

TABLE 5-1

Isolation of cells from umbilical cord tissue using varying enzyme combinations

| Enzyme Digest | Cells Isolated | Cell Expansion |
|---|---|---|
| Collagenase | X | X |
| Dispase | + (>10 h) | + |
| Hyaluronidase | X | X |
| Collagenase:Dispase | ++ (<3 h) | ++ |
| Collagenase:Hyaluronidase | ++ (<3 h) | + |
| Dispase:Hyaluronidase | + (>10 h) | + |
| Collagenase:Dispase:Hyaluronidase | +++ (<3 h) | +++ |

Key: + = good,
++ = very good,
+++ = excellent,
X = no success

Cells attached and expanded well between passage 0 and 1 under all conditions tested for enzyme digestion and growth (Table 5-2). Cells in experimental conditions 5-8 and 13-16 proliferated well up to four passages after seeding, at which point they were cryopreserved. All cells were cryopreserved for further analysis.

TABLE 5-2

Isolation and culture expansion of postpartum cells under varying conditions

| Condition | Medium | 15% FBS | BME | Gelatin | 20% O$_2$ | Growth Factors |
|---|---|---|---|---|---|---|
| 1 | DMEM-Lg | Y | Y | Y | Y | N |
| 2 | DMEM-Lg | Y | Y | Y | N (5%) | N |

TABLE 5-2-continued

Isolation and culture expansion of postpartum cells under varying conditions

| Condition | Medium | 15% FBS | BME | Gelatin | 20% O$_2$ | Growth Factors |
|---|---|---|---|---|---|---|
| 3 | DMEM-Lg | Y | Y | N | Y | N |
| 4 | DMEM-Lg | Y | Y | N | N (5%) | N |
| 5 | DMEM-Lg | N (2%) | Y | N (Laminin) | Y | EGF/FGF (20 ng/ml) |
| 6 | DMEM-Lg | N (2%) | Y | N (Laminin) | N (5%) | EGF/FGF (20 ng/ml) |
| 7 | DMEM-Lg | N (2%) | Y | N (Fibronectin) | Y | PDGF/VEGF |
| 8 | DMEM-Lg | N (2%) | Y | N (Fibronectin) | N (5%) | PDGF/VEGF |
| 9 | DMEM-Lg | Y | N | Y | Y | N |
| 10 | DMEM-Lg | Y | N | Y | N (5%) | N |
| 11 | DMEM-Lg | Y | N | N | Y | N |
| 12 | DMEM-Lg | Y | N | N | N (5%) | N |
| 13 | DMEM-Lg | N (2%) | N | N (Laminin) | Y | EGF/FGF (20 ng/ml) |
| 14 | DMEM-Lg | N (2%) | N | N (Laminin) | N (5%) | EGF/FGF (20 ng/ml) |
| 15 | DMEM-Lg | N (2%) | N | N (Fibronectin) | Y | PDGF/VEGF |
| 16 | DMEM-Lg | N (2%) | N | N (Fibronectin) | N (5%) | PDGF/VEGF |

Nucleated cells attached and grew rapidly. These cells were analyzed by flow cytometry and were similar to cells obtained by enzyme digestion.

The preparations contained red blood cells and platelets. No nucleated cells attached and divided during the first 3 weeks. The medium was changed 3 weeks after seeding and no cells were observed to attach and grow.

Populations of cells could be isolated from umbilical tissue efficiently using the enzyme combination collagenase (a metalloprotease), dispase (neutral protease) and hyaluronidase (mucolytic enzyme which breaks down hyaluronic acid). LIBERASE, which is a blend of collagenase and a neutral protease, may also be used. Blendzyme 3, which is collagenase (4 Wunsch U/g) and thermolysin (1714 casein U/g), was also used together with hyaluronidase to isolate cells. These cells expanded readily over many passages when cultured in growth expansion medium on gelatin coated plastic.

Cells were also isolated from residual blood in the cords, but not cord blood. The presence of cells in blood clots washed from the tissue, which adhere and grow under the conditions used, may be due to cells being released during the dissection process.

Example 6

Karyotype Analysis of Cells

Cell lines used in cell therapy are preferably homogeneous and free from any contaminating cell type. Human cells used in cell therapy should have a normal number (46) of chromosomes with normal structure. To identify umbilicus-derived cell lines that are homogeneous and free from cells of non-umbilical tissue origin, karyotypes of cell samples were analyzed.

UTC from postpartum tissue of a male neonate were cultured in growth media. Postpartum tissue from a male neonate (X,Y) was selected to allow distinction between neonatal-derived cells and maternal derived cells (X,X). Cells were seeded at 5,000 cells per square centimeter in growth medium in a T25 flask (Corning, Corning, N.Y.) and expanded to 80% confluence. A T25 flask containing cells was filled to the neck with growth media. Samples were delivered to a clinical cytogenetics lab by courier (estimated lab to lab transport time is one hour). Chromosome analysis was performed by the Center for Human & Molecular Genetics at the New Jersey Medical School, Newark, N.J. Cells were analyzed during metaphase when the chromosomes are best visualized. Of twenty cells in metaphase counted, five were analyzed for normal homogeneous karyotype number (two). A cell sample was characterized as homogeneous if two karyotypes were observed. A cell sample was characterized as heterogeneous if more than two karyotypes were observed. Additional metaphase cells were counted and analyzed when a heterogeneous karyotype number (four) was identified.

All cell samples sent for chromosome analysis were interpreted by the cytogenetics laboratory staff as exhibiting a normal appearance. Three of the sixteen cell lines analyzed exhibited a heterogeneous phenotype (XX and XY) indicating the presence of cells derived from both neonatal and maternal origins (Table 6-1). Each of the cell samples was characterized as homogeneous. (Table 6-1).

TABLE 6-1

Karyotype results of hUTC

| Tissue | Passage | Metaphase cells counted | Metaphase cells analyzed | Number of karyotypes | ISCN Karyotype |
|---|---|---|---|---|---|
| Umbilical | 23 | 20 | 5 | 2 | 46, XX |
| Umbilical | 6 | 20 | 5 | 2 | 46, XY |
| Umbilical | 3 | 20 | 5 | 2 | 46, XX |

Chromosome analysis identified umbilicus-derived UTC whose karyotypes appear normal as interpreted by a clinical cytogenetics laboratory. Karyotype analysis also identified cell lines free from maternal cells, as determined by homogeneous karyotype.

Example 7

Flow Cytometric Evaluation of Cell Surface Markers

Characterization of cell surface proteins or "markers" by flow cytometry can be used to determine a cell line's identity. The consistency of expression can be determined from multiple donors, and in cells exposed to different processing and culturing conditions. Postpartum cell lines isolated from the umbilicus were characterized by flow cytometry, providing a profile for the identification of these cell lines.

Cells were cultured in growth medium, in plasma-treated T75, T150, and T225 tissue culture flasks (Corning, Corning, N.Y.) until confluent. The growth surfaces of the flasks were coated with gelatin by incubating 2% (w/v) gelatin (Sigma, St. Louis, Mo.) for 20 minutes at room temperature.

Adherent cells in flasks were washed in phosphate buffered saline (PBS); (Gibco, Carlsbad, Mo.) and detached with trypsin/EDTA (Gibco). Cells were harvested, centrifuged, and resuspended in 3% (v/v) FBS in PBS at a cell concentration of $1 \times 10^7$/ml. In accordance with the manufacture's specifications, antibody to the cell surface marker of interest (see below) was added to 100 µl of cell suspension and the mixture was incubated in the dark for 30 minutes at 4° C. After incubation, cells were washed with PBS and centrifuged to remove unbound antibody. Cells were resuspended in 500 µl PBS and analyzed by flow cytometry. Flow cytometry analysis was performed with a FACS calibur instrument (Becton Dickinson, San Jose, Calif.).

The following antibodies to cell surface markers were used.

TABLE 7-1

Antibodies used in characterizing cell surface markers of UDCs.

| Antibody | Manufacturer | Catalog Number |
| --- | --- | --- |
| CD10 | BD Pharmingen (San Diego, CA) | 555375 |
| CD13 | BD Pharmingen | 555394 |
| CD31 | BD Pharmingen | 555446 |
| CD34 | BD Pharmingen | 555821 |
| CD44 | BD Pharmingen | 555478 |
| CD45RA | BD Pharmingen | 555489 |
| CD73 | BD Pharmingen | 550257 |
| CD90 | BD Pharmingen | 555596 |
| CD117 | BD Pharmingen | 340529 |
| CD141 | BD Pharmingen | 559781 |
| PDGFr-alpha | BD Pharmingen | 556002 |
| HLA-A, B, C | BD Pharmingen | 555553 |
| HLA-DR, DP, DQ | BD Pharmingen | 555558 |
| IgG-FITC | Sigma (St. Louis, MO) | F-6522 |
| IgG- PE | Sigma | P-4685 |

Umbilicus-derived cells were analyzed at passages 8, 15, and 20.

To compare differences among donors, umbilical cord tissue-derived cells from different donors were compared to each other. Umbilicus-derived cells cultured on gelatin-coated flasks were also compared to umbilicus-derived cells cultured on uncoated flasks.

Four treatments used for isolation and preparation of cells were compared. Cells derived from postpartum tissue by treatment with: 1) collagenase; 2) collagenase/dispase; 3) collagenase/hyaluronidase; and 4) collagenase/hyaluronidase/dispase were compared.

Umbilical cord-derived cells at passage 8, 15, and 20 analyzed by flow cytometry all expressed CD10, CD13, CD44, CD73, CD 90, PDGFr-alpha and HLA-A, B, C, indicated by increased fluorescence relative to the IgG control. These cells were negative for CD31, CD34, CD45, CD117, CD141, and HLA-DR, DP, DQ, indicated by fluorescence values consistent with the IgG control.

Umbilical cord-derived cells isolated from separate donors analyzed by flow cytometry each showed positive for the production of CD10, CD13, CD44, CD73, CD 90, PDGFr-alpha and HLA-A, B, C, reflected in the increased values of fluorescence relative to the IgG control. These cells were negative for the production of CD31, CD34, CD45, CD117, CD141, and HLA-DR, DP, DQ with fluorescence values consistent with the IgG control.

The umbilical cord-derived cells expanded on gelatin-coated and uncoated flasks analyzed by flow cytometry were all positive for the production of CD10, CD13, CD44, CD73, CD 90, PDGFr-alpha, and HLA-A, B, C, with increased values of fluorescence relative to the IgG control. These cells were negative for the production of CD31, CD34, CD45, CD117, CD141, and HLA-DR, DP, DQ, with fluorescence values consistent with the IgG control.

Analysis of umbilical cord-derived cells by flow cytometry has established an identity of these cell lines. These umbilical cord-derived cells are positive for CD10, CD13, CD44, CD73, CD90, PDGFr-alpha, and HLA-A,B,C; and negative for CD31, CD34, CD45, CD117, CD141 and HLA-DR, DP, DQ. This identity was consistent between variations in variables including the donor, passage, culture vessel surface coating, digestion enzymes, and placental layer. Some variation in individual fluorescence value histogram curve means and ranges were observed, but all positive curves under all conditions tested were normal and expressed fluorescence values greater than the IgG control, thus confirming that the cells comprise a homogeneous population, which has positive expression of the markers.

Example 8

Analysis of Cells by Oligonucleotide Array

Oligonucleotide arrays were used to compare gene expression profiles of umbilicus-derived and placenta-derived cells with fibroblasts, human mesenchymal stem cells, and another cell line derived from human bone marrow. This analysis provided a characterization of the postpartum-derived cells and identified unique molecular markers for these cells.

Postpartum Tissue-Derived Cells.

Human umbilical cords and placenta were obtained from National Disease Research Interchange (NDRI, Philadelphia, Pa.) from normal full term deliveries with patient consent. The tissues were received and cells were isolated as described in Example 5 after digestion with a C:D:H mixture. The cells were cultured in growth medium on gelatin-coated plastic tissue culture flasks. The cultures were incubated at 37° C. with 5% $CO_2$.

Fibroblasts.

Human dermal fibroblasts were purchased from Cambrex Incorporated (Walkersville, Md.; Lot number 9F0844) and ATCC CRL-1501 (CCD39SK). Both lines were cultured in DMEM/F12 medium (Invitrogen, Carlsbad, Calif.) with 10% (v/v) fetal bovine serum (Hyclone) and penicillin/streptomycin (Invitrogen)). The cells were grown on standard tissue-culture treated plastic.

Human Mesenchymal Stem Cells (hMSC).

hMSCs were purchased from Cambrex Incorporated (Walkersville, Md.; Lot numbers 2F1655, 2F1656 and 2F1657) and cultured according to the manufacturer's specifications in MSCGM Media (Cambrex). The cells were grown on standard tissue cultured plastic at 37° C. with 5% $CO_2$.

Human Iliac Crest Bone Marrow Cells (ICBM).

Human iliac crest bone marrow was received from NDRI with patient consent. The marrow was processed according to the method outlined by Ho, et al. (WO03/025149). The marrow was mixed with lysis buffer (155 mM $NH_4Cl$, 10 mM $KHCO_3$, and 0.1 mM EDTA, pH 7.2) at a ratio of 1 part bone marrow to 20 parts lysis buffer. The cell suspension was vortexed, incubated for 2 minutes at ambient temperature, and centrifuged for 10 minutes at 500×g. The supernatant was discarded and the cell pellet was resuspended in Minimal Essential Medium-alpha (Invitrogen) supplemented with 10% (v/v) fetal bovine serum and 4 mM glutamine. The cells were centrifuged again and the cell pellet was resuspended in fresh medium. The viable mononuclear cells were counted using trypan blue exclusion (Sigma, St. Louis, Mo.). The mononuclear cells were seeded in plastic tissue culture flasks at $5 \times 10^4$ cells/cm$^2$. The cells were incubated at 37° C. with 5% $CO_2$ at either standard atmospheric $O_2$ or at 5% $O_2$. Cells were cultured for 5 days without a media change. Media and non-adherent cells were removed after 5 days of culturing. The adherent cells were maintained in culture.

Actively growing cultures of cells were removed from the flasks with a cell scraper in cold phosphate buffered saline (PBS). The cells were centrifuged for 5 minutes at 300×g. The supernatant was removed and the cells were resuspended in fresh PBS and centrifuged again. The supernatant was removed and the cell pellet was immediately frozen and stored at −80° C. Cellular mRNA was extracted and transcribed into cDNA. The cDNA was then transcribed into cRNA and biotin-labeled. The biotin-labeled cRNA was hybridized with Affymetrix GENECHIP HG-U133A oligonucleotide arrays (Affymetrix, Santa Clara, Calif.). The hybridizations and data collection were performed according to the manufacturer's specifications. Data analysis was performed using "Significance Analysis of Microarrays" (SAM) version 1.21 computer software (Tusher, V. G. et al., 2001, *Proc. Natl. Acad. Sci. USA* 98: 5116-5121). Licenses for the analysis software are available through the Office of Technology Licensing, Stanford University, and more information is available on the World Wide Web at Professor Tibshirani's web site in the Dep't of Statistics, Stanford University.

Fourteen different populations of cells were analyzed in this study. The cells, along with passage information, culture substrate, and culture media are listed in Table 8-1. The cells lines are listed by their identification code along with passage at the time of analysis, cell growth substrate, and growth media.

TABLE 8-1

Cells analyzed by the microarray study.

| Cell Population | Passage | Substrate | Media |
|---|---|---|---|
| Umbilical (022803) | 2 | Gelatin | DMEM, 15% FBS, 2-BME |
| Umbilical (042103) | 3 | Gelatin | DMEM, 15% FBS, 2-BME |
| Umbilical (071003) | 4 | Gelatin | DMEM, 15% FBS, 2-BME |
| Placenta (042203) | 12 | Gelatin | DMEM, 15% FBS, 2-BME |
| Placenta (042903) | 4 | Gelatin | DMEM, 15% FBS, 2-BME |
| Placenta (071003) | 3 | Gelatin | DMEM, 15% FBS, 2-BME |
| ICBM (070203) (5% $O_2$) | 3 | Plastic | MEM 10% FBS |
| ICBM (062703) (std. $O_2$) | 5 | Plastic | MEM 10% FBS |
| ICBM (062703)(5% $O_2$) | 5 | Plastic | MEM 10% FBS |
| hMSC (Lot 2F1655) | 3 | Plastic | MSCGM |
| hMSC (Lot 2F1656) | 3 | Plastic | MSCGM |
| hMSC (Lot 2F1657) | 3 | Plastic | MSCGM |
| hFibroblast (9F0844) | 9 | Plastic | DMEM-F12, 10% FBS |
| hFibroblast (CCD39SK) | 4 | Plastic | DMEM-F12, 10% FBS |

The data were evaluated by principle component analysis with SAM software as described above. The analysis revealed 290 genes that were expressed in different relative amounts in the cells tested. This analysis provided relative comparisons between the populations.

Table 8-2 shows the Euclidean distances that were calculated for the comparison of the cell pairs. The Euclidean distances were based on the comparison of the cells based on the 290 genes that were differentially expressed among the cell types. The Euclidean distance is inversely proportional to similarity between the expression of the 290 genes. The Euclidean distance was calculated for the cell types using these 290 genes expressed differentially between the cell types. Similarity between the cells is inversely proportional to the Euclidean distance.

TABLE 8-2

The Euclidean Distances for the Cell Pairs.

| Cell Pair | Euclidean Distance |
|---|---|
| ICBM-hMSC | 24.71 |
| Placenta-umbilical | 25.52 |
| ICBM-Fibroblast | 36.44 |
| ICBM-placenta | 37.09 |
| Fibroblast-MSC | 39.63 |
| ICBM-Umbilical | 40.15 |
| Fibroblast-Umbilical | 41.59 |
| MSC-Placenta | 42.84 |
| MSC-Umbilical | 46.86 |
| ICBM-placenta | 48.41 |

Tables 8-3, 8-4, and 8-5 show the expression of genes increased in placenta-derived cells (Table 8-3), increased in umbilical cord-derived cells (Table 8-4), and reduced in umbilical cord and placenta-derived cells (Table 8-5).

TABLE 8-3

Genes which are specifically increased in expression in the placenta-derived cells as compared to the other cell lines assayed.

| Probe Set ID | Gene Name | NCBI Accession Number |
|---|---|---|
| 209732_at | C-type (calcium dependent, carbohydrate-recognition domain) lectin, superfamily member 2 (activation-induced) | AF070642 |
| 206067_s_at | Wilms tumor 1 | NM_024426 |
| 207016_s_at | aldehyde dehydrogenase 1 family, member A2 | AB015228 |
| 206367_at | Renin | NM_000537 |
| 210004_at | oxidized low density lipoprotein (lectin-like) receptor 1 | AF035776 |
| 214993_at | *Homo sapiens*, clone IMAGE: 4179671, mRNA, partial cds | AF070642 |
| 202178_at | protein kinase C, zeta | NM_002744 |
| 209780_at | hypothetical protein DKFZp564F013 | AL136883 |
| 204135_at | downregulated in ovarian cancer 1 | NM_014890 |
| 213542_at | *Homo sapiens* mRNA; cDNA DKFZp547K1113 (from clone DKFZp547K1113) | AI246730 |

TABLE 8-4

Genes which are specifically increased in expression in umbilical cord - derived cells as compared to the other cell lines assayed.

| Probe Set ID | Gene Name | NCBI Accession Number |
|---|---|---|
| 202859_x_at | Interleukin 8 | NM_000584 |
| 211506_s_at | Interleukin 8 | AF043337 |
| 210222_s_at | reticulon 1 | BC000314 |
| 204470_at | chemokine (C-X-C motif) ligand 1 (melanoma growth stimulating activity | NM_001511 |
| 206336_at | chemokine (C-X-C motif) ligand 6 (granulocyte chemotactic protein 2) | NM_002993 |
| 207850_at | Chemokine (C-X-C motif) ligand 3 | NM_002090 |
| 203485_at | reticulon 1 | NM_021136 |
| 202644_s_at | tumor necrosis factor, alpha-induced protein 3 | NM_006290 |

TABLE 8-5

Genes which were decreased in expression in the umbilical cord
and placenta cells as compared to the other cell lines assayed.

| Probe Set ID | Gene name | NCBI Accession # |
|---|---|---|
| 210135_s_at | short stature homeobox 2 | AF022654.1 |
| 205824_at | heat shock 27 kDa protein 2 | NM_001541.1 |
| 209687_at | chemokine (C-X-C motif) ligand 12 (stromal cell-derived factor 1) | U19495.1 |
| 203666_at | chemokine (C-X-C motif) ligand 12 (stromal cell-derived factor 1) | NM_000609.1 |
| 212670_at | elastin (supravalvular aortic stenosis, Williams-Beuren syndrome) | AA479278 |
| 213381_at | *Homo sapiens* mRNA; cDNA DKFZp586M2022 (from clone DKFZp586M2022) | N91149 |
| 206201_s_at | mesenchyme homeobox 2 (growth arrest-specific homeobox) | NM_005924.1 |
| 205817_at | Sine oculis homeobox homolog 1 (*Drosophila*) | NM_005982.1 |
| 209283_at | crystallin, alpha B | AF007162.1 |
| 212793_at | dishevelled associated activator of morphogenesis 2 | BF513244 |
| 213488_at | DKFZP586B2420 protein | AL050143.1 |
| 209763_at | similar to neuralin 1 | AL049176 |
| 205200_at | Tetranectin (plasminogen binding protein) | NM_003278.1 |
| 205743_at | src homology three (SH3) and cysteine rich domain | NM_003149.1 |
| 200921_s_at | B-cell translocation gene 1, anti-proliferative | NM_001731.1 |
| 206932_at | cholesterol 25-hydroxylase | NM_003956.1 |
| 204198_s_at | runt-related transcription factor 3 | AA541630 |
| 219747_at | hypothetical protein FLJ23191 | NM_024574.1 |
| 204773_at | Interleukin 11 receptor, alpha | NM_004512.1 |
| 202465_at | Procollagen C-endopeptidase enhancer | NM_002593.2 |
| 203706_s_at | Frizzled homolog 7 (*Drosophila*) | NM_003507.1 |
| 212736_at | hypothetical gene BC008967 | BE299456 |
| 214587_at | Collagen, type VIII, alpha 1 | BE877796 |
| 201645_at | Tenascin C (hexabrachion) | NM_002160.1 |
| 210239_at | iroquois homeobox protein 5 | U90304.1 |
| 203903_s_at | Hephaestin | NM_014799.1 |
| 205816_at | integrin, beta 8 | NM_002214.1 |
| 203069_at | synaptic vesicle glycoprotein 2 | NM_014849.1 |
| 213909_at | *Homo sapiens* cDNA FLJ12280 fis, clone MAMMA1001744 | AU147799 |
| 206315_at | cytokine receptor-like factor 1 | NM_004750.1 |
| 204401_at | potassium intermediate/small conductance calcium-activated channel, subfamily N, member 4 | NM_002250.1 |
| 216331_at | integrin, alpha 7 | AK022548.1 |
| 209663_s_at | integrin, alpha 7 | AF072132.1 |
| 213125_at | DKFZP586L151 protein | AW007573 |
| 202133_at | transcriptional co-activator with PDZ-binding motif (TAZ) | AA081084 |
| 206511_s_at | Sine oculis homeobox homolog 2 (*Drosophila*) | NM_016932.1 |
| 213435_at | KIAA1034 protein | AB028957.1 |
| 206115_at | early growth response 3 | NM_004430.1 |
| 213707_s_at | distal-less homeobox 5 | NM_005221.3 |
| 218181_s_at | hypothetical protein FLJ20373 | NM_017792.1 |
| 209160_at | aldo-keto reductase family 1, member C3 (3-alpha hydroxysteroid dehydrogenase, type II) | AB018580.1 |
| 213905_x_at | Biglycan | AA845258 |
| 201261_x_at | Biglycan | BC002416.1 |
| 202132_at | transcriptional co-activator with PDZ-binding motif (TAZ) | AA081084 |
| 214701_s_at | fibronectin 1 | AJ276395.1 |
| 213791_at | Proenkephalin | NM_006211.1 |
| 205422_s_at | Integrin, beta-like 1 (with EGF-like repeat domains) | NM_004791.1 |
| 214927_at | *Homo sapiens* mRNA full length insert cDNA clone EUROIMAGE 1968422 | AL359052.1 |
| 206070_s_at | EphA3 | AF213459.1 |
| 212805_at | KIAA0367 protein | AB002365.1 |
| 219789_at | natriuretic peptide receptor C/guanylate cyclase C (atrionatriuretic peptide receptor C) | AI628360 |
| 219054_at | hypothetical protein FLJ14054 | NM_024563.1 |
| 213429_at | *Homo sapiens* mRNA; cDNA DKFZp564B222 (from clone DKFZp564B222) | AW025579 |
| 204929_s_at | vesicle-associated membrane protein 5 (myobrevin) | NM_006634.1 |
| 201843_s_at | EGF-containing fibulin-like extracellular matrix protein 1 | NM_004105.2 |
| 221478_at | BCL2/adenovirus E1B 19 kDa interacting protein 3-like | AL132665.1 |
| 201792_at | AE binding protein 1 | NM_001129.2 |
| 204570_at | cytochrome c oxidase subunit VIIa polypeptide 1 (muscle) | NM_001864.1 |
| 201621_at | neuroblastoma, suppression of tumorigenicity 1 | NM_005380.1 |
| 202718_at | Insulin-like growth factor binding protein 2, 36 kDa | NM_000597.1 |

Tables 8-6, 8-7, and 8-8 show the expression of genes increased in human fibroblasts (Table 8-6), ICBM cells (Table 8-7), and MSCs (Table 8-8).

TABLE 8-6

Genes which were increased in expression in fibroblasts as compared to the other cell lines assayed.

dual specificity phosphatase 2
KIAA0527 protein
Homo sapiens cDNA: FLJ23224 fis, clone ADSU02206
dynein, cytoplasmic, intermediate polypeptide 1
ankyrin 3, node of Ranvier (ankyrin G)
inhibin, beta A (activin A, activin AB alpha polypeptide)
ectonucleotide pyrophosphatase/phosphodiesterase 4 (putative function)
KIAA1053 protein
microtubule-associated protein 1A
zinc finger protein 41
HSPC019 protein
Homo sapiens cDNA: FLJ23564 fis, clone LNG10773
Homo sapiens mRNA; cDNA DKFZp564A072 (from clone DKFZp564A072)
LIM protein (similar to rat protein kinase C-binding enigma)
inhibitor of kappa light polypeptide gene enhancer in B-cells, kinase complex-associated protein
hypothetical protein FLJ22004
Human (clone CTG-A4) mRNA sequence
ESTs, Moderately similar to cytokine receptor-like factor 2; cytokine receptor CRL2 precursor [Homo sapiens]
transforming growth factor, beta 2
hypothetical protein MGC29643
antigen identified by monoclonal antibody MRC OX-2
putative X-linked retinopathy protein

TABLE 8-7

Genes which were increased in expression in the ICBM-derived cells as compared to the other cell lines assayed.

cardiac ankyrin repeat protein
MHC class I region ORF
integrin, alpha 10
hypothetical protein FLJ22362
UDP-N-acetyl-alpha-D-galactosamine:polypeptide N-acetylgalactosaminyltransferase 3 (GalNAc-T3)
interferon-induced protein 44
SRY (sex determining region Y)-box 9 (campomelic dysplasia, autosomal sex-reversal)
keratin associated protein 1-1
hippocalcin-like 1
jagged 1 (Alagille syndrome)
proteoglycan 1, secretory granule

TABLE 8-8

Genes which were increased in expression in the MSC cells as compared to the other cell lines assayed.

interleukin 26
maltase-glucoamylase (α-glucosidase)
nuclear receptor subfamily 4, group A, member 2
v-fos FBJ murine osteosarcoma viral oncogene homolog
hypothetical protein DC42
nuclear receptor subfamily 4, group A, member 2
FBJ murine osteosarcoma viral oncogene homolog B
WNT1 inducible signaling pathway protein 1
MCF.2 cell line derived transforming sequence
potassium channel, subfamily K, member 15
cartilage paired-class homeoprotein 1
Homo sapiens cDNA FLJ12232 fis, clone MAMMA1001206
Homo sapiens cDNA FLJ34668 fis, clone LIVER2000775
jun B proto-oncogene
B-cell CLL/lymphoma 6 (zinc finger protein 51)
zinc finger protein 36, C3H type, homolog (mouse)

This example was performed to provide a molecular characterization of the cells derived from umbilical cord and placenta. This analysis included cells derived from three different umbilical cords and three different placentas. The study also included two different lines of dermal fibroblasts, three lines of mesenchymal stem cells, and three lines of iliac crest bone marrow cells. The mRNA that was expressed by these cells was analyzed on a GENECHIP oligonucleotide array that contained oligonucleotide probes for 22,000 genes.

The analysis revealed that transcripts for 290 genes were present in different amounts in these five different cell types. These genes include ten genes that are specifically increased in the placenta-derived cells and seven genes specifically increased in the umbilical cord-derived cells. Fifty-four genes were found to have specifically lower expression levels in placenta-derived and umbilical cord tissue-derived cells.

Example 9

Immunohistochemical Characterization of Cellular Phenotypes

The phenotypes of cells found within human umbilical cord tissue were analyzed by immunohistochemistry.

Human umbilical cord tissue was harvested and immersion fixed in 4% (w/v) paraformaldehyde overnight at 4° C. Immunohistochemistry was performed using antibodies directed against the following epitopes (see Table 8-1): vimentin (1:500; Sigma, St. Louis, Mo.), desmin (1:150, raised against rabbit; Sigma; or 1:300, raised against mouse; Chemicon, Temecula, Calif.), alpha-smooth muscle actin (SMA; 1:400; Sigma), cytokeratin 18 (CK18; 1:400; Sigma), von Willebrand Factor (vWF; 1:200; Sigma), and CD34 (human CD34 Class III; 1:100; DAKOCytomation, Carpinteria, Calif.). In addition, the following markers were tested: anti-human GROalpha-PE (1:100; Becton Dickinson, Franklin Lakes, N.J.), anti-human GCP-2 (1:100; Santa Cruz Biotech, Santa Cruz, Calif.), anti-human oxidized LDL receptor 1 (ox-LDL R1; 1:100; Santa Cruz Biotech), and anti-human NOGO-A (1:100; Santa Cruz Biotech). Fixed specimens were trimmed with a scalpel and placed within OCT embedding compound (Tissue-Tek OCT; Sakura, Torrance, Calif.) on a dry ice bath containing ethanol. Frozen blocks were then sectioned (10 μm thick) using a standard cryostat (Leica Microsystems) and mounted onto glass slides for staining.

Immunohistochemistry was performed similar to previous studies. (E.g., Messina et al., Exper. Neurol., 2003; 184: 816-829). Tissue sections were washed with phosphate-buffered saline (PBS) and exposed to a protein blocking solution containing PBS, 4% (v/v) goat serum (Chemicon, Temecula, Calif.), and 0.3% (v/v) Triton (Triton X-100; Sigma) for 1 hour to access intracellular antigens. In instances where the epitope of interest would be located on the cell surface (CD34, ox-LDL R1), triton was omitted in all steps of the procedure in order to prevent epitope loss. Furthermore, in instances where the primary antibody was raised against goat (GCP-2, ox-LDL R1, NOGO-A), 3% (v/v) donkey serum was used in place of goat serum throughout the procedure. Primary antibodies, diluted in blocking solution, were then applied to the sections for a period of 4 hours at room temperature. Primary antibody solutions were removed, and cultures washed with PBS prior to application of secondary antibody solutions (1 hour at room temperature) containing block along with goat anti-mouse IgG-Texas Red (1:250; Molecular Probes, Eugene, Oreg.) and/or goat anti-rabbit IgG-Alexa 488 (1:250; Molecular Probes) or donkey anti-goat IgG-FITC (1:150; Santa Cruz Biotech). Cultures were washed, and 10 micromolar DAPI (Molecular Probes) was applied for 10 minutes to visualize cell nuclei.

Following immune-staining, fluorescence was visualized using the appropriate fluorescence filter on an Olympus inverted epifluorescent microscope (Olympus, Melville, N.Y.). Positive staining was represented by fluorescence signal above control staining. Representative images were captured using a digital color video camera and ImagePro software (Media Cybernetics, Carlsbad, Calif.). For triple-stained samples, each image was taken using only one emission filter at a time. Layered montages were then prepared using Adobe Photoshop software (Adobe, San Jose, Calif.).

TABLE 9-1

Summary of Primary Antibodies Used

| Antibody | Concentration | Vendor |
| --- | --- | --- |
| Vimentin | 1:500 | Sigma, St. Louis, MO |
| Desmin (rb) | 1:150 | Sigma |
| Desmin (m) | 1:300 | Chemicon, Temecula, CA |
| alpha-smooth muscle actin (SMA) | 1:400 | Sigma |
| Cytokeratin 18 (CK18) | 1:400 | Sigma |
| von Willebrand factor (vWF) | 1:200 | Sigma |
| CD34 III | 1:100 | DakoCytomation, Carpinteria, CA |
| GROalpha-PE | 1:100 | BD, Franklin Lakes, NJ |
| GCP-2 | 1:100 | Santa Cruz Biotech |
| Ox-LDL R1 | 1:100 | Santa Cruz Biotech |
| NOGO-A | 1:100 | Santa Cruz Biotech |

Vimentin, desmin, SMA, CK18, vWF, and CD34 markers were expressed in a subset of the cells found within umbilical cord (data not shown). In particular, vWF and CD34 expression were restricted to blood vessels contained within the cord. CD34 positive (CD34+) cells were on the innermost layer (lumen side). Vimentin expression was found throughout the matrix and blood vessels of the cord. SMA was limited to the matrix and outer walls of the artery and vein, but not contained within the vessels themselves. CK18 and desmin were observed within the vessels only, desmin being restricted to the middle and outer layers.

None of these markers were observed within umbilical cord (data not shown).

Vimentin, desmin, alpha-smooth muscle actin, cytokeratin 18, von Willebrand Factor, and CD 34 are expressed in cells within human umbilical cord. Based on in vitro characterization studies showing that only vimentin and alpha-smooth muscle actin are expressed, the data suggests that the current process of umbilical cord-derived cell isolation harvests a subpopulation of cells or that the cells isolated change expression of markers to express vimentin and alpha-smooth muscle actin.

Example 10

Secretion of Trophic Factors

The secretion of selected trophic factors from UTC was measured. Factors were selected that have angiogenic activity e.g., hepatocyte growth factor (HGF) (Rosen et al., *Ciba Found. Symp.*, 1997; 212:215-26); monocyte chemotactic protein 1 (MCP-1) (Salcedo et al., *Blood*, 2000; 96; 34-40); interleukin-8 (IL-8) (Li et al., *J. Immunol.*, 2003; 170:3369-76); keratinocyte growth factor (KGF); basic fibroblast growth factor (bFGF); vascular endothelial growth factor (VEGF) (Hughes et al., *Ann. Thorac. Surg.* 2004; 77:812-8); tissue inhibitor of matrix metalloproteinase 1 (TIMP1); angiopoietin 2 (ANG2); platelet derived growth factor (PDGFbb); thrombopoietin (TPO); heparin-binding epidermal growth factor (HB-EGF); stromal-derived factor 1alpha (SDF-1alpha), neurotrophic/neuroprotective activity (brain-derived neurotrophic factor (BDNF) (Cheng et al., *Dev. Biol.*, 2003; 258; 319-33); interleukin-6 (IL-6); granulocyte chemotactic protein-2 (GCP-2); transforming growth factor beta2 (TGFbeta2)); or chemokine activity (macrophage inflammatory protein 1alpha (MIP1alpha); macrophage inflammatory protein 1 beta (MIP1beta); monocyte chemoattractant-1 (MCP-1); Rantes (regulated on activation, normal T cell expressed and secreted); 1309; thymus and activation-regulated chemokine (TARC); Eotaxin; macrophage-derived chemokine (MDC); and (IL-8).

Cells derived from umbilical cord, as well as human fibroblasts derived from human neonatal foreskin, were cultured in growth medium on gelatin-coated T75 flasks. Cells were cryopreserved at passage 11 and stored in liquid nitrogen. After thawing, growth medium was added to the cells, followed by transfer to a 15 ml centrifuge tube and centrifugation of the cells at 150×g for 5 minutes. The cell pellet was resuspended in 4 ml growth medium, and the cells were counted. Cells were seeded at 5,000 cells/cm$^2$ in T75 flasks each containing 15 ml of growth medium, and cultured for 24 hours. The medium was changed to a serum-free medium (DMEM-low glucose (Gibco), 0.1% (w/v) bovine serum albumin (Sigma), penicillin (50 U/ml) and streptomycin (50 µg/ml, Gibco)) for 8 hours. Conditioned serum-free medium was collected at the end of incubation by centrifugation at 14,000×g for 5 minutes and stored at −20° C.

To estimate the number of cells in each flask, the cells were washed with phosphate-buffered saline (PBS) and detached using 2 ml trypsin/EDTA (Gibco). Trypsin activity was inhibited by addition of 8 ml growth medium. The cells were centrifuged at 150×g for 5 minutes. The supernatant was removed, and the cells were resuspended in 1 ml Growth Medium. The cell number was estimated with a hemocytometer.

Cells were grown at 37° C. in 5% $CO_2$ and atmospheric oxygen. The amount of MCP-1, IL-6, VEGF, SDF-1alpha, GCP-2, IL-8, and TGF-beta2 produced by each cell sample was determined by ELISA (R&D Systems, Minneapolis, Minn.). All assays were performed according to the manufacturer's instructions. Values presented are picograms per ml per million cells (n=2, sem).

Chemokines (MIN1alpha, MIP1beta, MCP-1, Rantes, I309, TARC, Eotaxin, MDC, IL8), BDNF, and angiogenic factors (HGF, KGF, bFGF, VEGF, TIMP1, ANG2, PDGFbb, TPO, HB-EGF were measured using SearchLight Proteome Arrays (Pierce Biotechnology Inc.). The Proteome Arrays are multiplexed sandwich ELISAs for the quantitative measurement of two to sixteen proteins per well. The arrays are produced by spotting a 2×2, 3×3, or 4×4 pattern of four to sixteen different capture antibodies into each well of a 96-well plate. Following a sandwich ELISA procedure, the entire plate is imaged to capture the chemiluminescent signal generated at each spot within each well of the plate. The signal generated at each spot is proportional to the amount of target protein in the original standard or sample.

MCP-1 and IL-6 were secreted by umbilicus-derived PPDCs and dermal fibroblasts (Table 10-1). SDF-1alpha and GCP-2 were secreted by fibroblasts. GCP-2 and IL-8 were secreted by umbilicus-derived PPDCs. TGF-beta2 was not detected from either cell type by ELISA.

Umbilicus-derived cells secreted a number of trophic factors. Some of these trophic factors, such as HGF, bFGF, MCP-1 and IL-8, play important roles in angiogenesis. Other trophic factors, such as BDNF and IL-6, have important roles in neural regeneration or protection.

Example 11

Assay for Telomerase Activity

Telomerase functions to synthesize telomere repeats that serve to protect the integrity of chromosomes and to prolong the replicative life span of cells (Liu, K, et al., *PNAS*, 1999; 96:5147-5152). Telomerase consists of two components, telomerase RNA template (hTER) and telomerase reverse

TABLE 10-1

| ELISA Results: Detection of Trophic Factors | | | | | | | |
|---|---|---|---|---|---|---|---|
| | MCP-1 | IL-6 | VEGF | SDF-1α | GCP-2 | IL-8 | TGF-beta2 |
| Fibroblast | 17 ± 1 | 61 ± 3 | 29 ± 2 | 19 ± 1 | 21 ± 1 | ND | ND |
| Umbilical (022803) | 1150 ± 74 | 4234 ± 289 | ND | ND | 160 ± 11 | 2058 ± 145 | ND |
| Umbilical (071003) | 2794 ± 84 | 1356 ± 43 | ND | ND | 2184 ± 98 | 2369 ± 23 | ND |

Key:
ND: Not Detected.,
=/− sem

Searchlight™ Multiplexed ELISA assay. TIMP1, TPO, KGF, HGF, FGF, HBEGF, BDNF, MIP1beta, MCP1, RANTES, I309, TARC, MDC, and IL-8 were secreted from umbilicus-derived PPDCs (Tables 10-2 and 10-3). No Ang2, VEGF, or PDGFbb were detected.

transcriptase (hTERT). Regulation of telomerase is determined by transcription of hTERT but not hTER. Real-time polymerase chain reaction (PCR) for hTERT mRNA thus is an accepted method for determining telomerase activity of cells.

TABLE 10-2

| Searchlight ™ Multiplexed ELISA assay results | | | | | | | | | |
|---|---|---|---|---|---|---|---|---|---|
| | TIMP1 | ANG2 | PDGFbb | TPO | KGF | HGF | FGF | VEGF | HBEGF | BDNF |
| hFB | 19306.3 | ND | ND | 230.5 | 5.0 | ND | ND | 27.9 | 1.3 | ND |
| U1 | 57718.4 | ND | ND | 1240.0 | 5.8 | 559.3 | 148.7 | ND | 9.3 | 165.7 |
| U3 | 21850.0 | ND | ND | 1134.5 | 9.0 | 195.6 | 30.8 | ND | 5.4 | 388.6 |

Key:
hFB (human fibroblasts),
U1 (umbilicus-derived PPDC (022803)),
U3 (umbilicus-derived PPDC (071003)),
ND: Not Detected.

TABLE 10-3

| Searchlight ™ Multiplexed ELISA assay results | | | | | | | | |
|---|---|---|---|---|---|---|---|---|
| | MIP1a | MIP1b | MCP1 | RANTES | I309 | TARC | Eotaxin | MDC | IL8 |
| hFB | ND | ND | 39.6 | ND | ND | 0.1 | ND | ND | 204.9 |
| U1 | ND | 8.0 | 1694.2 | ND | 22.4 | 37.6 | ND | 18.9 | 51930.1 |
| U3 | ND | 5.2 | 2018.7 | 41.5 | 11.6 | 21.4 | ND | 4.8 | 10515.9 |

Key:
hFB (human fibroblasts),
U1 (umbilicus-derived PPDC (022803)),
U3 (umbilicus-derived PPDC (071003)),
ND: Not Detected Cell Isolation Real-time PCR experiments were performed to determine telomerase production of human umbilical cord tissue-derived cells. Human umbilical cord tissue-derived cells were prepared in accordance with the above Examples and the examples set forth in U.S. Pat. No. 7,510,873. Generally, umbilical cords obtained from National Disease Research Interchange (Philadelphia, Pa.) following a normal delivery were washed to remove blood and debris and mechanically dissociated. The tissue was then incubated with digestion enzymes including collagenase, dispase, and hyaluronidase in culture medium at 37° C. Human umbilical cord tissue-derived cells were cultured according to the methods set forth in the examples of the '012 application. Mesenchymal stem cells and normal dermal skin fibroblasts (cc-2509 lot #9F0844) were obtained from Cambrex, Walkersville, Md. A pluripotent human testicular embryonal carcinoma (teratoma) cell line nTera-2 cells (NTERA-2 cl.Dl) (See, Plaia et al., *Stem Cells,* 2006; 24(3):531-546) was purchased from ATCC (Manassas, Va.) and was cultured according to the methods set forth in U.S. Pat. No. 7,510,873.

Total RNA Isolation

RNA was extracted from the cells using RNeasy® kit (Qiagen, Valencia, Calif.). RNA was eluted with 50 µl DEPC-treated water and stored at −80° C. RNA was reverse transcribed using random hexamers with the TaqMan® reverse transcription reagents (Applied Biosystems, Foster City, Calif.) at 25° C. for 10 minutes, 37° C. for 60 minutes and 95° C. for 10 minutes. Samples were stored at −20° C.

Real-Time PCR

PCR was performed on cDNA samples using the Applied Biosystems Assays-On-Demand™ (also known as Taq-Man® Gene Expression Assays) according to the manufacturer's specifications (Applied Biosystems). This commercial kit is widely used to assay for telomerase in human cells. Briefly, hTert (human telomerase gene) (Hs00162669) and human GAPDH (an internal control) were mixed with cDNA and TaqMan® Universal PCR master mix using a 7000 sequence detection system with ABI prism 7000 SDS software (Applied Biosystems). Thermal cycle conditions were initially 50° C. for 2 minutes and 95° C. for 10 minutes followed by 40 cycles of 95° C. for 15 seconds and 60° C. for 1 minute. PCR data was analyzed according to the manufacturer's specifications.

Human umbilical cord tissue-derived cells (ATCC Accession No. PTA-6067), fibroblasts, and mesenchymal stem cells were assayed for hTert and 18S RNA. As shown in Table 11-1, hTert, and hence telomerase, was not detected in human umbilical cord tissue-derived cells.

TABLE 11-1

|  | hTert | 18S RNA |
|---|---|---|
| Umbilical cells (022803) | ND | + |
| Fibroblasts | ND | + |

ND—not detected;
+ signal detected

Human umbilical cord tissue-derived cells (isolate 022803, ATCC Accession No. PTA-6067) and nTera-2 cells were assayed and the results showed no expression of telomerase in two lots of human umbilical cord tissue-derived cells while the teratoma cell line revealed high level of expression (Table 11-2).

TABLE 11-2

|  | hTert | | GAPDH | | |
|---|---|---|---|---|---|
| Cell type | Exp. 1 | Exp. 2 | Exp. 1 | Exp. 2 | hTert norm |
| nTera2 | 25.85 | 27.31 | 16.41 | 16.31 | 0.61 |
| 022803 | — | — | 22.97 | 22.79 | — |

Therefore, it can be concluded that the human umbilical tissue-derived cells as disclosed herein do not express telomerase.

While the invention has been described and illustrated herein by references to various specific materials, procedures and examples, it is understood that the invention is not restricted to the particular combinations of material and procedures selected for that purpose. Numerous variations of such details can be implied as will be appreciated by those skilled in the art. It is intended that the specification and examples be considered as exemplary, only, with the true scope and spirit of the invention being indicated by the following claims. All references, patents, and patent applications referred to in this application are herein incorporated by reference in their entirety.

What is claimed is:

1. A method of identifying circulating human umbilical cord tissue-derived cells in a blood sample from a patient after the patient has been treated with the human umbilical cord tissue-derived cells comprising:
   (a) assaying human umbilical cord tissue-derived cells and patient peripheral blood mononuclear cells to identify one or more markers positive for human umbilical cord tissue-derived cells and one or more markers positive for patient peripheral blood mononuclear cells;
   (b) comparing the one or more markers positive for human umbilical cord tissue-derived cells and the one or more markers positive for patient peripheral blood mononuclear cells to identify one or more unique markers which distinguishes the umbilical cord tissue-derived cells from the patient peripheral blood mononuclear cells;
   (c) providing a blood sample from a patient that has been treated with human umbilical cord tissue-derived cells;
   (d) analyzing the blood sample from the patient using an assay method to detect the one or more unique markers;
   (e) differentiating between circulating human umbilical cord tissue-derived cells administered to the patient and peripheral blood mononuclear cells from the patient based on the detection of the one or more unique markers; and
   (f) identifying the circulating human umbilical cord-tissue-derived cells.

2. The method of claim 1, wherein the one or more markers positive for human umbilical cord tissue-derived cells and one or more markers positive for patient peripheral blood mononuclear cells selected from the group consisting of CD10, CD13, NRP1, CD45, LAMP1, DKK3, NRP1, LAMB1, and combinations thereof.

3. The method of claim 1, wherein the one or more unique markers for human umbilical cord tissue-derived cells are selected from the group consisting of CD10, CD13, NRP1, LAMP1, DKK3, NRP1, LAMB1, and combinations thereof.

4. The method of claim 1, wherein the marker positive for patient peripheral blood mononuclear cells is CD45 and the marker positive for human umbilical cord tissue-derived cells is CD10.

5. The method of claim 4 further comprising CD13 as the marker positive for human umbilical cord tissue-derived cells.

6. The method of claim 4 further comprising one or more of NRP1, DKK3, and LAMP1 as the marker positive for human umbilical cord tissue-derived cells.

7. The method of claim 1, wherein the assay method in step (b) is selected from the group consisting of flow cytometry, ELISA, immunohistochemistry, nucleic acid detection, PCR, and combinations thereof.

8. The method of claim 1, further comprising performing an enrichment step between steps (c) and (d).

9. The method of claim 8, wherein the enrichment step is magnetic capture technology.

10. The method of claim 1, wherein the patient is a human, non-human primate, mouse, rat, hamster, guinea pig, dog, or pig.

11. The method of claim 1, wherein the human umbilical cord tissue-derived cells are isolated from human umbilical cord tissue substantially free of blood, are capable of self-renewal and expansion in culture, have the potential to differentiate, and have the following characteristics: (1) express CD10, CD13, CD44, CD90, and HLA-ABC; (2) do not express CD31, CD34, CD45, HLA-DR and CD117; and (3) do not express hTERT or telomerase.

12. A method of identifying circulating human umbilical cord tissue-derived cells in a blood sample comprising the steps of:
  a. assaying human umbilical cord tissue-derived cells and human peripheral blood mononuclear cells to identify one or more markers positive for human umbilical cord tissue-derived cells and one or more markers positive for human peripheral blood mononuclear cells;
  b. providing a blood sample from a patient after human umbilical cord tissue-derived cells have been administered to the patient;
  c. isolating the human umbilical cord tissue-derived cell/human peripheral blood mononuclear cell fraction from the blood sample;
  d. analyzing the human umbilical cord tissue-derived cell/human peripheral blood mononuclear cell fraction by flow cytometry for CD45 as a positive marker for peripheral blood mononuclear cell and CD10 or CD13 as a positive marker for human umbilical cord tissue-derived cells; and
  e. identifying circulating human umbilical cord tissue-derived cells by detecting the presence of the human peripheral blood mononuclear cells and human umbilical cord tissue-derived cells based on the detection of CD45 and CD10 or CD13,
  wherein the one or more markers positive for human umbilical cord tissue-derived cells comprises CD10 or CD13, and
  wherein the one or more markers positive for human peripheral blood mononuclear cells comprises CD45.

13. The method of claim 12, wherein the step of analyzing comprises analysis of the human umbilical cord tissue-derived cell/peripheral blood mononuclear cell fraction by flow cytometry for CD45 as the marker for human peripheral blood mononuclear cell and CD10 as positive for human umbilical cord tissue-derived cells.

14. The method of claim 12, wherein the step of analyzing comprises analysis of the human umbilical cord tissue-derived cell/peripheral blood mononuclear cell fraction by flow cytometry for CD45 as a positive marker for human peripheral blood mononuclear cell and CD13 as the marker positive for human umbilical cord tissue-derived cells.

15. The method of claim 12, further comprising performing an enrichment step prior to analyzing the human umbilical cord tissue-derived cell/human peripheral blood mononuclear cell fraction.

16. The method of claim 15 wherein the enrichment step is magnetic capture technology.

17. The method of claim 12, wherein the step of detecting comprises differentiating between human umbilical cord tissue-derived cells administered to the patient and human peripheral blood mononuclear cells from the patient.

18. A method of identifying human umbilical cord tissue-derived cells in a blood sample comprising the steps of:
  a. providing a blood sample from a human patient to whom human umbilical cord tissue-derived cells were administered;
  b. isolating the human umbilical cord tissue-derived cell/peripheral blood mononuclear cell fraction from the blood sample;
  c. removing any plasma;
  d. analyzing the human umbilical cord tissue-derived cell/peripheral blood mononuclear cell fraction by flow cytometry for CD45 as a positive marker for human peripheral blood mononuclear cell and CD13 as a positive marker for human umbilical cord tissue-derived cells; and
  e. differentiating between human peripheral blood mononuclear cells and human umbilical cord tissue-derived cells based on the detection of CD45 and CD13, and thereby identifying the human umbilical cord tissue-derived cells.

19. The method of claim 18 further comprising analyzing for CD10 as a marker positive for human umbilical cord tissue-derived cells.

20. The method of claim 18, wherein the human umbilical cord tissue-derived cells are isolated from human umbilical cord tissue substantially free of blood, are capable of self-renewal and expansion in culture, have the potential to differentiate, and have the following characteristics: (1) express CD10, CD13, CD44, CD90, and HLA-ABC; (2) do not express CD31, CD34, CD45, HLA-DR and CD117; (3) do not express hTERT or telomerase; (4) express oxidized low density lipoprotein receptor 1, reticulon, chemokine receptor ligand 3, and/or granulocyte chemotactic protein; and (4) express, relative to a human fibroblast, mesenchymal stem cell, or iliac crest bone marrow cell, increased levels of interleukin 8 or reticulon 1.

21. The method of claim 18, further comprising performing an enrichment step prior to analyzing the human umbilical cord tissue-derived cell/human peripheral blood mononuclear cell fraction.

22. The method of claim 21 wherein the enrichment step is magnetic capture technology.

23. The method of claim 18, wherein the step of detecting comprises differentiating between human umbilical cord tissue-derived cells administered to the patient and human peripheral blood mononuclear cells from the patient.

24. A method of detecting circulating human umbilical cord tissue-derived cells in a blood sample comprising:
  a. assaying human umbilical cord tissue-derived cells and human peripheral blood mononuclear cells to identify one or more markers positive for human umbilical cord tissue-derived cells and one or more markers positive for human peripheral blood mononuclear cells;
  b. comparing the one or more markers positive for human umbilical cord tissue-derived cells and the one or more markers positive for human peripheral blood mononuclear cells to identify one or more unique markers which distinguishes the umbilical cord tissue-derived cells from the patient peripheral blood mononuclear cells;
c. providing a blood sample from a human patient that has been treated with human umbilical cord tissue-derived cells;
d. analyzing the sample using an assay method to detect the one or more unique markers positive; and
e. detecting circulating human umbilical cord tissue-derived cells by distinguishing between the human peripheral blood mononuclear cells and human umbilical cord tissue-derived cells based on the detection of the one or more unique markers.

* * * * *